(12) United States Patent
Jefferson et al.

(10) Patent No.: US 6,391,547 B1
(45) Date of Patent: May 21, 2002

(54) MICROBIAL β-GLUCURONIDASE GENES, GENE PRODUCTS AND USES THEREOF

(75) Inventors: Richard A. Jefferson, Googong; Rebecca Louise Harcourt, Sydney; Andrzej Kilian, Kaleen; Katherine Joanna Wilson, Townsville; Paul Konrad Keese, Curtin, all of (AU)

(73) Assignee: Center for the Application of Molecular Biology to International Agriculture, Canberra (AU)

( * ) Notice: Subject to any disclaimer, the term of this patent is extended or adjusted under 35 U.S.C. 154(b) by 0 days.

(21) Appl. No.: 09/149,727

(22) Filed: Sep. 8, 1998

Related U.S. Application Data

(62) Division of application No. 08/882,704, filed on Jun. 25, 1997, now Pat. No. 5,879,906.
(60) Provisional application No. 60/058,263, filed on Sep. 9, 1997.

(51) Int. Cl.$^7$ .......................... C07H 21/04; C12Q 1/68; C12P 21/00; C12N 15/63; C12N 5/00; C12N 15/85
(52) U.S. Cl. .................. 435/6; 536/23.2; 536/24.1; 435/69.1; 435/320.1; 435/325; 435/455
(58) Field of Search .................. 435/6, 69.1, 320.1, 435/325, 410, 455, 469, 471; 536/23.2, 23.7, 24.1

(56) References Cited

U.S. PATENT DOCUMENTS 5,599,670 A * 2/1997 Jeffereson ................ 435/6

FOREIGN PATENT DOCUMENTS

| GB | 2197653 | 5/1988 |
|---|---|---|
| JP | 4023982 A | 1/1992 |
| JP | 4267876 A | 9/1992 |
| JP | 6256196 A | 9/1994 |
| JP | 7274948 A | 10/1995 |
| WO | WO89 03880 | 5/1989 |
| WO | WO96 37609 | 11/1996 |
| WO | WO99 13085 | 3/1999 |

OTHER PUBLICATIONS

Cheon et al. Nodullin–24 follows a novel pathway for integration into the peribacteroid membrane in soybean root nodules. J. Biol. Chem. vol. 269(9):6598–6602 Mar. 1994.*

Farrell et al. Manipulation of beta –glucuronidase for use as a reporter in vacuolar targetting studies. Plant Mol. Biol. vol. 15:521–825 Jun. 1990.*

Chan et al. Novel gene expression system for plant cells gbased on induction of alpha–amylase promoter by carbohydrate starvation. J. Biol. Chem. vol. 269(26):17635–17641 Jul. 1994.*

Pang et al. Use of the signal peptide of Pisum viciln to translocate beta–glucuronidase in Nicotania tabacum. Gene. vol. 112:229–234 Apr. 1992.*

Iturriaga et al. Endoplasmic reticulum targeting and glycosylation of hybrid proteins in transgenic tobacco. The Plant Cell. vol. 1:381–390 Mar. 1989.*

Nelson KE et al., *Thermotoga maritime* beta–glucuronidase, Database PIR2 'Online' EMBL, Heidelberg, Germany; ID/AC AE001766; Q9X0F2, Jun. 1999, nucleotides 4542 to 6233.

Nelson KE et al., Evidence for latereral gene transfer between Archaea and Bacteria from genome sequence of *Thermotoga maritime, Nature* 399: 323–329, 1999.

Russell WM and Klaenhammer TR, Identification and Cloning of gusA, Encoding a New β–Glucuronidase from *Lactobacillus gasseri* ADH, *Applied and Environmental Microbiology* 67: 1253–1261, 2001.

Firek et al., "Endoplasmic reticulum targeting of active modified β–glucuronidase (GUS) in transgenic tobacco plants," *Transgenic Research* 3, 326–331 (1994).

Akao et al., "Glycyrrhizin β–D–Glucuronidase of *Eubacterium* sp. From Human Intestinal Flora," *Chem. Pharm. Bull.* 35(2): 705–710, 1987.

Akao, "Purification and Characterization of Glycyrrhetic Acid Mono–glucuronide β–D–Glucuronidase in *Eubacterium* sp. GLH," *Biol. Pharm. Bull.* 22(1): 80–82, 1999.

Blattner et al., "the Complete Genome Sequence of *Escherichia coli* K–12," *Science* 277:1453–1462, 1997 (+ Database EMBL –EMPRO Entry ECAE257, Acc. NO. AE000257; U00096, Jan. 29, 1997).

Dean et al., "Iodinated fibroblast β–glucuronidase as a ligand for receptor–mediated endocytosis," *Biochem. J.* 229: 213–219, 1985.

Denecke et al., "Protein Secretion in Plant Cells Can Occur via a Default Pathway," *The Plant Cell* 2: 51–59, 1990.

Fan et al., "Determination and comparison of β–glucuronidase activity among strains of *B. fragilis* and *E. coli,*" *Hua.His.I.Ko.Ta.Hsueh.Hsueh.Pao.* 22(2): 211–212, 1991.

Ikeda et al., "Variations in concentrations of bacterial metabolites, enzyme activities, moisture, pH and bacterial composition between and within individuals in faeces of seven healthy adults," *Journal of Applied Bacteriology* 77: 185–194, 1994.

Islam et al., "C–terminal Processing of Human β–Glucuronidase. The Propetide Is Required For Full Expression Of Catalytic Activity, Intracellular Retention, And Proper Phosphorylation," *J. Biol. Chem.* 268(30): 22627–22633, 1993.

(List continued on next page.)

*Primary Examiner*—Terry McKelvey
*Assistant Examiner*—William Sandals
(74) *Attorney, Agent, or Firm*—Foley & Lardner

(57) ABSTRACT

Genes encoding microbial β-glucuronidase and protein that is secreted and its uses are provided.

37 Claims, 20 Drawing Sheets

OTHER PUBLICATIONS

Jain et al., "Structure of human β–glucurondiase reveals candidate lysosomal targeting and active–site motifs," *Nat. Struct. Biol.* 3(4): 375–381, 1996.

Jefferson et al., "GUS fusion : β–glucurondiase as a sensitive and versatile gene fusion marker in higher plants, " *The EMBO Journal* 6(13): 3901–3907, 1987.

Kelley et al., "Influence of Hypercholesterolemia and Cholesterol Accumulation on Rabbit Carrageenan Granuloma Macrophage Activation," *American Journal of Pathology* 131(3):539–546, 1988.

Sakaguchi and Murata, "β–Glucuronidase of Clostridium perfringens," *Zbl. Bakt. Hyg. A* 257: 308–316,1984.

Tapsall and McIver, "β–Glucurondiase Activity Among Prototrophic and Auxotrophic Variants of *Escherichia coli* and Other *Enterobacteriaceae* Commonly Implicated in Urinary Tract Infections," *Diagn. Microbiol. Infect. Dis.* 22: 261–266, 1995.

Wheeler et al., "N–Acetyl–β–glucosaminidase, β–Glucurondiase and Acid Phosphatase in *Mycobacterium leprae,* "*Journal of General Microbiology* 128: 1063–1071 1982.

Wilson et al., *GUS Protocols: Using the GUS Genes as a Reporter of Gene Expression,* Academic Press, Inc., San Diego, 1992 Chapter 1, "The *Escherichia coli gus* Operon: Induction and Expression of the *gus* Operon in *E. coli* and the Occurrence and Use of GUS in Other Bacteria," pp. 7–22.

Wong et al., "Identification of Glu–540 as the Catalytic Nucleophile of Human β–Glucuronidase Using Electrospray Mass Spectrometry," *The Journal of Biological Chemistry* 213(51): 34057–34062, 1998.

Yan et al., "Gene Fusions of Signal Sequences with a Modified β–Glucuronidase Gene Results in Retention of the β–Glucuronidase Protein in the Secretory Pathway/Plasma Membrane," *Plant. Physiol.* 115(3): 915–924, 1997.

\* cited by examiner

FIG. 1A

```
   1 aagcttgagc ggtcatatct gccccaccca cgctcgcgtc ccaatttatt catgacttgc
  61 tgggtaggcg ggaaaaactt ttcggccgct gcttcagtac tctccgcaat gaaaccatgg
 121 gaatgggaag caaccggcaa ctttgacacg tcatgacctg catgagcggc tgccttttta
 181 tagagcctca caagtggctc aaactgcagt gggcggcccc caataatggc tagaactagt
 241 ggcaagccaa gcaggccagc acggatgacg gaatcctgac tgccgccact gccaatccaa
 301 acaggtaaag gatcctgaac aggtcttggg tacacaccga gattctggat ggccggccga
 361 tgtccgcctt tccagttcac cttctcggac tcccgtattt taacaaaag ctccagtttc
 421 tcatcgaata attcatcata gtcttttaaa tcatagccaa acagcggaaa ggattcgata
 481 aaggagcctc gccctgccat aatctctgca cgtccattcg atatggcatc gagggtagca
 541 aaatcctgaa atactcggac tggatcagca agatagaa ccgtcaccgc acttgttaaa
 601 cgaatccgtt ttgtctgcca agcagcggca gccaatagaa ctgctggaga tgatgccgca
 661 aaatcttcgc gatgatgctc accaacacca aagacatcca gcaatacctc gtctgcgagt
 721 acaatttcct caaccacttc ccgaatccgt tgggaatgac tcatcacttc accggtttca
 781 acatccggtg ttgtctctac gaacgtgctt atacctattt ccacaatcat tacctcctat
 841 gtataatcgt ttgctcttgt gccaaagcta tatgaatttc ttattattgc tgacttttttc
 901 accatatata taaatgaaag aatatttcaa acgttattat cttatatttt cctatttatt
 961 tcaaaaaaat tgtttaacta gcgaaagtag gactaccata caaaatgccc atgttgaaca
1021 aaacaaagca ttttttccgc cgttgtttca tacataagaa aggtgcatga ttaagaaatt
1081 ctataaaggc gcaccgagga ggacaatgat gattcaacaa accgttatga ttaacagaga
1141 agcaggttta tatgctcagc cagtcaatca attagtgcaa acagcttcac aattcaatgc
1201 tgatatcttt ctttcataca aggacgaaa ggttagtgtg aaatcggtac tcggcgtttt
1261 atcgttagcg ataccctaaac aggccgaaat tatcttagaa gtttccggag atgatgaaaa
1321 agaagcactc aaaggggtta tcaatgcgtt ggagaaatta gactagggtt ttccctttttt
1381 aatagggaat caccttgaca ttgaaaagt ataagaaaat gaaatagga aaaaccaatg
1441 acttaagggg agtctctatt ggaaagagac tccccttatt caacattaga acgaaattag
1501 agcctttact tttctttcaa cttttcatcc cgatactttt ttgtaatagt ttttttcatt
1561 aataatacaa gtcctgattt tgcaagaata atccttttta gataaaaata tctatgctaa
1621 taataacatg taaccactta catttaaaaa ggagtgctat catgttatat ccaatcaata
1681 cagaaacccg aggagttttt gatttaaatg gggtctggaa ttttaaatta gattacggca
1741 aaggactgga agaaaagtgg tatgaatcaa aactgacaga taccatatca atggctgtac
1801 cttcctccta taatgatatc ggtgttacga aggaaattcg aaaccatatc ggctatgtat
1861 ggtacgagcg tgaatttacc gttcctgctt atttaaaga tcagcgcatc gtcctgcgtt
1921 ttggttcagc aacacataag gctattgtat acgttaacgg agaactagta gttgaacaca
1981 aaggcggctt cttaccgttt gaggcagaaa taaacaacag cttaagagac ggaatgaatc
2041 gtgtaacagt agcggttgat aatatttag atgattctac gctcccagtt gggctatata
2101 gtgaaagaca tgaagaaggt ttgggaaaag tgattcgtaa taaacctaat tttgacttct
2161 ttaactatgc aggcttacat cgtcctgtaa aaatttatac accccttttt acctatgttg
2221 aggatatatc ggttgtaacc gattttaacg gtccaacggg aacagttacg tatacagttg
2281 attttcaggg taaggcagaa accgtaaagg ttagtgtagt tgatgaagaa gggaaagttg
2341 ttgcttcaac tgaaggcctc tctggtaatg ttgagattcc taacgttatc ctttgggaac
2401 ctttaaatac ctatctctat caaattaaag ttgagttagt aaatgatggt ctaactattg
2461 atgtatacga agagccattt ggagttcgaa ccgttgaagt aaacgacggg aaattcctca
2521 ttaataacaa accatttttat tttaagggt tcggaaaaca cgaggatact ccaataaatg
2581 gaagaggctt taatgaagca tcaaatgtaa tggattttaa tattttgaaa tggatcggtg
2641 cgaattcctt tcggacggcg cactatcctt attctgaaga actgatgcgg ctcgcagatc
2701 gtgaagggtt agtcgtcata gatgaaaccc cagcagttgg tgttcatttg aactttatgg
2761 caacgactgg tttgggcgaa ggttcagaga gagtgagtac ttgggaaaaa atccggacct
2821 tgaacatca tcaagatgta ctgagagagc tggtttctcg tgataaaaac caccccctctg
2881 ttgtcatgtg gtcgattgca aatgaagcgg ctacggaaga agaaggcgct tatgaatact
```

FIG. 1B

```
2941 ttaagccatt agttgaatta acgaaagaat tagatccaca aaaacgccca gttaccattg
3001 ttttgttcgt aatggcgaca ccagaaacag ataaagtggc ggagttaatt gatgtgattg
3061 cattgaatcg atacaacggc tggtattttg atggggtga tcttgaagcc gcgaaagtcc
3121 accttcgtca ggaatttcat gcgtggaata aacgctgtcc aggaaaacct ataatgataa
3181 cagagtatgg ggctgatacc gtagctggtt ttcatgatat tgatccggtt atgtttacag
3241 aagagtatca ggttgaatat taccaagcaa atcatgtagt atttgatgaa tttgagaact
3301 ttgttggcga gcaggcctgg aattttgcag actttgctac aagccagggt gtcatgcgtg
3361 ttcaaggtaa caaaaaaggt gttttcacac gcgaccgcaa accaaaatta gcagcacatg
3421 ttttccgcga acgttggaca aacatcccgg atttcggtta taaaaattaa taaaaagctg
3481 gttctccaat aggaggccag cttttttaca tggatacaat ggttgtaaat taaaaaccct
3541 cttcattttt tatataaaaa tgaagagggt tttaatttt taaatgttat tacattttt
3601 ctaagcccac tcatacaata tgggactttg gatagcatgg gaaacagctt ttttagactg
3661 tagttttcca gtcagctgca aattttcaa ttccttggtc tgttaaagga tgttttgata
3721 attgctcaat taccttgaat ggaatcgttg caatatgagc tccagccatc gccacacgtg
3781 taacatgatc tggatgacga acagatgcag caatgatttg tgaatccaag ttttgaatct
3841 ggaacatctt agcaatttt gcgactaatt ctacaccatc ttcgttaata tcatctaacc
3901 tgcctaagaa tggtgaaaca taagttgcac ctgctcgtgc tgccagcaat gcctggttaa
3961 cactaaaaat caaagtaacg ttggttttta cacctttttt cgttagataa cggcaagcct
4021 ctagtccatc taacgtcatc ggaagtttaa ttgtaatatt tttatcgccg ccgttaattt
4081 taatgagctc atttgcttca gcaatcattt gatcagctgt caaagcatta ggtgttactt
4141 cggcagaaac agactcaacc tcgggtacgg cattaaggat ttcagcaata cggtcctcaa
4201 atttcacgcc ctctttagct actaaagaag ggttcgttgt tactcctgat aacacgccaa
4261 ttttataggc ttttttgatt tcctctaggt tggcagtatc gataaaaaat ttcataatgt
4321 ttttcctcca atttttagta aagtaatttt tcgtttctaa agcatgtccc caacgaaat
4381 taggttattg aatataatat aggttacttt ccgttaccat aatataacta tccgacaata
4441 atcgtcaagt aaaatgtctt gaattaaaga tatttatttt tttcaaaaga tactatttac
4501 tttacttat tgataagaat tcacgcatcc taactaggat ggcgtgaatt aactttcctt
4561 attcgacaac tccatctcgt tattgtgagg gagtacttcc tgtttctttt taaatactc
4621 ttgcaaagta ggagggatca tcatagccaa tcgtccaggc gatttcctct acggataaat
4681 tctctgtttt taaaaggtgc ttggcttgct tcattcgtaa tatttgctga aaagcggtta
4741 aggtcatctt tgtttcgtct ttaaattttc gggaaagatg acttggatgg gtagacaatt
4801 gtgctgccaa ttcttcttta ttgatttgct tattataaaa acttagcagg tgttcaatca
4861 ccctttgggt catgtttgta tagctactta atgaattgga aatgattaaa tcgcaatatt
4921 cctcaatcat acaatcttct aattgatgca gtacttctag ttgattagca ttttcgattt
4981 cgtaagcata ttttccgaa attcgatgaa taatgatggc aggtacttgg ctgtttcttg
5041 ctgacgtacg gagaagtatt taatataatc gctacatttt ttagtctgcg caacggctga
5101 ttgggaaatc gttcctaaaa agaaaacagc atattttag aattaatgag ctgtaatgcc
5161 atttttttat ctccacgctc aacggcatgc atgaaatctt ttcagtcttg taccttaatt
5221 tgactagttc cgcttcttca tccacgttaa gatgattcac tttattgtga ataggacggt
5281 tgttttatc agaaacaatg acaaacgggg taatctcttc ctccaacatg tgtggaaact
5341 gctgaaggat gcttgcataa ctgctggcct gttcagcggt tagtacataa attttatcgc
5401 ttataagcat taaatcttca ctttgtggac ttgtgagacg atattccttt gataaactgt
5461 atagattcgg tgtcttatca aaatatggtc cgatgataat ggtgtaggct gcctgctttt
5521 gggtgaagga atatccgaaa tagtgtaagt cccattcgtt tatataagaa tataattggt
5581 cctgatgctt catttttcg aacaaattca gtggatcttc tttctctgaa cctggcataa
5641 atagcgggat tgcaatgatt tcatgatggt acacaaactc cccatttga tctaaaacat
5701 atgtatttaa attggttata tggtggattt tcatagtggt tgagatgatt tttggttgtt
5761 ccatctgatt cctccaattg aactttaaac cataattaaa ttcattttat cctgatattg
5821 ttaaataaat cctaaagaga atcaattgag ttcattatac tagtatcata ttcgcgcttt
5881 caatttaaa ataatgcctt tgttaaactt ggctgttgat ttccgctcca ggtgagtgcg
5941 gttcgcgggc ggtccgggga gcctcctcgg cgctaagcgc ctgtggggtg tcccctgccc
6001 cgtcctcccg caggacattg agtaagctt
```

Bacillus s-GUS Fragment

FIG. 3

```
  1  MLYPINTETR GVFDLNGVWN FKLDYGKGLE EKWYESKLTD
TISMAVPSSY

51  NDIGVTKEIR NHIGYVWYER EFTVPAYLKD QRIVLRFGSA
THKAIVYVNG

101  ELVVEHKGGF LPFEAEINNS LRDGMNRVTV AVDNILDDST
LPVGLYSERH

151  EEGLGKVIRN KPNFDFFNYA GLHRPVKIYT TPFTYVEDIS
VVTDFNGPTG

201  TVTYTVDFQG KAETVKVSVV DEEGKVVAST EGLSGNVEIP
NVILWEPLNT

251  YLYQIKVELV NDGLTIDVYE EPFGVRTVEV NDGKFLINNK
PFYFKGFGKH

301  EDTPINGRGF NEASNVMDFN ILKWIGANSF RTAHYPYSEE
LMRLADREGL

351  VVIDETPAVG VHLNFMATTG LGEGSERVST WEKIRTFEHH
QDVLRELVSR

401  DKNHPSVVMW SIANEAATEE EGAYEYFKPL VELTKELDPQ
KRPVTIVLFV

451  MATPETDKVA ELIDVIALNR YNGWYFDGGD LEAAKVHLRQ
EFHAWNKRCP

501  GKPIMITEYG ADTVAGFHDI DPVMFTEEYQ VEYYQANHVV
FDEFENFVGE

551  QAWNFADFAT SQGVMRVQGN KKGVFTRDRK PKLAAHVFRE
RWTNIPDFGY

```
    MetLeuIleIleThrCysAsnHisLeuHisLeuLysArgSerAlaIle
    ATGCTAATAATAACATGTAACCACTTACATTTAAAAGGAGTGCTATC

MetLeuTyrProIleAsnThrGluThrArgGlyValPheAspLeuAsnGl
  1     ATGTTATATCCAATCAATACAGAAACCCGAGGAGTTTTTGATTTAAATGG yValTrpAsnPheLysLeuAspTyrGlyLysGlyLeuGluGluLysTrpT
 51     GGTCTGGAATTTTAAATTAGATTACGGCAAAGGACTGGAAGAAAAGTGGT yrGluSerLysLeuThrAspThrIleSerMetAlaValProSerSerTyr
101     ATGAATCAAAACTGACAGATACCATATCAATGGCTGTACCTTCCTCCTAT

AsnAspIleGlyValThrLysGluIleArgAsnHisIleGlyTyrValTr
151     AATGATATCGGTGTTACGAAGGAAATTCGAAACCATATCGGCTATGTATG pTyrGluArgGluPheThrValProAlaTyrLeuLysAspGlnArgIleV
201     GTACGAGCGTGAATTTACCGTTCCTGCTTATTTAAAAGATCAGCGCATCG alLeuArgPheGlySerAlaThrHisLysAlaIleValTyrValAsnGly
251     TCCTGCGTTTTGGTTCAGCAACACATAAGGCTATTGTATACGTTAACGGA

GluLeuValValGluHisLysGlyGlyPheLeuProPheGluAlaGluIl
301     GAACTAGTAGTTGAACACAAAGGCGGCTTCTTACCGTTTGAGGCAGAAAT eAsnAsnSerLeuArgAspGlyMetAsnArgValThrValAlaValAspA
351     AAACAACAGCTTAAGAGACGGAATGAATCGTGTAACAGTAGCGGTTGATA snIleLeuAspAspSerThrLeuProValGlyLeuTyrSerGluArgHis
401     ATATTTTAGATGATTCTACGCTCCCAGTTGGGCTATATAGTGAAAGACAT

GluGluGlyLeuGlyLysValIleArgAsnLysProAsnPheAspPhePh
451     GAAGAAGGTTTGGGAAAAGTGATTCGTAATAAACCTAATTTTGACTTCTT eAsnTyrAlaGlyLeuHisArgProValLysIleTyrThrThrProPheT
501     TAACTATGCAGGCTTACATCGTCCTGTAAAAATTTATACAACCCCTTTTA hrTyrValGluAspIleSerValValThrAspPheAsnGlyProThrGly
551     CCTATGTTGAGGATATATCGGTTGTAACCGATTTTAACGGTCCAACGGGA

ThrValThrTyrThrValAspPheGlnGlyLysAlaGluThrValLysVa
601     ACAGTTACGTATACAGTTGATTTTCAGGGTAAGGCAGAAACCGTAAAGGT lSerValValAspGluGluGlyLysValValAlaSerThrGluGlyLeuS
651     TAGTGTAGTTGATGAAGAAGGGAAAGTTGTTGCTTCAACTGAAGGCCTCT
```

FIG. 4B

```
      erGlyAsnValGluIleProAsnValIleLeuTrpGluProLeuAsnThr
701   CTGGTAATGTTGAGATTCCTAACGTTATCCTTTGGGAACCTTTAAATACC

TyrLeuTyrGlnIleLysValGluLeuValAsnAspGlyLeuThrIleAs
751   TATCTCTATCAAATTAAAGTTGAGTTAGTAAATGATGGTCTAACTATTGA pValTyrGluGluProPheGlyValArgThrValGluValAsnAspGlyL
801   TGTATACGAAGAGCCATTTGGAGTTCGAACCGTTGAAGTAAACGACGGGA ysPheLeuIleAsnAsnLysProPheTyrPheLysGlyPheGlyLysHis
851   AATTCCTCATTAATAACAAACCATTTTATTTTAAAGGGTTCGGAAAACAC

GluAspThrProIleAsnGlyArgGlyPheAsnGluAlaSerAsnValMe
901   GAGGATACTCCAATAAATGGAAGAGGCTTTAATGAAGCATCAAATGTAAT tAspPheAsnIleLeuLysTrpIleGlyAlaAsnSerPheArgThrAlaH
951   GGATTTTAATATTTTGAAATGGATCGGTGCGAATTCCTTTCGGACGGCGC isTyrProTyrSerGluGluLeuMetArgLeuAlaAspArgGluGlyLeu
1001  ACTATCCTTATTCTGAAGAACTGATGCGGCTCGCAGATCGTGAAGGGTTA

ValValIleAspGluThrProAlaValGlyValHisLeuAsnPheMetAl
1051  GTCGTCATAGATGAAACCCCAGCAGTTGGTGTTCATTTGAACTTTATGGC aThrThrGlyLeuGlyGluGlySerGluArgValSerThrTrpGluLysI
1101  AACGACTGGTTTGGGCGAAGGTTCAGAGAGAGTGAGTACTTGGGAAAAAA leArgThrPheGluHisHisGlnAspValLeuArgGluLeuValSerArg
1151  TCCGGACCTTTGAACATCATCAAGATGTACTGAGAGAGCTGGTTTCTCGT

AspLysAsnHisProSerValValMetTrpSerIleAlaAsnGluAlaAl
1201  GATAAAAACCACCCCTCTGTTGTCATGTGGTCGATTGCAAATGAAGCGGC aThrGluGluGluGlyAlaTyrGluTyrPheLysProLeuValGluLeuT
1251  TACGGAAGAAGAAGGCGCTTATGAATACTTTAAGCCATTAGTTGAATTAA hrLysGluLeuAspProGlnLysArgProValThrIleValLeuPheVal
1301  CGAAAGAATTAGATCCACAAAAACGCCCAGTTACCATTGTTTTGTTCGTA

MetAlaThrProGluThrAspLysValAlaGluLeuIleAspValIleAl
1351  ATGGCGACACCAGAAACAGATAAAGTGGCGGAGTTAATTGATGTGATTGC aLeuAsnArgTyrAsnGlyTrpTyrPheAspGlyGlyAspLeuGluAlaA
1401  ATTGAATCGATACAACGGCTGGTATTTTGATGGGGTGATCTTGAAGCCG
```

FIG. 4C

```
     laLysValHisLeuArgGlnGluPheHisAlaTrpAsnLysArgCysPro
1451 CGAAAGTCCACCTTCGTCAGGAATTTCATGCGTGGAATAAACGCTGTCCA

GlyLysProIleMetIleThrGluTyrGlyAlaAspThrValAlaGlyPh
1501 GGAAAACCTATAATGATAACAGAGTATGGGGCTGATACCGTAGCTGGTTT eHisAspIleAspProValMetPheThrGluGluTyrGlnValGluTyrT
1551 TCATGATATTGATCCGGTTATGTTTACAGAAGAGTATCAGGTTGAATATT yrGlnAlaAsnHisValValPheAspGluPheGluAsnPheValGlyGlu
1601 ACCAAGCAAATCATGTAGTATTTGATGAATTTGAGAACTTTGTTGGCGAG

GlnAlaTrpAsnPheAlaAspPheAlaThrSerGlnGlyValMetArgVa
1651 CAGGCCTGGAATTTTGCAGACTTTGCTACAAGCCAGGGTGTCATGCGTGT lGlnGlyAsnLysLysGlyValPheThrArgAspArgLysProLysLeuA
1701 TCAAGGTAACAAAAAGGTGTTTTCACACGCGACCGCAAACCAAAATTAG laAlaHisValPheArgGluArgTrpThrAsnIleProAspPheGlyTyr
1751 CAGCACATGTTTTCCGCGAACGTTGGACAAACATCCCGGATTTCGGTTAT

LysAsn
1801 AAAAAT
```

FIG. 5

```
BGUS   ------MLYPINTETRGVFDLNGVWNFKLDYG----KGLEEKWYESKLTDT---ISMAVP   47
HGUS   LGLQGGMLYPQESPSRECKELDGLWSFRADFSDNRRRGFEEQWYRRPLWESGPTVDMPVP   60
EGUS   ------MLRPVETPTREIKKLDGLWAFSLDREN---CGIDQRWWESALQESR---AIAVP   48

BGUS   SSYNDIGVTKEIRNHIGYVWYEREFTVPAYLKD---QRIVLRFGSATHKAIVYVNGELVV  104
HGUS   SSFNDISQDWRLRHFVGWVWYEREVILPERWTQDLRTRVVLRIGSAHSYAIVWVNGVDTL  120
EGUS   GSFNDQFADADIRNYAGNVWYQREVFIPKGWAG---QRIVLRFDAVTHYGKVWVNNQEVM  105

BGUS   EHKGGFLPFEAEINNSLRDG----MNRVTVAVDNILDDSTLPVG-LYSERHEEGLGKVIR  159
HGUS   EHEGGYLPFEADISNLVQVGPLPSRLRITIAINNTLTPTTLPPGTIQYLTDTSKYPKGYF  180
EGUS   EHQGGYTPFEADVTPYVIAG---KSVRITVCVNNELNWQTIPPG--MVITDENGKKK---  157

BGUS   -NKPNFDFFNYAGLHRPVKIYTTPFTYVEDISVVTDFNGPT--GTVTYTVDFQG-KAETV  215
HGUS   VQNTYFDFFNYAGLQRSVLLYTTPTTYIDDITVTTSVEQDS--GLVNYQISVKGSNLFKL  238
EGUS   -QSYFHDFFNYAGIHRSVMLYTTPNTWVDDITVVTHVAQDCNHASVDWQVVANG----DV  212

BGUS   KVSVVDEEGKVVASTEGLSGNVEIPNVILWEP-----LNTYLYQIKVELVNDGLT---ID  267
HGUS   EVRLLDAENKVVANGTGTQGQLKVPGVSLWWPYLMHERPAYLYSLEVQLTAQTSLGPVSD  298
EGUS   SVELRDADQQVVATGQGTSGTLQVVNPHLWQP-----GEGYLYELCVTAKSQTEC----D  263

BGUS   VYEEPFGVRTVEVNDGKFLINNKPFYFKGFGKHEDTPINGRGFNEASNVMDFNILKWIGA  327
HGUS   FYTLPVGIRTVAVTKSQFLINGKPFYFHGVNKHEDADIRGKGFDWPLLVKDFNLLRWLGA  358
EGUS   IYPLRVGIRSVAVKGEQFLINHKPFYFTGFGRHEDADLRGKGFDNVLMVHDHALMDWIGA  323

BGUS   NSFRTAHYPYSEELMRLADREGLVVIDETPAVGVHLNFMATTGLGEGSERVSTWEKIR--  385
HGUS   NAFRTSHYPYAEEVMQMCDRYGIVVIDECPGVGLAL-----------P------QFFNNV  401
EGUS   NSYRTSHYPYAEEMLDWADEHGIVVIDETAAVGFNLSLGIGFEAGNKPKELYSEEAVNGE  383

BGUS   TFEHHQDVLRELVSRDKNHPSVVMWSIANEAATEEEGAYEYFKPLVELTKELDPQKRPVT  445
HGUS   SLHHHMQVMEEVVRRDKNHPAVVMWSVANEPASHLESAGYYLKMVIAHTKSLDPS-RPVT  460
EGUS   TQQAHLQAIKELIARDKNHPSVVMWSIANEPDTRPQGAREYFAPLAEATRKLDPT-RPIT  442

BGUS   IVLFVMATPETDKVAELIDVIALNRYNGWYFDGGDLEAAKVHLRQEFHAWNKRCPGKPIM  505
HGUS   FVS--NSNYAADKGAPYVDVICLNSYYSWYHDYGHLELIQLQLATQFENWYKKYQ-KPII  517
EGUS   CVNVMFCDAHTDTISDLFDVLCLNRYYGWYVQSGDLETAEKVLEKELLAWQEKLH-QPII  501

BGUS   ITEYGADTVAGFHDIDPVMFTEEYQVEYYQANHVVFD--EFENFVGEQAWNFADFATSQG  563
HGUS   QSEYGAETIAGFHQDPPLMFTEEYQKSLLEQYHLGLDQKRRKYVVGELIWNFADFMTEQS  577
EGUS   ITEYGVDTLAGLHSMYTDMWSEEYQCAWLDMYHRVFD--RVSAVVGEQVWNFADFATSQG  559

BGUS   VMRVQGNKKGVFTRDRKPKLAAHVFRERWTNIPDFGYKN-----  602
HGUS   PTRVLGNKKGIFTRQRQPKSAAFLLRERYWKIAN-ET-------  613
EGUS   ILRVGGNKKGIFTRDRKPKSAAFLLQKRWTGMNFGEKPQQGGKQ  603
```

*BoGUS* is not substantially inhibited by detergents

- ☐ CONTROL
- ▨ SDS 0.1%
- ■ SDS 0.5%
- ■ SDS 1.0%
- ☐ Triton X-100 0.1%
- ■ Triton X-100 0.5%
- ■ Triton X-100 1.0%
- ☐ Sarcosyl 0.1%
- ■ Sarcosyl 0.5%
- ☐ Sarcosyl 1.0%

```
                              M   V   D   L   T   S   L   Y
                    SalI  NcoI    BglII
                    ~~~~~~~~~~~~  ~~~~~~
2451  ATACGACTCA CTAGTGGGTC GACCCATGGT AGATCTGACT AGTCTGTACC
      TATGCTGAGT GATCACCCAG CTGGGTACCA TCTAGACTGA TCAGACATGG

+1 P   I   N   T   E   T   R   G   V   F   D   L   N   G   V   W   N
2501  CGATCAACAC CGAGACCCGT GGCGTCTTCG ACCTCAATGG CGTCTGGAAC
      GCTAGTTGTG GCTCTGGGCA CCGCAGAAGC TGGAGTTACC GCAGACCTTG

+1  F   K   L   D   Y   G   K   G   L   E   E   K   W   Y   E   S   K
2551  TTCAAGCTGG ACTACGGGAA AGGACTGGAA GAGAAGTGGT ACGAAAGCAA
      AAGTTCGACC TGATGCCCTT TCCTGACCTT CTCTTCACCA TGCTTTCGTT

+1   L   T   D   T   I   S   M   A   V   P   S   S   Y   N   D   I
2601  GCTGACCGAC ACTATTAGTA TGGCCGTCCC AAGCAGTTAC AATGACATTG
      CGACTGGCTG TGATAATCAT ACCGGCAGGG TTCGTCAATG TTACTGTAAC

+1 G   V   T   K   E   I   R   N   H   I   G   Y   V   W   Y   E   R
2651  GCGTGACCAA GGAAATCCGC AACCATATCG GATATGTCTG GTACGAACGT
      CGCACTGGTT CCTTTAGGCG TTGGTATAGC CTATACAGAC CATGCTTGCA

+1  E   F   T   V   P   A   Y   L   K   D   Q   R   I   V   L   R   F
2701  GAGTTCACGG TGCCGGCCTA TCTGAAGGAT CAGCGTATCG TGCTCCGCTT
      CTCAAGTGCC ACGGCCGGAT AGACTTCCTA GTCGCATAGC ACGAGGCGAA

+1    G   S   A   T   H   K   A   I   V   Y   V   N   G   E   L   V
2751  CGGCTCTGCA ACTCACAAAG CAATTGTCTA TGTCAATGGT GAGCTGGTCG
      GCCGAGACGT TGAGTGTTTC GTTAACAGAT ACAGTTACCA CTCGACCAGC

+1 V   E   H   K   G   G   F   L   P   F   E   A   E   I   N   N   S
2801  TGGAGCACAA GGGCGGATTC CTGCCATTCG AAGCGGAAAT CAACAACTCG
      ACCTCGTGTT CCCGCCTAAG GACGGTAAGC TTCGCCTTTA GTTGTTGAGC

+1  L   R   D   G   M   N   R   V   T   V   A   V   D   N   I   L   D
2851  CTGCGTGATG GCATGAATCG CGTCACCGTC GCCGTGGACA ACATCCTCGA
      GACGCACTAC CGTACTTAGC GCAGTGGCAG CGGCACCTGT TGTAGGAGCT

+1   D   S   T   L   P   V   G   L   Y   S   E   R   H   E   E   G
2901  CGATAGCACC CTCCCGGTGG GGCTGTACAG CGAGCGCCAC GAAGAGGGCC
      GCTATCGTGG GAGGGCCACC CCGACATGTC GCTCGCGGTG CTTCTCCCGG

+1 L   G   K   V   I   R   N   K   P   N   F   D   F   F   N   Y   A
2951  TCGGAAAAGT CATTCGTAAC AAGCCGAACT TCGACTTCTT CAACTATGCA
      AGCCTTTTCA GTAAGCATTG TTCGGCTTGA AGCTGAAGAA GTTGATACGT

+1  G   L   H   R   P   V   K   I   Y   T   T   P   F   T   Y   V   E
3001  GGCCTGCACC GTCCGGTGAA AATCTACACG ACCCCGTTTA CGTACGTCGA
      CCGGACGTGG CAGGCCACTT TTAGATGTGC TGGGGCAAAT GCATGCAGCT

+1   D   I   S   V   V   T   D   F   N   G   P   T   G   T   V   T
3051  GGACATCTCG GTTGTGACCG ACTTCAATGG CCCAACCGGG ACTGTGACCT
      CCTGTAGAGC CAACACTGGC TGAAGTTACC GGGTTGGCCC TGACACTGGA
```

FIG. 13B

```
      +1  Y   T   V   D   F   Q   G   K   A   E   T   V   K   V   S   V   V
    3101  ATACGGTGGA CTTTCAAGGC AAAGCCGAGA CCGTGAAAGT GTCGGTCGTG
          TATGCCACCT GAAAGTTCCG TTTCGGCTCT GGCACTTTCA CAGCCAGCAC

+1  D   E   E   G   K   V   V   A   S   T   E   G   L   S   G   N   V
    3151  GATGAGGAAG GCAAAGTGGT CGCAAGCACC GAGGGCCTGA GCGGTAACGT
          CTACTCCTTC CGTTTCACCA GCGTTCGTGG CTCCCGGACT CGCCATTGCA

+1  E   I   P   N   V   I   L   W   E   P   L   N   T   Y   L   Y
    3201  GGAGATTCCG AATGTCATCC TCTGGGAACC ACTGAACACG TATCTCTACC
          CCTCTAAGGC TTACAGTAGG AGACCCTTGG TGACTTGTGC ATAGAGATGG

+1 Q   I   K   V   E   L   V   N   D   G   L   T   I   D   V   Y   E
    3251  AGATCAAAGT GGAACTGGTG AACGACGGAC TGACCATCGA TGTCTATGAA
          TCTAGTTTCA CCTTGACCAC TTGCTGCCTG ACTGGTAGCT ACAGATACTT

+1  E   P   F   G   V   R   T   V   E   V   N   D   G   K   F   L   I
    3301  GAGCCGTTCG GCGTGCGGAC CGTGGAAGTC AACGACGGCA AGTTCCTCAT
          CTCGGCAAGC CGCACGCCTG GCACCTTCAG TTGCTGCCGT TCAAGGAGTA

+1  N   N   K   P   F   Y   F   K   G   F   G   K   H   E   D   T
    3351  CAACAACAAA CCGTTCTACT TCAAGGGCTT TGGCAAACAT GAGGACACTC
          GTTGTTGTTT GGCAAGATGA AGTTCCCGAA ACCGTTTGTA CTCCTGTGAG

+1 P   I   N   G   R   F   N   E   A   S   N   V   M   D   F   N
    3401  CTATCAACGG CCGTGGCTTT AACGAAGCGA GCAATGTGAT GGATTTCAAT
          GATAGTTGCC GGCACCGAAA TTGCTTCGCT CGTTACACTA CCTAAAGTTA

+1  I   L   K   W   I   G   A   N   S   F   R   T   A   H   Y   P   Y
    3451  ATCCTCAAAT GGATCGGCGC CAACAGCTTC CGGACCGCAC ACTATCCGTA
          TAGGAGTTTA CCTAGCCGCG GTTGTCGAAG GCCTGGCGTG TGATAGGCAT

+1  S   E   E   L   M   R   L   A   D   R   E   G   L   V   V   I
    3501  CTCTGAAGAG TTGATGCGTC TTGCGGATCG CGAGGGTCTG GTCGTGATCG
          GAGACTTCTC AACTACGCAG AACGCCTAGC GCTCCCAGAC CAGCACTAGC

+1 D   E   T   P   A   V   G   V   H   L   N   F   M   A   T   T   G
    3551  ACGAGACTCC GGCAGTTGGC GTGCACCTCA ACTTCATGGC CACCACGGGA
          TGCTCTGAGG CCGTCAACCG CACGTGGAGT TGAAGTACCG GTGGTGCCCT

+1  L   G   E   G   S   E   R   V   S   T   W   E   K   I   R   T   F
    3601  CTCGGCGAAG GCAGCGAGCG CGTCAGTACC TGGGAGAAGA TTCGGACGTT
          GAGCCGCTTC CGTCGCTCGC GCAGTCATGG ACCCTCTTCT AAGCCTGCAA

+1  E   H   H   Q   D   V   L   R   E   L   V   S   R   D   K   N
    3651  TGAGCACCAT CAAGACGTTC TCCGTGAACT GGTGTCTCGT GACAAGAACC
          ACTCGTGGTA GTTCTGCAAG AGGCACTTGA CCACAGAGCA CTGTTCTTGG

+1  H   P   S   V   M   W   S   I   A   N   E   A   A   T   E   E
    3701  ATCCAAGCGT CGTGATGTGG AGCATCGCCA ACGAGGCGGC GACTGAGGAA
          TAGGTTCGCA GCACTACACC TCGTAGCGGT TGCTCCGCCG CTGACTCCTT

+1  E   G   A   Y   E   Y   F   K   P   L   V   E   L   T   K   E   L
    3751  GAGGGCGCGT ACGAGTACTT CAAGCCGTTG GTGGAGCTGA CCAAGGAACT
          CTCCCGCGCA TGCTCATGAA GTTCGGCAAC CACCTCGACT GGTTCCTTGA
```

FIG. 13C

```
     +1    D   P   Q   K   R   P   V   T   I   V   L   F   V   M   A   T
3801       CGACCCACAG AAGCGTCCGG TCACGATCGT GCTGTTTGTG ATGGCTACCC
           GCTGGGTGTC TTCGCAGGCC AGTGCTAGCA CGACAAACAC TACCGATGGG

+1 P   E   T   D   K   V   A   E   L   I   D   V   I   A   L   N   R
3851       CGGAGACGGA CAAAGTCGCC GAACTGATTG ACGTCATCGC GCTCAATCGC
           GCCTCTGCCT GTTTCAGCGG CTTGACTAAC TGCAGTAGCG CGAGTTAGCG

+1    Y   N   G   W   Y   F   D   G   G   D   L   E   A   A   K   V   H
3901       TATAACGGAT GGTACTTCGA TGGCGGTGAT CTCGAAGCGG CCAAAGTCCA
           ATATTGCCTA CCATGAAGCT ACCGCCACTA GAGCTTCGCC GGTTTCAGGT

+1    L   R   Q   E   F   H   A   W   N   K   R   C   P   G   K   P
3951       TCTCCGCCAG GAATTTCACG CGTGGAACAA GCGTTGCCCA GGAAAGCCGA
           AGAGGCGGTC CTTAAAGTGC GCACCTTGTT CGCAACGGGT CCTTTCGGCT

+1 I   M   I   T   E   Y   G   A   D   T   V   A   G   F   H   D   I
4001       TCATGATCAC TGAGTACGGC GCAGACACCG TTGCGGGCTT TCACGACATT
           AGTACTAGTG ACTCATGCCG CGTCTGTGGC AACGCCCGAA AGTGCTGTAA

+1    D   P   V   M   F   T   E   E   Y   Q   V   E   Y   Y   Q   A   N
4051       GATCCAGTGA TGTTCACCGA GGAATATCAA GTCGAGTACT ACCAGGCGAA
           CTAGGTCACT ACAAGTGGCT CCTTATAGTT CAGCTCATGA TGGTCCGCTT

+1    H   V   V   F   D   E   F   E   N   F   V   G   E   Q   A   W
4101       CCACGTCGTG TTCGATGAGT TTGAGAACTT CGTGGGTGAG CAAGCGTGGA
           GGTGCAGCAC AAGCTACTCA AACTCTTGAA GCACCCACTC GTTCGCACCT

+1 N   F   A   D   F   A   T   S   Q   G   V   M   R   V   Q   G   N
4151       ACTTCGCGGA CTTCGCGACC TCTCAGGGCG TGATGCGCGT CCAAGGAAAC
           TGAAGCGCCT GAAGCGCTGG AGAGTCCCGC ACTACGCGCA GGTTCCTTTG

+1    K   K   G   V   F   T   R   D   R   K   P   K   L   A   A   H   V
4201       AAGAAGGGCG TGTTCACTCG TGACCGCAAG CCGAAGCTCG CCGCGCACGT
           TTCTTCCCGC ACAAGTGAGC ACTGGCGTTC GGCTTCGAGC GGCGCGTGCA

+1    F   R   E   R   W   T   N   I   P   D   F   G   Y   K   N
                                                              NheI
                                                              ~~~~
4251       CTTTCGCGAG CGCTGGACCA ACATTCCAGA TTTCGGCTAC AAGAACGCTA
           GAAAGCGCTC GCGACCTGGT TGTAAGGTCT AAAGCCGATG TTCTTGCGAT

NheI            PmlI            BstEII
           ~~              ~~~~~~~         ~~~~~~~
4301       GCCATCACCA TCACCATCAC GTGTGAATTG GTGACCG
           CGGTAGTGGT AGTGGTAGTG CACACTTAAC CACTGGC
```

MICROBIAL β-GLUCURONIDASE GENES, GENE PRODUCTS AND USES THEREOF

CROSS-REFERENCE TO RELATED APPLICATION

This application claims priority to Divisional Ser. No. 08/882,704 filed Jun. 25, 1997 now U.S. Pat. No. 5,879,906.

This application claims the benefit of U.S. Provisional Application No. 60/058,263, filed Sep. 9, 1997, which application is incorporated by reference in its entirety.

TECHNICAL FIELD

The present invention relates generally to forms of microbial β-glucuronidase that are directed to specific cell compartments, and more specifically to a secreted form of β-glucuronidase and uses of these β-glucuronidases thereof.

BACKGROUND OF THE INVENTION

The natural habitat of *E. coli* is the gut, and the β-glucuronidase (GUS) activity of *E. coli* plays a specific and very important role in its natural history. The gut is a rich source of glucuronic acid compounds, providing a carbon source that can be efficiently exploited by *E. coli*. Glucuronide substrates are taken up by *E. coli* via a specific transporter, the glucuronide permease (U.S. Pat. Nos. 5,288, 463 and 5,432,081), and cleaved by β-glucuronidase. The glucuronic acid residue thus released is used as a carbon source. In general, the aglycon component of the glucuronide substrate is not used by *E. coli* and passes back across the bacterial membrane into the gut to be reabsorbed into the bloodstream and undergo glucuronidation in the liver, which begins the cycle again.

In *E. coli*, β-glucuronidase is encoded by the gusA gene (Novel and Novel *Mol. Gen. Genet.* 120:319–335, 1973), which is one member of an operon comprising three protein-encoding genes. The second gene, gusB, encodes a specific permease (PER) for β-glucuronides. The third gene, gusC, encodes an outer membrane protein (MOP) of approximately 50 kDa that facilitates access of glucuronides to the permease located in the inner membrane. The principle repressor for the GUS operon, gusR, maps immediately upstream of the operon.

β-glucuronidase activity is expressed in almost all tissues of all vertebrates and many mollusks (Levvy and Conchie, 1966). In addition, the free-living soil nematode, *Caenorhabditis elegans*, has an endogenous β-glucuronidase activity (Sebastiani et al, 1987; Jefferson et al, 1987), which occurs at low levels in the intestine of the worm. The enzyme has been purified from many mammalian sources (e.g. Tomino et al, 1975) and forms a homotetrameric structure with a subunit molecular weight of approximately 70 kDa.

The vertebrate enzyme is synthesized with a signal sequence at the amino terminus, then transported to and glycosylated within the endoplasmic reticulum, and ultimately localized intracellularly within vacuoles. If any of the mammalian enzyme is secreted, it probably contributes little to the total activity as the enzyme is relatively unstable. Thus, for use in medical diagnostics (e.g., drug testing) and transgenic constructions, the *E. coli* enzyme is preferred because it is much more active and stable than the mammalian enzyme against most biosynthetically derived β-glucuronides (Tomasic and Keglevic, 1973; Levvy and Conchie, 1966).

Production of GUS for use in in vitro assays, such as medical diagnostics, is costly and requires extensive manipulation as GUS must be recovered from cell lysates. A secreted form of GUS would reduce manufacturing expenses, however, attempts to cause secretion have been unsuccessful. In addition, for use in transgenics, the current GUS system has somewhat limited utility because enzymatic activity is detected intracellularly by deposition of toxic calorimetric products during the staining or detection of GUS. Moreover, in cells that do not express a glucuronide permease, the cells must be permeabilized or sectioned for introduction of the substrate. Thus, this conventional staining procedure generally results in the destruction of the stained cells. In light of this limitation, a secreted GUS would allow for development of non-destructive marker system, especially useful for agricultural field work.

The present invention provides gene and protein sequences of secreted β-glucuronide, variants thereof, and use of the protein as a transformation marker, while providing other related advantages.

SUMMARY OF THE INVENTION

In one aspect, an isolated nucleic acid molecule is provided comprising a nucleic acid sequence encoding a secreted form of β-glucuronidase, wherein the nucleic acid sequence comprises the amino acid sequence as presented in FIG. 3 SEQ ID No: 2 or hybridizes under stringent conditions to the complement of the sequence comprising nucleotides 1662–3467 of FIG. 1 SEQ ID No: 1 and which encodes a functional β-glucuronidase. In preferred embodiments, the nucleic acid molecule comprises nucleotides 1662–3467 of FIG. 1 SEQ ID No: 1 or encodes the amino acid sequence of FIG. 3, SEQ ID No: 2 or a variant thereof.

In another aspect, the invention provides an isolated secreted form of β-glucuronidase, wherein β-glucuronidase is encoded by the isolated nucleic acid molecule or by a nucleic acid molecule that hybridizes under stringent conditions to the complement of nucleotides 1662–3467 of FIG. 1 SEQ ID No: 1 and which encodes a functional β-glucuronidase. In a preferred embodiment, the isolated secreted form of β-glucuronidase comprises the amino acid sequence of FIG. 3, SEQ ID No: 2 or a variant thereof.

The invention also provides vectors and host cells, comprising a nucleic acid molecule encoding a secreted form of β-glucuronidase, wherein the β-glucuronidase sequence is in operative linkage with a promoter element. In preferred embodiments, the promoter element is a promoter derived from a plant pathogen. Preferred host cells are selected from the group consisting of a plant cell, an insect cell, a fungal cell, an animal cell and a bacterial cell.

The invention also provides a method of producing a secreted form of β-glucuronidase, comprising: (a) introducing a vector comprising a nucleic acid molecule encoding a microbial β-glucoronidase into a host cell, wherein the vector comprises nucleic acid sequence encoding the β-glucuronidase is expressed. The method may further comprise isolating the β-glucuronidase from cell supernatant or periplasm.

In other aspects, the invention provides methods of introducing a controller element into a host cell, monitoring expression of a gene of interest or a portion thereof in a host cell, monitoring activity of a controller element in a host cell, transforming a host cell with a gene of interest or portion thereof, and positive selection for a transformed cell.

In other aspects, transgenic cells are provided, such as plant cells, insect cells, and transgenic plants and insects.

In other aspects, kits comprising microbial GUS are provided.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIGS. 1A & 1B (SEQ ID No: 1) is DNA sequence of an approximately 6 kb fragment that encodes β-glucuronidase from Bacillus.

FIG. 3 (SEQ ID No: 2) is an amino acid sequence of Bacillus GUS.

FIGS. 4A–4C (SEQ ID No: 3–4) is a DNA sequence of Bacillus GUS with the predicted amino acid translation.

FIG. 5 presents amino acid alignments of Bacillus GUS (BGUS) (SEQ ID No: 2) $E.$ $coli$ GUS (EGUS) (SEQ ID No: 6) and (human GUS (HGUS) (SEQ ID No: 5).

FIG. 10 is a graph presenting relative enzyme activity of Baeillvs GUS in various detergents.

FIGS. 13A–13C (SEQ ID No: 8, amino acid sequence; SEQ ID NO: 7, upper DNA sequence, SEQ ID No: 9, lower DNA sequence) is a DNA sequence of Bacillus GUS that is codon optimized for production in $E.$ $coli.$

DETAILED DESCRIPTION OF THE INVENTION

Figure 2:
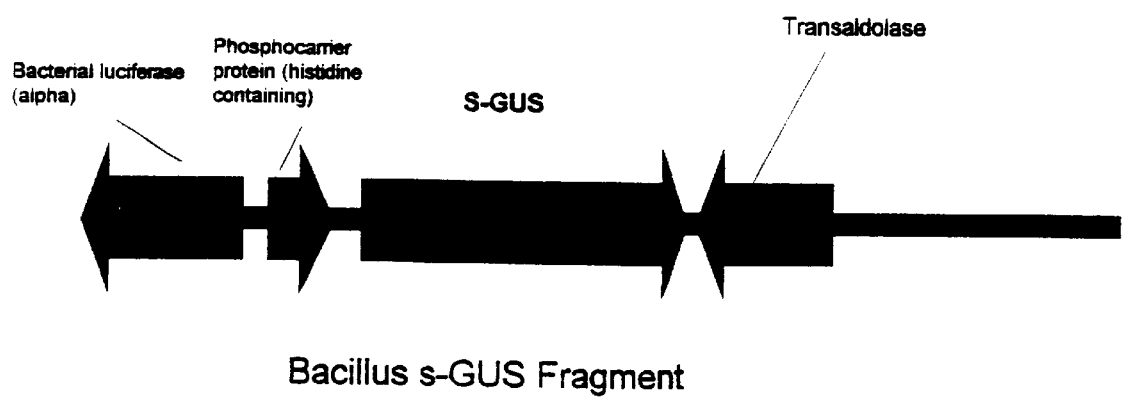
FIG. 2 is a schematic of the DNA sequence of a Bacillus 6 kb fragment showing the location and orientation of the major open reading frames. S-GUS is β-glucuronidase.

Prior to setting forth the invention, it may be helpful to an understanding thereof to set forth definitions of certain terms that will be used hereinafter.

As used herein, "β-glucuronidase" refers to an enzyme that catalyzes the hydrolysis of β-glucuronides. For assays to detect β-glucuronidase activity, fluorogenic or chromogenic substrates are preferred. Such substrates include, but are not limited to, p-nitrophenyl β-D-glucuronide and 4-methylumbelliferyl β-D-glucuronide. Assays and some exemplary substrates for determining β-glucuronidase activity, also known as GUS activity, are provided in U.S. Pat. No. 5,268,463.

As used herein, a "secreted form of a microbial β-glucuronidase" refers to a microbial β-glucuronidase that is capable of being localized to an extracellular environment of a cell, including extracellular fluids, periplasm, or membrane bound on the external face of a cell but not bound as an integral membrane protein. Some of the protein may be found intracellularly. Thus, secreted microbial GUS encompasses GUS proteins that are secreted in $E.$ $coli$ statistically significantly more than EcGUS ($E.$ $coli$ GUS). The amino acid and nucleotide sequences of an exemplary secreted β-glucuronidase are presented in FIGS. 4A–C, SEQ ID Nos: 3 and 4. Secreted microbial GUS also encompasses variants of β-glucuronidase. A variant may be a portion of the secreted β-glucuronidase and/or have amino acid substitutions, insertions, and deletions, either found naturally as a polymorphic allele or constructed.

As used herein, "percent sequence identity" is a percentage determined by the number of exact matches of amino acids or nucleotides to a reference sequence divided by the number of residues in the region of overlap. Within the context of this invention, preferred amino acid sequence identity for a variant is at least 75% and preferably greater than 80%, 85%, 90% or 95%. A nucleotide variant will typically be sufficiently similar in sequence to hybridize to the reference sequence under stringent hybridization conditions (for nucleic acid molecules over about 500 bp, conditions include a solution comprising about 1 M Na+ at 250 to 30° C. below the Tm; e.g., 5×SSPE, 0.5% SDS, at 65° C.; see, Ausubel, et al., $Current$ $Protocols$ $in$ $Molecular$ $Biology$, Greene Publishing, 1995; Sambrook et al., $Molecular$ $Cloning$: $A$ $Laboratory$ $Manual$, Cold Spring Harbor Press, 1989). Some variants may not hybridize to the reference sequence because of codon degeneracy, such as introduced for codon optimization in a particular host, in which case amino acid identity may be used to assess similarity of the variant to the reference protein.

As used herein, a "glucuronide" or "β-glucuronide" refers to an aglycon conjugated in a hemiacetal linkage, typically through the hydroxyl group, to the C1 of a free D-glucuronic acid in the β configuration. β-glucuronides consist of virtually any compound linked to the 1-position of glucuronic acid as a beta anomer, and, are typically, though by no means exclusively, found as the -O-glycoside. β-glucuronides are produced naturally in most vertebrates through the action of UDP-glucuronyl transferase as a part of the process of solubilizing, detoxifying, and mobilizing both natural and xenobiotic compounds, thus directing them to sites of excretion or activity through the circulatory system.

β-glucuronides in polysaccharide form are also common in nature, most abundantly in vertebrates, where they are major constituents of connective and lubricating tissues in polymeric form with other sugars such as N-acetylglucosamine (e.g., chondroitan sulfate, of cartilage, and hyaluronic acid, which is the principle constituent of synovial fluid and mucus). β-glucuronides are relatively uncommon or absent in plants. Glucuronides and galacturonides found in plant cell wall components (such as pectin) are generally in the alpha configuration, and are frequently substituted as the 4-O-methyl ether; hence, such glucuronides are not substrates for β-glucuronidase.

An "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, or some combination of these.

Microbial Glucuronidase Genes and Gene Products

As noted above, this invention provides gene sequences and gene products for secreted forms of microbial β-glucuronidase. Such β-glucuronidase genes may be isolated by a variety of methods, including genetic, biochemical, or immunological procedures. As exemplified herein, a gene from a Bacillus encoding a secreted β-glucuronidase was identified biochemically and by DNA sequence analysis. Secreted microbial β-glucuronidases from other organisms may be identified biochemically as described herein or by hybridization of the Bacillus β-glucuronidase gene sequence with genomic or cDNA libraries, by genetic complementation, by function, or by antibody screening of an expression library (see Sambrook et al., infra Ausubel et al, infra for methods and conditions appropriate for isolation of a β-glucuronidase from other species). Merely as an example, the isolation of Bacillus β-glucuronidase gene and gene products are provided herein.

The existence of a secreted form of β-glucuronidase may be observed by biochemical screening of samples containing microbes, such as those isolated from soil, animal or human skin, saliva, mucous, or feces, water, and the like. Colonies are plated, and a glucuronide substrate is added that is readily detectable when cleaved by β-glucuronidase. A microbe that secretes β-glucuronidase will exhibit a diffuse staining pattern surrounding the colony. A complementation assay may be performed to verify that the staining pattern is due to a secreted GUS. In this assay, the candidate secreted GUS gene is transfected into an $E.$ $coli$ strain that is deleted for the GUS operon (e.g., KW1 described herein), and the staining pattern of the transfectant is compared to a mock-transfected host. The transfectant should exhibit a diffuse staining pattern surrounding the colony, whereas, the host will not.

In an exemplary screen, a bacterial colony isolated from a soil sample displayed a strong, diffuse staining pattern. The bacterium was identified as a Bacillus by sequence determination of 16S rRNA after amplification. A genomic library from this Bacillus was constructed in the vector pBSII KS+. The recombinant plasmids were transfected into KW1, a strain deleted for the β-glucuronidase operon. One resulting colony, pRAJa17.1, exhibited a strong, diffuse staining pattern similar to the Bacillus.

The DNA sequence of the insert of pRAJa17.1 is presented in FIG. 1 and as SEQ ID No: 1. A schematic of the insert is presented in FIG. 2. The β-glucuronidase gene contained in the insert was identified by similarity of the predicted amino acid sequence of an open reading frame (FIG. 3; SEQ ID No: 2) to the $E.$ $coli$ and human β-glucuronidase amino acid sequences (FIG. 5, Human GUS: HGUS SEQ ID No: 5; $E.$ $coli$ GUS: EGUS, SEQ ID No: 6). Overall, Bacillus β-glucuronidase has approximately 47–49% amino acid identity to $E.$ $coli$ GUS and to human GUS. An open reading frame of Bacillus GUS is 1854 bases, which would result in a protein that is 618 amino acids in length. The first methionine codon however, is unlikely to encode the initiator methionine. Rather the second methionine codon, at codon 16, is most likely the initiator methionine. Such a translated product is 602 amino acids long and is the sequence presented in FIG. 3 (SEQ ID No: 2). The assignment of the initiator methionine is based upon a consensus Shine-Dalgarno sequence found upstream of the second Met, but not the first Met, and alignment of the Bacillus, human and $E.$ $coli$ GUS amino acid sequences. Furthermore, as shown herein, Bacillus GUS gene lacking sequence encoding the 16 amino acids is expressed in $E.$ $coli$ transfectants. In addition, the 16 amino acids (Met-Leu-Ile-Ile-Thr-Cys-Asn-His-Leu-His-Leu-Lys-Arg-Ser-Ala-Ile (SEQ ID No: 10)) do not exhibit a consensus signal peptide sequence.

There is a single Asn-Asn-Ser sequence (residues 128–130 in FIG. 3 SEQ ID No: 2) that can serve as a site for N-linked carbohydrates. Furthermore, unlike the $E.$ $coli$ and human β-glucuronidases, which have 9 and 4 cysteines respectively, the Bacillus protein has only a single Cys residue (residue 499 in FIG. 3).

Figure 11:
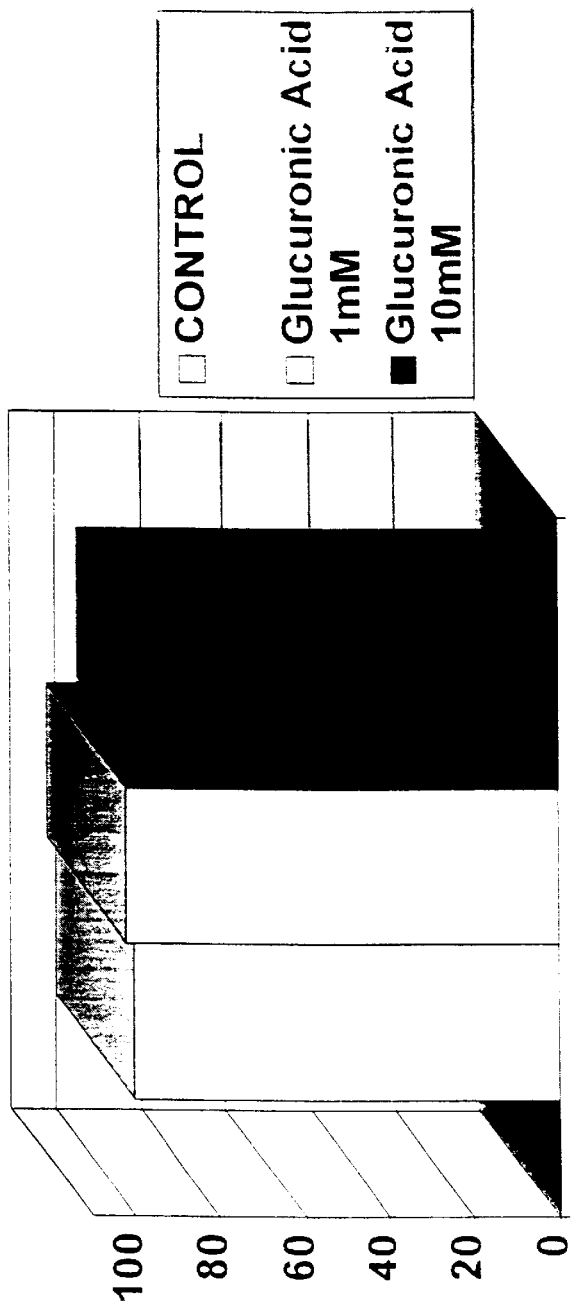
FIG. 11 is a graph presenting relative enzyme activity of Bacillus GUS in the presence of glucuronic acid.
Figure 12:
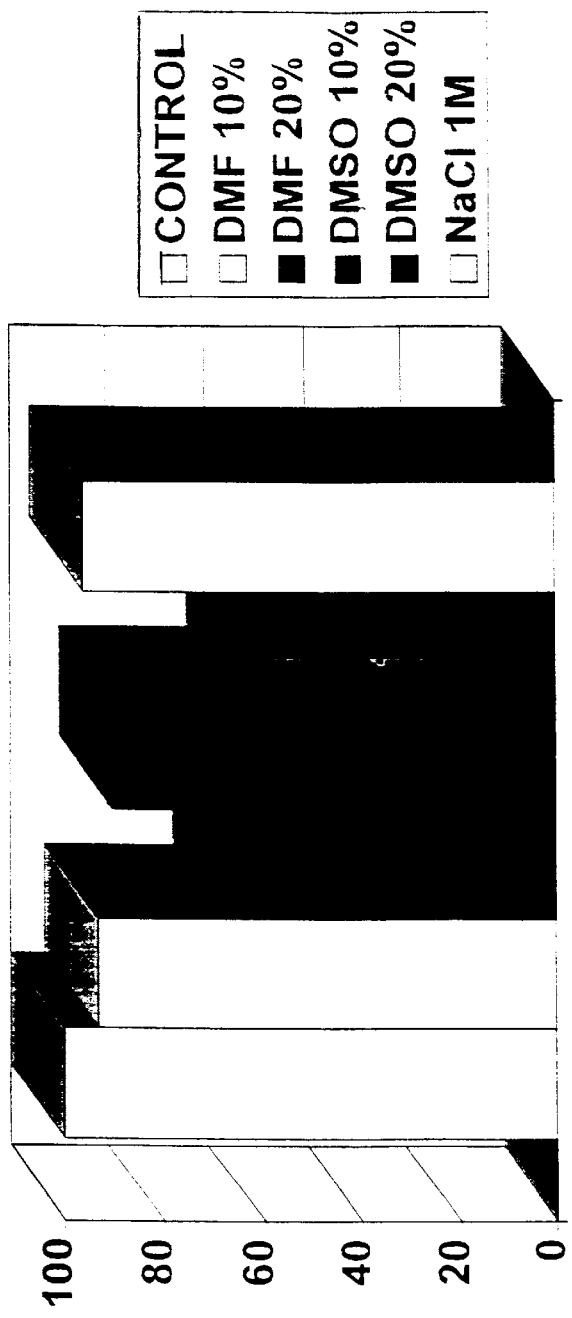
FIG. 12 is a graph presenting relative enzyme activity of Bacillus GUS in various organic solvents and in salt.

The Bacillus β-glucuronidase is secreted in $E.$ $coli$ when introduced in an expression plasmid as evidenced by approximately half of the enzyme activity being detected in the periplasm. In contrast, less than 10% of $E.$ $coli$ β-glucuronidase is found in periplasm. Secreted microbial GUS is also more stable than $E.$ $coli$ GUS (FIG. 7), has a higher turnover number at both 37° C. and room temperature (FIGS. 8 and 9), and unlike $E.$ $coli$ GUS, it is not substantially inhibited by detergents (FIG. 10) or by glucuronic acid (FIG. 11) and retains activity in high salt conditions and organic solvents (FIG. 12).

In certain aspects, variants of secreted microbial GUS are useful within the context of this invention. Variants include nucleotide or amino acid substitutions, deletions, insertions, and chimeras. Typically, when the result of synthesis, amino acid substitutions are conservative, ie., substitution of amino acids within groups of polar, non-polar, aromatic, charged, etc. amino acids. As will be appreciated by those skilled in the art, a nucleotide sequence encoding microbial GUS may differ from the wild-type sequence presented in the FIG.s; due to codon degeneracies, nucleotide polymorphisms, or amino acid differences. In certain embodiments, variants preferably hybridize to the wild-type nucleotide sequence at conditions of normal stringency, which is approximately 25–30° C. below Tm of the native duplex (e.g., 1 M Na+ at 65° C.; e.g. 5×SSPE, 0.5% SDS, 5×Denhardt's solution, at 65° C. or equivalent conditions; see generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987). Alternatively, the Tm for other than short oligonucleotides can be calculated by the formula Tm=81.5+0.41%(G+C)−log(Na+). Low stringency hybridizations are performed at conditions approximately 40° C. below Tm, and high stringency hybridizations are performed at conditions approximately 10° C. below Tm.

Variants may be constructed by any of the well known methods in the art (see, generally, Ausubel et al., supra; Sambrook et al., supra). Such methods include site-directed oligonucleotide mutagenesis, restriction enzyme digestion and removal or insertion of bases, amplification using primers containing mismatches or additional nucleotides, splicing of another gene sequence to the reference microbial GUS gene, and the like. Briefly, preferred methods for generating a few nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. Similarly, deletions and/or insertions may be constructed by any of a variety of known methods. For example, the gene can be digested with restriction enzymes and religated such that some sequence is deleted or ligated with an isolated fragment having cohesive ends so that an insertion or large substitution is made. In another embodiment, variants are generated by shuffling of regions (see U.S. Pat. No. 5,605,793). Variant sequences may also be generated by "molecular evolution" techniques (see U.S. Pat. No. 5,723, 323). Other means to generate variant sequences may be found, for example, in Sambrook et al. (supra) and Ausubel et al. (supra). Verification of variant sequences is typically accomplished by restriction enzyme mapping, sequence analysis, or probe hybridization, although other methods may be used. The double-stranded nucleic acid is transformed into host cells, typically *E. coli*, but alternatively, other prokaryotes, yeast, or larger eukaryotes may be used. Standard screening protocols, such as nucleic acid hybridization, amplification, and DNA sequence analysis, will identify mutant sequences.

In addition to directed mutagenesis in which one or a few amino acids are altered, variants that have multiple substitutions may be generated. The substitutions may be scattered throughout the protein or functional domain or concentrated in a small region. For example, a region may be mutagenized by oligonucleotide-directed mutagenesis in which the oligonucleotide contains a string of dN bases or the region is excised and replaced by a string of dN bases. Thus, a population of variants with a randomized amino acid sequence in a region is generated. The variant with the desired properties (e.g., more efficient secretion) is then selected from the population.

As shown herein, multiple mutations at residues Val 128, Leu 141, Tyr 204 and Thr 560 (FIG. 3 SEQ ID No: 2) result in a non-functional enzyme. Thus, at least one of these amino acids is critical to maintaining enzyme activity. A mutein Bacillus GUS containing the amino acid alterations of Val 128→Ala, Leu 141→His, Tyr 204→Asp and Thr 560→Ala was constructed and exhibited little enzymatic activity. As shown herein, the residue alteration that most directly affected activity is Leu 141. In addition, three residues have been identified as likely contact residues important for catalysis in human GUS (residues Glu 451, Glu 540, and Tyr 504) (Jain et al., *Nature Struct. Biol.* 3: 375, 1996). Based on alignment with Bacillus GUS, the corresponding residues are Glu 415, Glu 508, and Tyr 471. By analogy with human GUS, Asp 165 may also be close to the reaction center and likely forms a salt bridge with Arg 566. Thus, in embodiments where it is desirable to retain enzymatic activity of GUS, the residues corresponding Leu 141, Glu 415, Glu 508, Tyr 471, Asp 165, and Arg 566 in Bacillus GUS are preferably unaltered.

In preferred embodiments, the protein and variants are capable of being secreted and exhibit β-glucuronidase activity. In other preferred embodiments, one or more of the biochemical characteristics exhibited by Bacillus GUS, such as its increased stability, its higher turnover number, and its activity in detergents, presence of end product, high salt conditions and organic solvents as compared to EcGUS, are retained in GUS and variants thereof. In other preferred embodiments, GUS and variants thereof are capable of being secreted and exhibit one or more of the biochemical characteristics disclosed herein. In other embodiments, variants of microbial GUS are capable of binding to a hapten, such as biotin, dinitrophenol, and the like.

In other embodiments, variants may exhibit glucuronide binding activity without enzymatic activity or be directed to other cellular compartments, such as membrane or cytoplasm. Membrane-spanning amino acid sequences are generally hydrophobic and many examples of such sequences are well-known. These sequences may be spliced onto microbial secreted GUS by a variety of methods including conventional recombinant DNA techniques. Similarly, sequences that direct proteins to cytoplasm (e.g., Lys-Asp-Glu-Leu (SEQ ID No: 11)) may be added to the reference GUS, typically by recombinant DNA techniques.

In other embodiments, the nucleic acid molecule encoding microbial GUS may be fused to another nucleic acid molecule. As will be appreciated, the fusion partner gene may contribute, within certain embodiments, a coding region. In a preferred embodiment, microbial GUS is fused to avidin or streptavidin. Thus, it may be desirable to use only the catalytic site of GUS (e.g., amino acids 415–508) of SEQ ID NO: 2. The choice of the fusion partner depends in part upon the desired application. The fusion partner may be used to alter specificity of GUS, provide a reporter function, provide a tag sequence for identification or purification protocols, and the like. The reporter or tag can be any protein that allows convenient and sensitive measurement or facilitates isolation of the gene product and does not interfere with the function of GUS. For example, green fluorescent protein and β-galactosidase are readily available as DNA sequences. A peptide tag is a short sequence, usually derived from a native protein, which is recognized by an antibody or other molecule. Peptide tags include FLAG®, Glu-Glu tag (Chiron Corp., Emeryville, Calif.) KT3 tag (Chiron Corp.), T7 gene 10 tag (Invitrogen, La Jolla, Calif.), T7 major capsid protein tag (Novagen, Madison, Wis.), $His_6$ (hexa-His), and HSV tag (Novagen). Besides tags, other types of proteins or peptides, such as glutathione-S-transferase may be used.

In addition, portions or fragments of microbial GUS may be isolated or constructed for use in the present invention. For example, restriction fragments can be isolated by well-known techniques from template DNA, e.g., plasmid DNA, and DNA fragments, including restriction fragments, can be generated by amplification. Furthermore, oligonucleotides can be synthesized or isolated from recombinant DNA molecules. One skilled in the art will appreciated that other methods are available to obtain DNA or RNA molecules having at least a portion of a microbial GUS sequence. Moreover, for particular applications, these nucleic acids may be labeled by techniques known in the art with a radiolabel (e.g., $^{32}P$, $^{33}P$, $^{35}S$, $^{125}I$, $^{131}I$, $^{3}H$, $^{14}C$), fluorescent label (e.g., FITC, Cy5, RITC, Texas Red), chemiluminescent label, enzyme, biotin and the like.

In other aspects of the present invention, isolated microbial glucuronidase proteins are provided. In one embodiment, GUS protein is expressed as a hexa-his fusion protein and isolated by metal-containing chromatography, such as nickel-coupled beads. Briefly, a sequence encoding $His_6$ is linked to a DNA sequence encoding a GUS. Although the $His_6$ sequence can be positioned anywhere in the molecule, preferably it is linked at the 3' end immediately preceding the termination codon. The His-GUS fusion may be constructed by any of a variety of methods. A convenient method is amplification of the GUS gene using a downstream primer that contains the codons for $His_6$.

In one aspect of the present invention, peptides having microbial GUS sequence are provided. Peptides may be used as immunogens to raise antibodies, as well as other uses. Peptides are generally five to 100 amino acids long, and more usually 10 to 50 amino acids. Peptides are readily chemically synthesized in an automated fashion (PerkinElmer ABI Peptide Synthesizer) or may be obtained commercially. Peptides may be further purified by a variety of methods, including high-performance liquid chromatography. Furthermore, peptides and proteins may contain amino acids other than the 20 naturally occurring amino acids or may contain derivatives and modification of the amino acids.

β-glucuronidase protein may be isolated by standard methods, such as affinity chromatography using matrices containing saccharose lactone, phenythio-β-glucuronide, antibodies to GUS protein and the like, size exclusion chromatography, ionic exchange chromatography, HPLC, and other known protein isolation methods. (see generally Ausubel et al. supra; Sambrook et al. supra). The protein can be expressed as a hexa-His fusion protein and isolated by metal-containing chromatography, such as nickel-coupled beads. An isolated purified protein gives a single band on SDS-PAGE when stained with Coomassie blue.

Antibodies to Microbial GUS

Antibodies to microbial GUS proteins, fragments, or peptides discussed herein may readily be prepared. Such antibodies may specifically recognize reference microbial GUS protein and not a mutant (or variant) protein, mutant (or variant) protein and not wild type protein, or equally recognize both the mutant (or variant) and wild-type forms. Antibodies may be used for isolation of the protein, inhibiting (antagonist) activity of the protein, or enhancing (agonist) activity of the protein.

Within the context of the present invention, antibodies are understood to include monoclonal antibodies, polyclonal antibodies, anti-idiotypic antibodies, antibody fragments (e.g., Fab, and $F(ab')_2$, $F_v$ variable regions, or complementarity determining regions). Antibodies are generally accepted as specific against GUS protein if they bind with a $K_d$ of greater than or equal to $10^{-7}M$, preferably greater than of equal to $10^{-8}M$. The affinity of a monoclonal antibody or binding partner can be readily determined by one of ordinary skill in the art (see Scatchard, *Ann. N.Y. Acad. Sci.* 51:660–672, 1949).

Briefly, a polyclonal antibody preparation may be readily generated in a variety of warm-blooded animals such as rabbits, mice, or rats. Typically, an animal is immunized with GUS protein or peptide thereof, which may be conjugated to a cawier protein, such as keyhole limpet hemocyanin. Routes of administration include intraperitoneal, intramuscular, intraocular, or subcutaneous injections, usually in an adjuvant (e.g., Freund's complete or incomplete adjuvant). Particularly preferred polyclonal antisera demonstrate binding in an assay that is at least three times greater than background.

Monoclonal antibodies may also be readily generated from hybridoma cell lines using conventional techniques (see U.S. Pat. Nos. RE 32,011, 4,902,614, 4,543,439, and 4,411,993; see also *Antibodies: A Laboratory Manual*, Harlow and Lane (eds.), Cold Spring Harbor Laboratory Press, 1988). Briefly, within one embodiment, a subject animal such as a rat or mouse is injected with GUS or a portion thereof. The protein may be administered as an emulsion in an adjuvant such as Freund's complete or incomplete adjuvant in order to increase the immune response. Between one and three weeks after the initial immunization the animal is generally boosted and may tested for reactivity to the protein utilizing well-known assays. The spleen and/or lymph nodes are harvested and immortalized. Various immortalization techniques, such as mediated by Epstein-Barr virus or fusion to produce a hybridoma, may be used. In a preferred embodiment, immortalization occurs by fusion with a suitable myeloma cell line (e.g., NS-1 (ATCC No. TIB 18), and P3X63—Ag 8.653 (ATCC No. CRL 1580) to create a hybridoma that secretes monoclonal antibody. The preferred fusion partners do not express endogenous antibody genes. Following fusion, the cells are cultured in medium containing a reagent that selectively allows for the growth of fused spleen and myeloma cells such as HAT (hypoxanthine, aminopterin, and thymidine) and are subsequently screened for the presence of antibodies that are reactive against a GUS protein. A wide variety of assays may be utilized, including for example countercurrent immuno-electrophoresis, radioimmnunoassays, radioimmunoprecipitations, enzyme-linked immunosorbent assays (ELISA), dot blot assays, western blots, immunoprecipitation, inhibition or competition assays, and sandwich assays (see U.S. Pat. Nos. 4,376, 110 and 4,486,530; see also *Antibodies: A Laboratory Manual*, Harlow and Lane (eds.), Cold Spring Harbor Laboratory Press, 1988).

Other techniques may also be utilized to construct monoclonal antibodies (see Huse et al., *Science* 246:1275–1281, 1989; Sastry et al., *Proc. Natl. Acad. Sci. USA* 86:5728–5732, 1989; Alting-Mees et al., *Strategies in Molecular Biology* 3:1–9, 1990; describing recombinant techniques). Briefly, RNA is isolated from a B cell population and utilized to create heavy and light chain immunoglobulin cDNA expression libraries in suitable vectors, such as λImmunoZAP(H) and λImmnoZAP(L). These vectors may be screened individually or co-expressed to form Fab fragments or antibodies (see Huse et al., supra; Sastry et al., supra). Positive plaques may subsequently be converted to a non-lytic plasmid that allows high level expression of monoclonal antibody fragments from *E. coli*.

Similarly, portions or fragments, such as Fab and Fv fragments, of antibodies may also be constructed utilizing conventional enzymatic digestion or recombinant DNA techniques to yield isolated variable regions of an antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources (e.g., Stratacyte, La Jolla, Calif.) Amplification products are inserted into vectors such as ImmunoZAP™ H or ImmunoZAP™ L (Stratacyte), which are then introduced into *E. coli*, yeast, or mannmalian-based systems for expression. Utilizing these techniques, large amounts of a single-chain protein containing a fusion of the $V_H$ and $V_L$ domains may be produced (see Bird et al., *Science* 242:423–426, 1988). In addition, techniques may be utilized to change a "murine" antibody to a "human" antibody, without altering the binding specificity of the antibody.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Assays for Function of β-glucuronidase

In preferred embodiments, microbial β-glucuronidase will have at least enzymatic activity and capability of being secreted. As noted above, variants of these reference GUS proteins may exhibit altered functional activity and cellular localization. Enzymatic activity may be assessed by an assay such as the ones disclosed herein or in U.S. Pat. No. 5,268,463 (Jefferson). Generally, a chromogenic or fluorogenic substrate is incubated with cell extracts, tissue sections, or purified protein. Cleavage of the substrate is monitored by a method appropriate for the aglycon.

A variety of methods may be used to demonstrate that a β-glucuronidase is secreted. For example, a rapid screening method in which colonies of organisms or cells, such as bacteria, yeast or insect cells, are plated and incubated with a readily visualized glucuronide substrate, such as X-glcA.

A colony with a diffuse staining pattern likely secretes GUS, although such a pattern could indicate that the cell has the ability to pump out the cleaved glucuronide or that the enzyme is membrane bound. When test cells express GUS from an introduced vector, a cell that is known to not pump out cleaved substrate is preferably used.

Secretion of the enzyme may be verified by assaying for GUS activity in the extracellular environment. If the cells secreting GUS are gram-positive bacteria, yeasts, molds, plants, or other organisms with cell walls, activity may be assayed in the culture medium and in a cell extract, however, the protein may not be transported through the cell wall. Thus, if no or low activity of a secreted form of GUS is found in the culture medium, protoplasts can be made by osmotic shock or enzymatic digestion of the cell wall or other suitable procedure, and the supernatant assayed for GUS activity. If the cells secreting GUS are gram-negative bacteria, culture supernatant may be tested, but more likely β-glucuronidase will be retained in the periplasmic space between the inner and outer membrane. In this case, spheroplasts may be made by osmotic shock, enzymatic digestion, or other suitable procedure, and the supernatant assayed for GUS activity. Other cells, without cell walls, are assayed for GUS in cell supernatant and cell extracts. The fraction of activity in each compartment is compared to the activity of a non-secreted GUS in the same or similar host cells. A β-glucuronidase is secreted if significantly more enzyme activity than E. coli GUS activity is found in extracellular spaces. Less than 10% of E. coli GUS is secreted. Higher amounts of secreted enzyme are preferred (e.g., greater than 20%, 25%, 30%, 40%, 50%).

Vectors, Host Cells and Means of Expressing and Producing Protein

Microbial β-glucuronidase may be expressed in a variety of host organisms. For protein production and purification, secreted GUS is preferably produced in bacteria, such as E. coli, for which many expression vectors have been developed and are available. Other suitable host organisms include other bacterial species (e.g., Bacillus, and eukaryotes, such as yeast (e.g., Saccharomyces cerevisiae), mammnalian cells (e.g., CHO and COS-7), plant cells and insect cells (e.g., Sf9). Vectors for these hosts are well known.

A DNA sequence encoding a secreted form of β-glucuronidase is introduced into an expression vector appropriate for the host. The sequence is derived from an existing clone or synthesized. A preferred means of synthesis is amplification of the gene from cDNA, genomic DNA, or a recombinant clone using a set of primers that flank the coding region or the desired portion of the protein. Restriction sites are typically incorporated into the primer sequences and are chosen with regard to the cloning site of the vector. If necessary, translational initiation and termination codons can be engineered into the primer sequences. The sequence of GUS can be codon-optimized for expression in a particular host. For example, a secreted form of β-glucuronidase isolated from a bacterial species that is expressed in a fungal host, such as yeast, is altered in nucleotide sequence to use codons preferred in yeast. Codon-optimization may be accomplished by methods such as splice overlap extension, site-directed mutagenesis, automated synthesis, and the like.

At minimum, the vector must contain a promoter sequence. Other regulatory sequences may be included. Such sequences include a transcription termination signal sequence, secretion signal sequence, origin of replication, selectable marker, and the like. The regulatory sequences are operationally associated with one another to allow transcription or translation.

Expression in Bacteria

The plasmids used herein for expression of secreted GUS include a promoter designed for expression of the proteins in a bacterial host. Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, RSV LTR, SV40, metallothionein promoter (see, e.g., U.S. Pat. No. 4,870,009) and other inducible promoters. For expression of the proteins, a promoter is inserted in operative linkage with the coding region for β-glucuronidase.

The promoter controlling transcription of β-glucuronidase may be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to the E. coli lacI repressor responsive to IPTG induction, the temperature sensitive λcI857 repressor, and the like. The E. coli lacI repressor is preferred.

In other preferred embodiments, the vector also includes a transcription terminator sequence. A "transcription terminator region" has either a sequence that provides a signal that terminates transcription by the polymerase that recognizes the selected promoter and/or a signal sequence for polyadenylation.

Preferably, the vector is capable of replication in bacterial cells. Thus, the vector preferably contains a bacterial origin of replication. Preferred bacterial origins of replication include the f1-ori and col E1 origins of replication, especially the ori derived from pUC plasmids.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene (Amp$^r$), tetracycline resistance gene (Tc$^r$) and the kanamycin resistance gene (Kan$^r$). The kanamycin resistance gene is presently preferred. Suitable markers for eukaryotes usually require a complementary deficiency in the host (e.g., thymidine kinase (tk) in tk- hosts). However, drug markers are also available (e.g., G418 resistance and hygromycin resistance).

The sequence of nucleotides encoding β-glucuronidase may also include a classical secretion signal, whereby the resulting peptide is a precursor protein processed and secreted. The resulting processed protein may be recovered from the periplasmic space or the fermentation medium. Secretion signals suitable for use are widely available and are well known in the art (von Heijne, *J. Mol. Biol.* 184:99–105, 1985). Prokaryotic and eukaryotic secretion signals that are functional in E. coli (or other host) may be employed. The presently preferred secretion signals include, but are not limited to, those encoded by the following E. coli genes: pelB (Lei et al., *J. Bacteriol.* 169:4379, 1987), phoA, ompA, ompT, ompF, ompC, beta-lactamase, and alkaline phosphatase.

Figure 15:
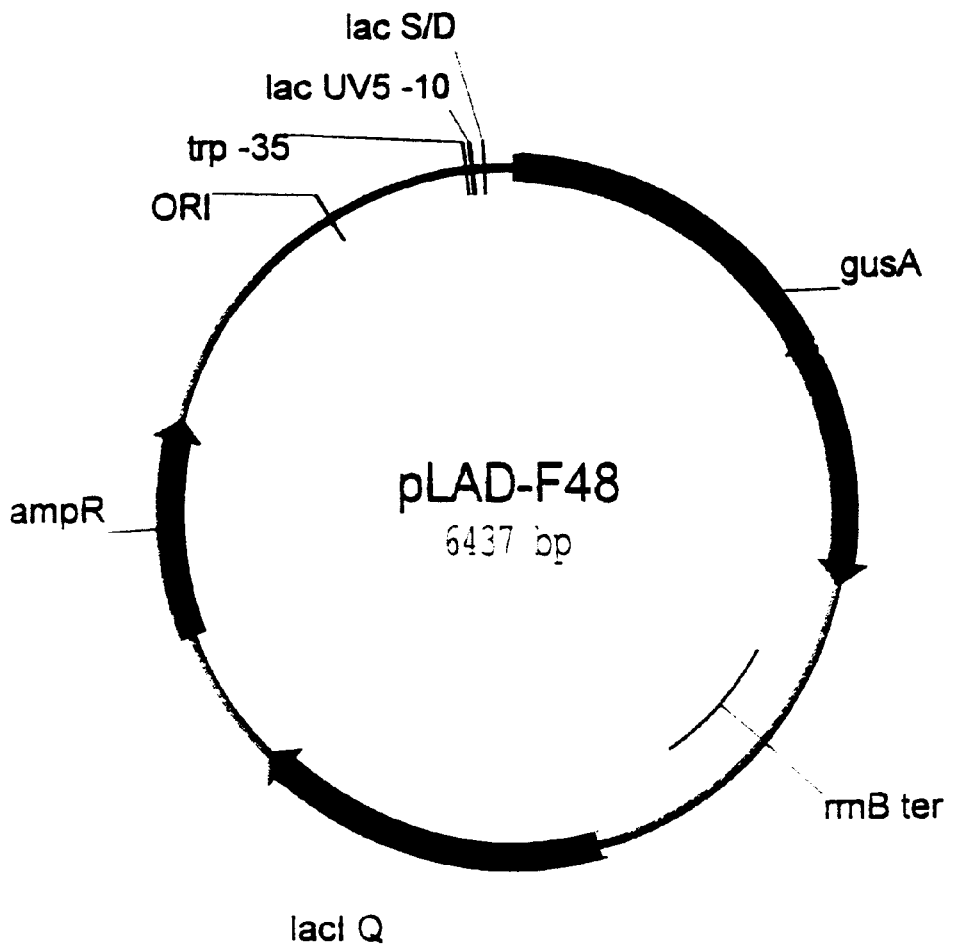
FIG. 15 is a map of the expression vector pLAD-F48 containing Bacillus GUS, showing key features.

One skilled in the art appreciates that there are a wide variety of suitable vectors for expression in bacterial cells and which are readily obtainable. Vectors such as the pET series (Novagen, Madison, Wis.) and the tac and trc series (Pharmacia, Uppsala, Sweden) are suitable for expression of a β-glucuronidase. A preferred vector is the backbone of pLAD-F48 (FIG. 15). This plasmid is ampicillin resistant, has a colEI origin of replication, lacI$^q$ gene, a lac/trp hybrid promoter in front of the lac Shine-Dalgarno sequence, a hexa-his coding sequence that joins to the 3' end of the inserted gene, and an rmB terminator sequence.

The choice of a bacterial host for the expression of a β-glucuronidase is dictated in part by the vector. Commercially available vectors are paired with suitable hosts. The vector is introduced in bacterial cells by standard methodology. Typically, bacterial cells are treated to allow uptake of DNA (for protocols, see generally, Ausubel et al., supra; Sambrook et al., supra). Alternatively, the vector may be introduced by electroporation, phage infection, or another suitable method.

Expression in Plant Cells

As noted above, the present invention provides vectors capable of expressing secreted β-glucuronidase. For agricultural applications, the vectors should be functional in plant cells. Vectors and procedures for cloning and expression in E. coli and animal cells are discussed herein and, for example, in Sambrook et al (supra) and in Ausubel et al. (supra). In one embodiment, rice is a host for GUS gene expression.

Vectors that are functional in plants are preferably binary plasmids derived from Agrobacterium plasmids. Such vectors are capable of transforming plant cells. These vectors contain left and right border sequences that are required for integration into the host (plant) chromosome. At minimum, between these border sequences is the gene to be expressed under control of a promoter. In preferred embodiments, a selectable marker and a reporter gene are also included. The vector also preferably contains a bacterial origin of replication.

A gene for microbial β-glucuronidase should be in operative linkage with a promoter. The promoter should be functional in a plant cell. Typically, the promoter is derived from a host plant gene, but promoters from other plant species and other organisms, such as insects, fungi, viruses, mammals, and the like, may also be suitable, and at times preferred. The promoter may be constitutive or inducible, or may be active in a certain tissue or tissues (tissue type-specific promoter), in a certain cell or cells (cell-type specific promoter), of at a particular stage or stages of development (development-type specific promoter). The choice of a promoter depends at least in part upon the application. Many promoters have been identified and isolated (see, generally, GenBank and EMBL databases). Other promoters may be isolated by well-known methods. For example, a genomic clone for a particular gene can be isolated by probe hybridization. The coding region is mapped by restriction mapping, DNA sequence analysis, RNase probe protection, or other suitable method. The genomic region immediately upstream of the coding region comprises a promoter region and is isolated. Generally, the promoter region is located in the first 200 bases upstream, but may extend to 500 or more bases. The candidate region is inserted in a suitable vector in operative linkage with a reporter gene, such as in pBI121 in place of the CaMV 35S promoter, and the promoter is tested by assaying for the reporter gene after transformation into a plant cell. (see, generally, Ausubel et al., supra; Sambrook et al., supra; *Methods in Plant Molecular Biolgoy and Biotechnology*, Ed. Glick and Thompson, CRC Press, 1993.)

Preferably, the vector contains a selectable marker for identifying transformnants. The selectable marker preferably confers a growth advantage under appropriate conditions. Generally, selectable markers are drug resistance genes, such as neomycin phosphotransferase. Other drug resistance genes are known to those in the art and may be readily substituted. The selectable marker also preferably has a linked constitutive or inducible promoter and a termination sequence, including a polyadenylation signal sequence.

Additionally, a bacterial origin of replication and a selectable marker for bacteria are preferably included in the vector. Of the various origins (e.g., colEI, fd phage), a colEI origin of replication is preferred. Most preferred is the origin from the pUC plasmids, which allow high copy number. Selectable markers for bacteria include, ampicillin resistance, tetracycline resistance, kanamycin resistance, chloramphenicol resistance, and the like.

The sequence of nucleotides encoding β-glucuronidase may also include a classical secretion signal, whereby the resulting peptide is a precursor protein processed and secreted. Suitable signal sequences of plant genes include, but are not limited to the signal sequences from glycine-rich protein and extension. In addition, a glucuronide permease gene may be co-transfected either from the same vector containing microbial GUS or from a separate expression vector.

A general vector suitable for use in the present invention is based on pBI121 (U.S. Pat. No. 5,432,081) a derivative of pBIN19. Other vectors have been described (U.S. Pat. No. 4,536,475) or may be constructed based on the guidelines presented herein. The plasmid pBI121 contains a left and right border sequence for integration into a plant host chromosome and also contains a bacterial origin of replication and selectable marker. These border sequences flank two genes. One is a kanamycin resistance gene (neomycin phosphotransferase) driven by a nopaline synthase promoter and using a nopaline synthase polyadenylation site. The second is the E. coli GUS gene (reporter gene) under control of the CaMV 35S promoter and polyadenlyated using a nopaline synthase polyadenylation site. The E. coli GUS gene is replaced with a gene encoding a secreted form of β-glucuronidase. If appropriate, the CaMV 35S promoter is replaced by a different promoter. Either one of the expression units described above is additionally inserted or is inserted in place of the CaMV promoter and GUS gene.

Plants may be transformed by any of several methods. For example, plasmid DNA may be introduced by Agrobacterium co-cultivation or bombardment. Other transformation methods include electroporation, $CaPO_4$-mediated transfection, gene transfer to protoplasts, microinjection, and the like (see, *Gene Transfer to Plants*, Ed. Potrykus and Spangenberg, Springer, 1995, for procedures). Preferably, vector DNA is first transfected into Agrobacterium and subsequently introduced into plant cells. Most preferably, the infection is achieved by co-cultivation. In part, the choice of transformation methods depends upon the plant to be transformed. For example, monocots generally cannot be transformed by Agrobacterium. Thus, Agrobacterium transformation by co-cultivation is most appropriate for dicots and for mitotically active tissue. Non-mitotic dicot tissues can be efficiently infected by Agrobacterium when a projectile or bombardment method is utilized. Projectile methods are also generally used for transforming sunflowers and soybean. Bombardment is used when naked DNA, typically Agrobacterium or pUC-based plasmids, is used for transformation or transient expression.

Briefly, co-cultivation is performed by first transforming Agrobacterium by freeze-thawing (Holsters et al., *Mol. Gen. Genet.* 163: 181–187, 1978) or by other suitable methods (see, Ausubel, et al. supra; Sambrook et al., supra). A culture of Agrobacterium containing the plasmid is incubated with leaf disks, protoplasts or meristematic tissue to generate transformed plants (Bevan, *Nucl. Acids. Res.* 12:8711, 1984).

Briefly, for microprojectile bombardment, seeds are surface sterilized in bleach solution and rinsed with distilled water. Seeds are then imbibed in distilled water, and the cotyledons are broken off to produce a clean fracture at the plane of the embryonic axis. Explants are then bisected longitudinally between the primordial leaves and placed cut surface up on medium with growth regulating hormones, minerals and vitamin additives. Explants are bombarded with 1.8 μm tungsten microprojectiles by a particle acceleration device. Freshly bombarded explants are placed in a suspension of transformed Agrobacterium transferred to medium with the cut surfaces down for 3 days with an 18 hr light cycle. Explants are transferred to medium lacking growth regulators but containing drug for selection and grown for 2–5 weeks. After 1–2 weeks more without drug selection, leaf samples from green, drug-resistant shoots are grafted to in vitro grown rootstock and transferred to soil.

Activity of secreted GUS is assayed in whole plants or in selected tissues using a glucuronide substrate that is readily detected upon cleavage. Glucuronide substrates that are calorimetric are preferred. Field testing of plants may be performed by spraying a plant with the glucuronide substrate and observing color formation of the cleaved product.

Expression in Other Organisms

A variety of other organisms are suitable for use in the present invention. For example, various fungi, including yeasts, molds, and mushrooms, insects, especially vectors for diseases and pathogens, and other animals, such as cows, mice, goats, and the like, may be transformed with a GUS transgene.

The principles that guide vector construction for bacteria and plants, as discussed above, are applicable to vectors for these organisms. In general, vectors are well known and readily available. Briefly, the vector should have a promoter in operative linkage with GUS. Usually, the vector will also have one or more selectable markers, an origin of replication, a polyadenylation signal and transcription terminator.

The sequence of nucleotides encoding β-glucuronidase may also include a classical secretion signal, whereby the resulting peptide is a precursor protein processed and secreted. Suitable secretion signals may be obtained from mat-alpha or invertase genes for example. In addition, a permease gene may be co-transfected.

Uses of Microbial β-glucuronidase

As noted above, microbial β-glucuronidase may be used in a variety of applications. In general, microbial β-glucuronidase can be used as a reporter/effector molecule and as a diagnostic tool. As taught herein, microbial β-glucuronidase that is secretable is advantageous as a reporter/effector molecule, whereas, in dignostic applications, the biochemical characteristics of the β-glucuronidase disclosed herein provide advantages.

Secreted microbial GUS can be used as a marker for transgenic constructions. In a preferred embodiment, the transgenic host is a plant, such as rice, corn, wheat. The transgenic GUS may be used in at least two ways: one in a method of positive selection, obviating the need for drug resistance selection, and a second as a means of detecting and tracking linked genes.

For positive selection, the plant cell is transformed with a s-GUS (secretable GUS) transgene. Selection is achieved by providing the cells with a gluronidated form of a required nutrient. For example, all cells require a carbon source, such as glucose. In one embodiment, glucose is provided as glucuronyl glucose, which is cleaved by s-GUS into glucose plus glucuronic acid. The glucose would then bind to receptors and be taken up by cells. The glucuronide may be any required compound, including without limitation, a cytokinin, auxin, vitamin, carbohydrate, nitrogen-containing compound, and the like. It will be appreciated that this positive selection method can be used for cells and tissues derived from diverse organisms, such as animal cells, insect cells, fungi, and the like. The choice of glucuronide will depend in part upon the requirements of the host cell.

As a marker, s-GUS is preferred because it is non-destructive, that is, the host does not need to be destroyed in order to assay enzyme activity. A non-destructive marker has special utility as a tool in plant breeding. The GUS enzyme can be used to detect and track linked endogenous or exogenously introduced genes. s-GUS may also be used to generate sentinel plants that serve as bioindicators of environmental status. Plant pathogen invasion can be monitored if GUS is under control of a pathogen promoter. In addition, such transgenic plants may serve as a model system for screening inhibitors of pathogen invasion. In this system, GUS is expressed if a pathogen invades. In the presence of an effective inhibitor, GUS activity will not be detectable. In certain embodiments, s-GUS is co-transfected with a gene encoding a glucuronide permease.

Preferred transgenes for introduction into plants encode proteins that affect fertility, including male sterility, female fecundity, and apomixis, plant protection genes, including proteins that confer resistance to diseases, bacteria, fungus, nemotodes, viruses and insects; genes and proteins that affect developmental processes or confer new phenotypes, such as genes that control development of meristem, timing of flowering, and the such.

Insect and disease resistance genes are well known. Some of these genes are present in the genome of plants and have been genetically identified. Others of these genes have been found in bacteria and are used to confer resistance.

Particularly well known insect resistance genes are the crystal genes of *Bacillus thuringiensis*. The crystal genes are active against various insects, such as lepidopterans, Diptera, and mosquitos. Many of these genes have been cloned. For examples, see, GenBank Accession Nos. X96682, X96684; M76442, M90843, M89794, M22472, M37207, D17518, L32019, M97880, L32020, M64478, M11250, M13201, D00117, M73319, X17123, X86902, X06711, X13535, X54939, X54159, X13233, X54160, X56144, X58534, X59797, X75019, X62821, Z46442, U07642, U35780, U43605, U43606, U10985; U.S. Pat. Nos. 5,317,096; 5,254,799; 5,460,963; 5,308,760, 5,466,597, 5,2187,091, 5,382,429, 5,164,180, 5,206,166, 5,407,825, 4,918,066; PCT Applications WO 95/30753, WO 94/24264; AU 9062083; EP 408403 B1, EP 142924 B1, EP 256,553 B1, EP 192,741 B1; JP 62-56932;. Gene sequences for these and related proteins may be obtained by standard and routine technologies, such as probe hybridization of a *B. thuringiensis* library or amplification (see generally, Sambrook et al., supra, Ausubel et al. supra). The probes and primers may be synthesized based on publicly available sequence information.

Other resistance genes to Sclerotinia, cyst nematodes, tobacco mosaic virus, flax and crown rust, rice blast, powdery mildew, verticillum wilt, potato beetle, aphids, as well as other infections, are useful within the context of this invention. Examples of such disease resistance genes may be isolated from teachings in the following references: isolation of rust disease resistance gene from flax plants (WO 95/29238); isolation of the gene encoding Rps2 protein from *Arabidopsis thaliana* that confers disease resistance to pathogens carrying the avrRpt2 avirulence gene (WO 95/28478); isolation of a gene encoding a lectin-like protein of kidney bean confers insect resistance (JP 71-32092); isolation of the Hml disease resistance gene to *C. carbonum* from maize (WO 95/07989); for examples of other resistance genes, see WO 95/05743; U.S. Pat. No. 5,496,732; U.S. Pat. No. 5,349,126; EP 616035; EP 392225; WO 94/18335; JP 43-20631; EP 502719; WO 90/11770; U.S. Pat. No. 5,270,200; U.S. Pat. Nos. 5,218,104 and 5,306,863). In addition, general methods for identification and isolation of plant disease resistance genes are disclosed (WO 95/28423). Any of these gene sequences suitable for insertion in a vector according to the present invention may be obtained by standard recombinant technology techniques, such as probe hybridization or amplification. When amplification is performed, restriction sites suitable for cloning are preferably inserted. Nucleotide sequences for other transgenes, such as controlling male fertility, are found in U.S. Pat. No. 5,478,369, references therein, and Mariani et al., *Nature* 347–737, 1990.

In similar fashion, secreted GUS can be used to generate transgenic insects for tracking insect populations or facilitate the development of a bioassay for compounds that affect molecules critical for insect development (e.g., juvenile hormone). Secreted GUS may also serve as a marker for beneficial fungi destined for release into the environment. The non-destructive marker is useful for detecting persistance and competitive advantage of the released organisms.

In animal systems, secreted GUS may be used to achieve extracellular detoxification of glucuronides (e.g, toxin glucuronide) and examine conjugation patterns of glucuronides. Furthermore, as discussed above, secreted GUS may be used as a transgenic marker to track cells or as a positive selection system, or to assist in development of new bioactive GUS substrates that do not need to be transported across membrane.

In one aspect, microbial purified β-glucuronidase is used in medical applications. For these applications, secretion is not a necessary characteristic. The biochemical attributes, such as increased stability and enzymatic activity disclosed herein are preferred characteristics. The microbial glucuronidase preferably has one or more of the disclosed characteristics.

For the majority of drug or pharmaceutical analysis, the compounds in urine, blood, saliva, or other bodily fluids are de-glucuronidated prior to analysis. Such procedure is undertaken because compounds are often, if not nearly always, detoxified by glucuronidation. Thus, drugs that are in circulation and have passed through a site of glucuronidation (e.g, liver) are found conjugated to glucuronic acid. Such glucuronides yield a complex pattern upon analysis by, for example, HPLC. However, after the aglycon (drug) is cleaved from the glucuronic acid, a spectrum can be compared to a reference spectrum. Currently, *E. coli* GUS is utilized, but as shown herein, Bacillus GUS has superior qualities.

The microbial GUS enzymes disclosed herein may be used in traditional medical diagnostic assays, such as described above for drug testing, pharmacokinetic studies, bioavailability studies, diagnosis of diseases and syndromes, following progression of disease or its response to therapy and the like. These β-glucuronidase enzymes may be used in place of other traditional enzymes (e.g., alkaline phosphatase, horseradish peroxidase, beta-galactosidase, and the like) and compounds (e.g., green fluorescent protein, radionuclides) that serve as visualizing agents. Microbial GUS has critical qualities for use as a visualizing agent: it is highly specific for the substrate, water soluble and the substrates are stable. Thus, microbial GUS is suitable for use in southern analysis of DNA, northern analysis, ELISA, and the like. In preferred embodiments, microbial GUS binds a hapten, either as a fusion protein with a partner protein that binds the hapten (e.g., avidin that binds biotin) or alone. If used alone, microbial GUS can be mutagenized and selected for hapten-binding abilities. Mutagenesis and binding assays are well known in the art. In addition, microbial GUS can be conjugated to avidin, streptavidin, or other hapten binding protein and used as a reporter in the myriad assays that currently employ enzyme-linked binding proteins. Such assays include immunoassays, Western blots, in situ hybridizations, HPLC, high-throughput binding assays, and the like (see, for examples, U.S. Pat. Nos. 5,328,985 and 4,839,293, which teach avidin and streptavidin fusion proteins and U.S. Pat. No. 4,298,685, Diamandis and Christopoulos, *Clin. Chem.* 37:625, 1991; Richards, *Methods Enzymol.* 184:3, 1990; Wilchek and Bayer, *Methods Enzymol.* 184:467. 1990; Wilchek and Bayer, *Methods Enzymol.* 184:5, 1990; Wilchek and Bayer, *Methods Enzymol.* 184:14, 1990; Dunn, *Methods Mol. Biol.* 32:227, 1994; Bloch, *J. Hitochem. Cytochem.* 41:1751, 1993; Bayer and Wilchek *J. Chromatogr.* 510:3, 1990, which teach various applications of enzyme-linked technologies and methods).

The present invention also provides kits comprising microbial GUS protein or expression vectors containing microbial GUS gene. One exemplary type of kit is a dipstick test. Such tests are widely utilized for establishing pregnancy, as well as other conditions. Generally, these dipstick tests assay the glucuronide form, but it would be advantageous to use reagents that detect the aglycon form. Thus, GUS may be immobilized on the dipstick adjacent to or mixed in with the detector molecule (e.g., antibody). The dipstick is then dipped in the test fluid (e.g., urine) and as the compounds flow past GUS, they are cleaved into aglycon and glucuronic acid. The aglycon is then detected. Such a setup may be extremely useful for testing compounds that are not readily detectable as glucuronides.

In a variation of this method, the microbial GUS enzyme is engineered to bind a glucuronide but lacks enzymatic activity. The enzyme will then bind the glucuronide and the enzyme is detected by standard methodology. Alternatively, GUS is fused to a second protein, either as a fusion protein or as a chemical conjugate, that binds the aglycon. The fusion is incubated with the test substance and an indicator substrate is added. This procedure may be used for ELISA, Northern, Southern analysis and the like.

The following examples are offered by way of illustration, and not by way of limitation.

EXAMPLES

Example 1

ISOLATION OF A GENE ENCODING SECRETED β-GLUCURONIDASE

Soil samples are placed in broth and plated for growth of bacterial colonies on agar plates containing 50 $\mu$g/ml X-glcA (5-bromo-4-chloro-3-indolyl glucuronide), an indicator substrate for β-glucuronidase. This substrate gives a blue precipitate at the site of enzyme activity (see U.S. Pat. No. 5,268,463). Bacteria that secrete β-glucuronidase have a strong, diffuse staining pattern surrounding the colony.

One bacterial colony that exhibited this type of staining pattern is chosen. The bacterium is identified as a Bacillus based on amplification of 16S rRNA. Oligonucleotide sequences derived from areas exhibiting a high degree of similarity between *E. coli* and human β-glucuronidases are used in amplification reactions on Bacillus and *E. coli* DNA. A fragment is observed using Bacillus DNA, which is the same size as the *E. coli* fragment.

Bacillus DNA is digested with Hind III and ligated to Hind III-digested pBSII-KS plasmid vector. The recombinant plasmid is transfected into KW1, an *E. coli* strain that is deleted for the GUS operon. Cells are plated on X-glcA plates, and one colony exhibited strong, diffuse staining pattern, suggesting that this clone encoded a secreted β-glucuronidase enzyme. The plasmid, pRAJa17.1, is isolated and subjected to analysis.

The DNA sequence of the insert of pRAJa17.1 is shown in FIG. 1 (SEQ ID No: 1). A schematic of the 6029 bp fragment is shown in FIG. 2. The fragment contains four large open reading frames. The open reading frame proposed as secreted GUS (BoGUS) begins at nucleotide 1662 and extends to 3467 (FIG. 1 (SEQ ID No: 1)). The predicted translate is shown in FIG. 3 and its alignment with *E. coli* and human β-glucuronidase is presented in FIG. 4. BoGUS is 47.2% identical to *E. coli* GUS, which is about the same identity as human GUS and *E. coli* GUS (49.1%). Thus, GUS from Bacillus is about as related to another bacterium as to human. One striking difference in sequence among the proteins is the number of cysteine residues. Whereas, both human and *E. coli* GUS have 4 and 9 cysteines, respectively, BoGUS has only one cysteine.

The secreted GUS protein is 602 amino acids long and doe s not have a canonical leader peptide. A prototypic leader sequence has an amino-terminal positively charged region, a central hydrophobic region, and a more polar carboxy-terminal region (see, von Heijne, *J. Membrane Biol.* 115:195–201, 1990) and is generally about 20 amino acids long. However, in both mammalian and bacteria cells, proteins without canonical or identifiable secretory sequences have been found in extracellular or periplasmic spaces.

Example 2

PROPERTIES OF SECRETED β-GLUCURONIDASE

Figure 6:
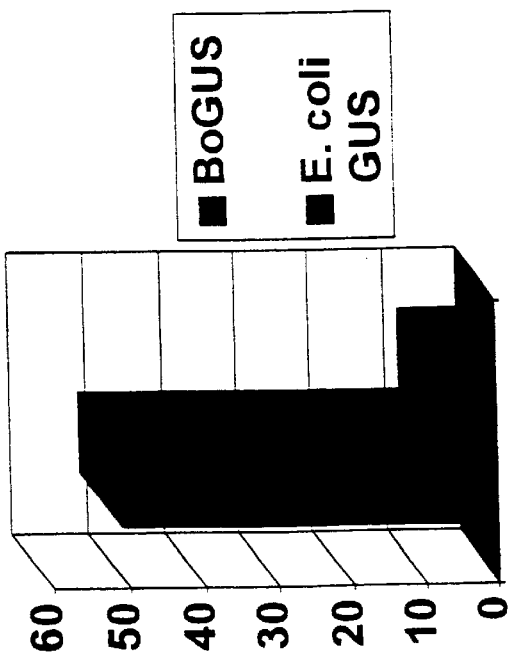
FIG. 6 is a graph showing that Bacillus GUS is secreted in $E.$ $coli$ transformed with an expression vector encoding Bacillus GUS. The secretion index is the percent of total activity in periplasm less the percent of total β-galactosidase activity in periplasm.

Although the screen described above suggests that the Bacillus GUS is secreted, the cellular localization of BoGUS is examined. Cellular fractions (e.g, periplasm, spheroplast, supernatant, etc.) are prepared from KW1 cells transformed with pRAJa17.1 or a subfragment that contains the GUS gene and from *E coli* cells that express β-glucuronidase. GUS activity and β-galactosidase activity is determined for each fraction. The percent of total activity in the periplasm fraction for GUS and β-gal (a non-secreted protein) are calculated; the amount of β-gal activity is considered background and thus is subtracted from the amount of β-glucuronidase activity. In FIG. 6, the relative activities of BoGUS and *E. coli* GUS in the periplasm fraction are plotted. As shown, approximately 50% of BoGUS activity is found in the periplasm, whereas less than 10% of *E. coli* GUS activity is present.

The thermal stability of BoGUS and *E. coli* GUS enzymes are determined at 65° C., using an substrate that can be measured by spectrophotometry, for example. One such substrate is p-nitrophenyl β-D-glucuronide (pNPG), which when cleaved by GUS releases the chromophore p-nitrophenol. At a pH greater than its pKa (approximately 7.15), the ionized chromophore absorbs light at 400–420 nm, in the yellow range of visible light. Briefly, reactions are performed in 50 mM NaPO4 pH 7.0 ,10 mM 2-ME, 1 mM EDTA, 1 mM pNPG, and 0.1% Triton® X-100 at 37° C. The reactions are terminated by the addition of 0.4 ml of 2-amino, 2-methyl propanediol, and absorbance measured at 415 nm against a substrate blank. Under these conditions, the molar extinction coefficient of p-nitorphenol is assumed to be 14,000. One unit is defined as the amount of enzyme that produces 1 nmole of product/min at 37° C.

Figure 7:
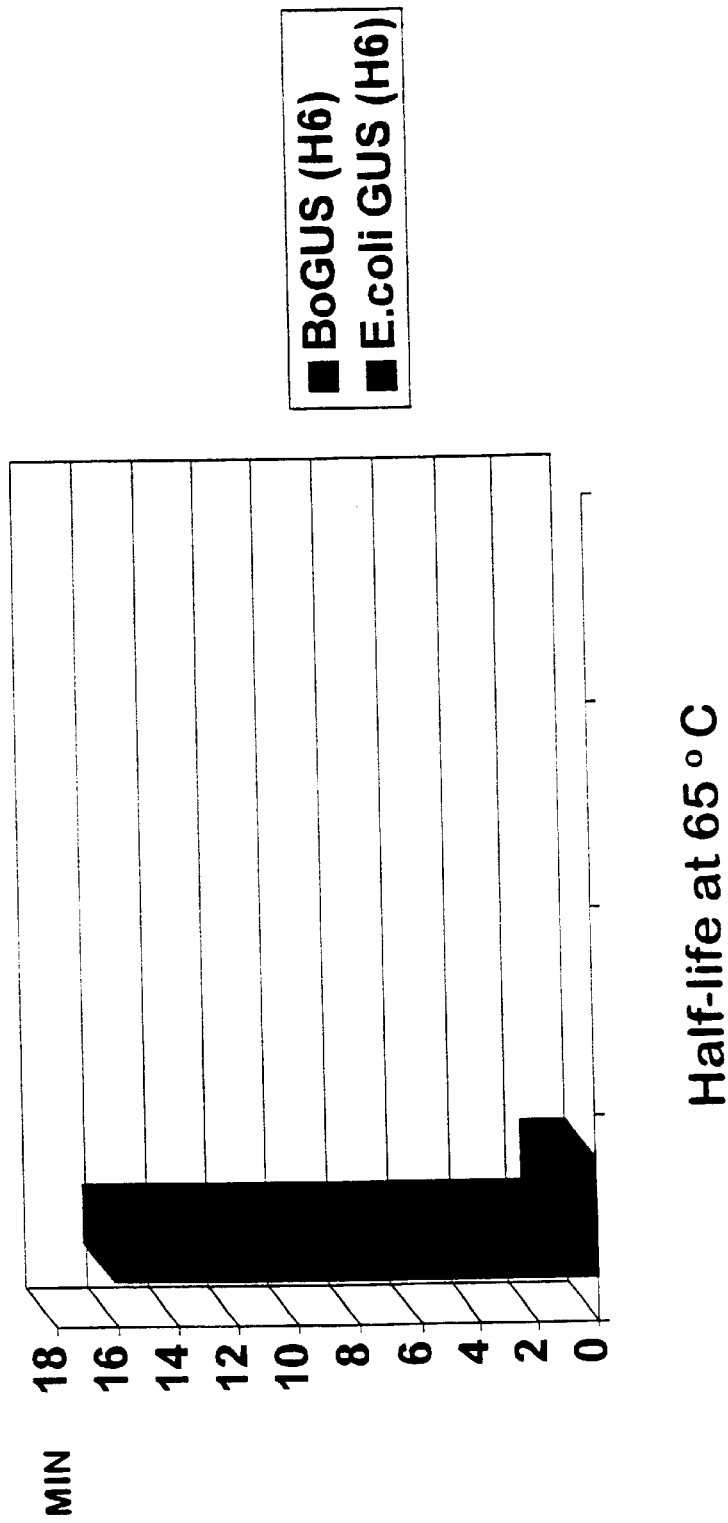
FIG. 7 is a graph illustrating the half-life of Bacillus GUS and $E.$ $coli$ GUS at 65° C.

As shown in FIG. 7, BoGUS has a half-life of approximately 16 min, while *E. coli* GUS has a half-life of less than 2 min. Thus, BoGUS is at least 8 times more stable than the *E. coli* GUS. In addition, the catalytic properties of BoGUS are substantially better than the *E. coli* enzyme. The Km is two-fold less and the Vmax is 2.5 times greater.

TABLE 1

|  | BoGUS | *E. coli* GUS |
| --- | --- | --- |
| Km | 70 μM pNPG | 150 μM pNPG |
| Vmax | 90 nmoles/min/μg | 35 nmoles/min/μg |

Figure 8:
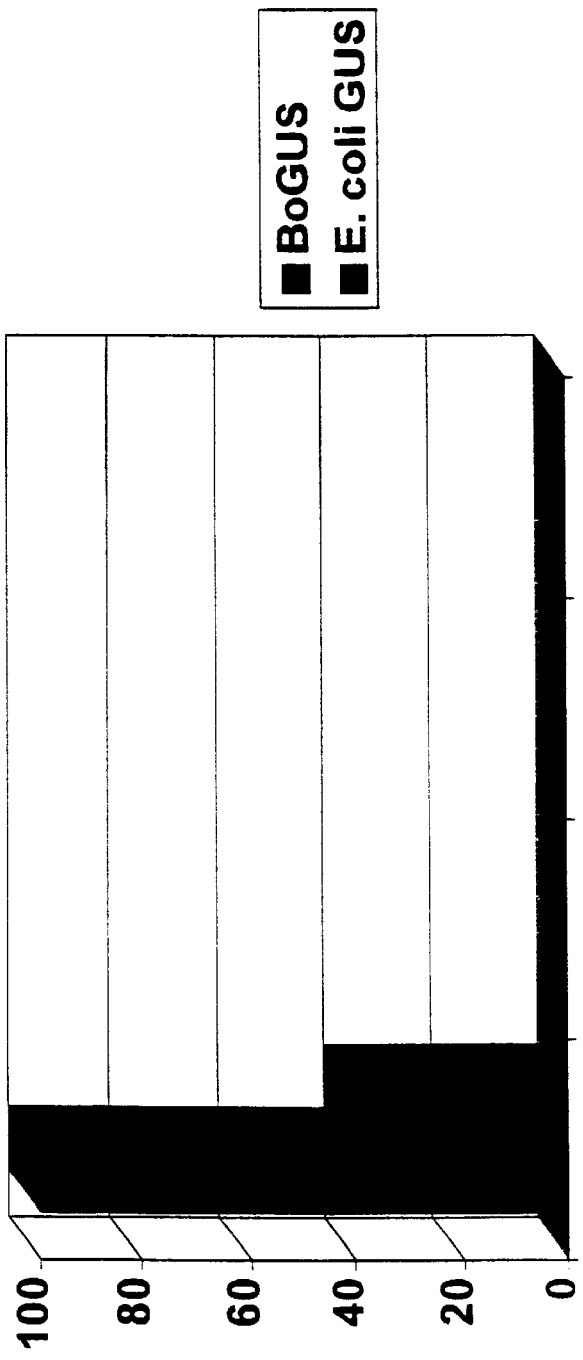
FIG. 8 is a graph showing the turnover number of Bacillus GUS and $E.$ $coli$ GUS enzymes at 37° C.
Figure 9:
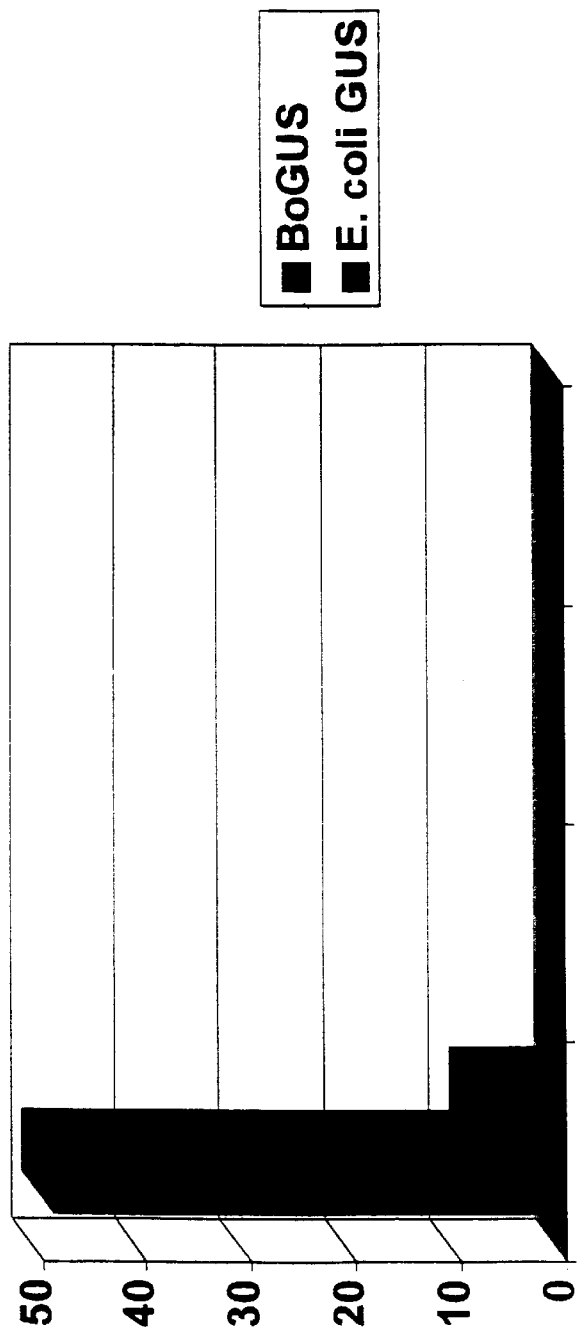
FIG. 9 is a graph showing the turnover number of Bacillus GUS and $E.$ $coli$ GUS enzymes at room temperature.

The turnover number of BoGUS is 2.5 to 5 times higher than *E. coli* GUS at either 37° C. or at room temperature (FIGS. 8 and 9). A turnover number is calculated as nmoles of pNPG converted to p-nitrophenol per min per μg of purified protein.

BoGUS enzyme activity is resistant to inhibition by detergents. Enzyme activity assays are measured in the presence of varying amounts of SDS, Triton® X-100, or sarcosyl. As presented in FIG. 10, BoGUS was not inhibited or only slightly inhibited (<20% inhibition) in Triton® X-100 and Sarcosyl. In SDS, the enzyme still had substantial activity (60–75% activity). In addition, BoGUS is not inhibited by the end product of the reaction. Activity is determined normally or in the presence of 1 or 10 mM glucuronic acid. No inhibition is seen at either 1 or 10 mM glucuronic acid (FIG. 11). The enzyme is also assayed in the presence of organic solvents, dimethylformamide (DMF) and dimethylsulfoxide (DMSO), and high concentrations of NaCl (FIG. 12). Only at the highest concentrations of DMF and DMSO (20%) does BoGUS demonstrate inhibition, which is approximately 40% inhibited. In lesser concentrations of organic solvent and in the presence of 1 M NaCl, BoGUS retains essentially complete activity.

Example 3

CONSTRUCTION OF A CODON OPTIMIZED SECRETED β-GLUCURONIDASE

The Bacillus GUS gene is codon-optimized for expression in *E. coli*. Codon frequencies for each codon are determined by back translation using ecohigh codons for highly expressed genes of enteric bacteria. These ecohigh codon usages are available from GCG. The most frequently used codon for each amino acid is then chosen for synthesis. In addition, the polyadenylation signal, AATAAA, splice consensus sequences, ATTTA AGGT, and restriction sites that are found in polylinkers are eliminated. Other changes may be made to reduce potential secondary structure. To facilitate cloning in various vectors, four different 5' ends are synthesized: the first, called A0 (shown in FIG. 13), uses a sequence comprising an Nco I (underlined), Bgl II (double underlined), and Spe I (italicized) sites (GTCGAC CCATGGTAGATCTGACTAGT) (SEQ ID NO: 12) are added just 5' to the Leu codon at amino acid 2 in FIG. 3. The second one, called AI, adds the native Shine/Dalgarno sequence (GTCGACAGGAGTGCTATC) 5' (SEQ ID NO: 13) of the initiator Met codon; the third, called AII, adds a modified Shine/Dalgarno sequence 5' of the initiator Met codon such that a Nco I site is added (GTCGACAGGAGTGCTAC) (SEQ ID NO: 14); the fourth one, called AIII adds a modified Shine/Dalgarno sequence (GTCGACAGGAGTGCTACCATGGTAGA (SEQ ID NO: 15)) 5' of the Leu codon (residue 2). All of these 5' added sequences contain a Sal I site at the extreme 5' end to facilitate construction and cloning. In certain embodiments, to facilitate protein purification, a sequence comprising an Nhe I (underlined) site, an Apa I (double underlined) site, and encoding hexa-his amino acids at joined at the 3' (COOH-terminus) of the gene.

GCTAGCCATCACCATCACCATCACGTGTGAATT GGTGACCGGGCCC (SEQ ID NO: 16)
SerSerHisHisHisHisHisHisVal (SEQ ID NO:17)*

Figure 14:
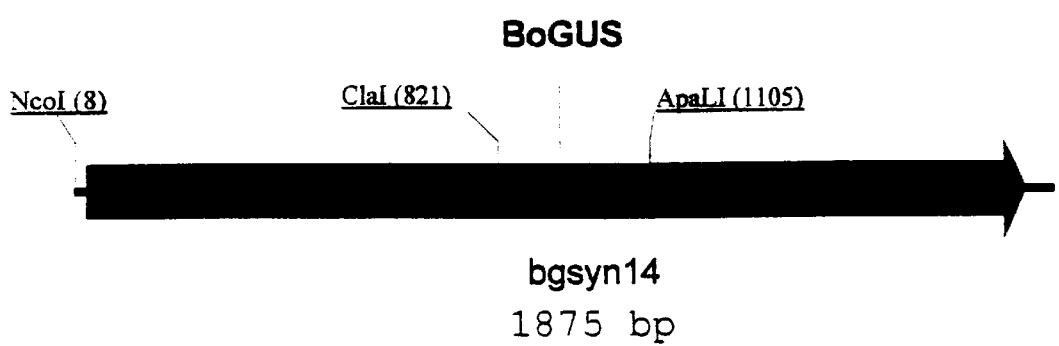
FIG. 14 is a schematic of the DNA sequence of Bacillus GUS that is codon optimized for production in $E.$ $coli.$

Nucleotide and amino acid sequences of one engineered secretable microbial GUS are shown in FIG. 13, and a schematic is shown in FIG. 14. The coding sequence for this protein is assembled in pieces. The sequence is dissected into four fragments, A (bases 1–457); B (bases 458–1012); C (bases 1013–1501); and D (bases 1502–1875). Oligonucleotides (Table 2) that are roughly 80 bases (range 36–100 bases) are synthesized to overlap and create each fragment. The fragments are each cloned separately and the DNA sequence verified. Then, the four fragments are excised and assembled in pLITMUS 39 (New England Biolabs, Beverley, Mass.), which is a small, high copy number cloning plasmid.

TABLE 2

| Oligo name | Size | Sequence | SEQ ID NO |
|---|---|---|---|
| BoGUS A-1-80T | 80 | TCGACCCATGGTAGATCTGACTAGTCTGTACCCGATCAACAC CGAGACCCGTGGCGTCTTCGACCTCAATGGCGTCTGGA | 18 |
| BoGUS A-121-200B | 80 | GGATTTCCTTGGTCACGCCAATGTCATTGTAACTGCTTGGGA CGGCCATACTAATAGTGTCGGTCAGCTTGCTTTCGTAC | 19 |
| BoGUS A-161-240T | 80 | CCAAGCAGTTACAATGACATTGGCGTGACCAAGGAAATCCGC AACCATATCGGATATGTCTGGTACGAACGTGAGTTCAC | 20 |
| BoGUS A-201-280B | 80 | GCGGAGCACGATACGCTGATCCTTCAGATAGGCCGGCACCGT GAACTCACGTTCGTACCAGACATATCCGATATGGTTGC | 21 |
| BoGUS A-241-320T | 80 | GGTGCCGGCCTATCTGAAGGATCAGCGTATCGTGCTCCGCTT CGGCTCTGCAACTCACAAAGCAATTGTCTATGTCAATG | 22 |
| BoGUS A-281-360B | 80 | AATGGCAGGAATCCGCCCTTGTGCTCCACGACCAGCTCACCA TTGACATAGACAATTGCTTTGTGAGTTGCAGAGCCGAA | 23 |
| BoGUS A-321-400T | 80 | GTGAGCTGGTCGTGGAGCACAAGGGCGGATTCCTGCCATTCG AAGCGGAAATCAACAACTCGCTGCGTGATGGCATGAAT | 24 |
| BoGUS A-361-460B | 100 | GTACAGCCCCACCGGTAGGGTGCTATCGTCGAGGATGTTGTC CACGGCGACGGTGACGCGATTCATGCCATCACGCAGCGAGTT GTTGATTTCCGCTTCG | 25 |
| BoGUS A-401-456T | 56 | CGCGTCACCGTCGCCGTGGACAACATCCTCGACGATAGCACC CTACCGGTGGGGCT | 26 |
| BoGUS A-41-120B | 80 | CACTTCTCTTCCAGTCCTTTCCCGTAGTCCAGCTTGAAGTTC CAGACGCCATTGAGGTCGAAGACGCCACGGGTCTCGGT | 27 |
| BoGUS A-6-40B | 35 | TTGATCGGGTACAGACTAGTCAGATCTACCATGGG | 28 |
| BoGUS A-81-160T | 80 | ACTTCAAGCTGGACTACGGGAAAGGACTGGAAGAGAAGTGGT ACGAAAGCAAGCTGACCGACACTATTAGTATGGCCGTC | 29 |
| BoGUS B-1-80T | 80 | GTACAGCGAGCGCCACGAAGAGGGCCTCGGAAAAGTCATTCG TAACAAGCCGAACTTCGACTTCTTCAACTATGCAGGCC | 30 |
| BoGUS B-121-200B | 80 | CTTTGCCTTGAAAGTCCACCGTATAGGTCACAGTCCCGGTTG GGCCATTGAAGTCGGTCACAACCGAGATGTCCTCGACG | 31 |
| BoGUS B-161-240T | 80 | ACCGGGACTGTGACCTATACGGTGGACTTTCAAGGCAAAGCC GAGACCGTGAAAGTGTCGGTCGTGGATGAGGAAGGCAA | 32 |
| BoGUS B-201-280B | 80 | CTCCACGTTACCGCTCAGGCCCTCGGTGCTTGCGACCACTTT GCCTTCCTCATCCACGACCGACACTTTCACGGTCTCGG | 33 |
| BoGUS B-241-320T | 80 | AGTGGTCGCAAGCACCGAGGGCCTGAGCGGTAACGTGGAGAT TCCGAATGTCATCCTCTGGGAACCACTGAACACGTATC | 34 |

TABLE 2-continued

| Oligo name | Size | Sequence | SEQ ID NO |
|---|---|---|---|
| BoGUS B-281-360B | 80 | GTCAGTCCGTCGTTCACCAGTTCCACTTTGATCTGGTAGAGA TACGTGTTCAGTGGTTCCCAGAGGATGACATTCGGAAT | 35 |
| BoGUS B-321-400T | 80 | TCTACCAGATCAAAGTGGAACTGGTGAACGACGGACTGACCA TCGATGTCTATGAAGAGCCGTTCGGCGTGCGGACCGTG | 36 |
| BoGUS B-361-440B | 80 | ACGGTTTGTTGTTGATGAGGAACTTGCCGTCGTTGACTTCCA CGGTCCGCACGCCGAACGGCTCTTCATAGACATCGATG | 37 |
| BoGUS B-401-480T | 80 | GAAGTCAACGACGGCAAGTTCCTCATCAACAACAAACCGTTC TACTTCAAGGGCTTTGGCAAACATGAGGACACTCCTAT | 38 |
| BoGUS B-41-120B | 80 | TACGTAAACGGGTCGTGTAGATTTTCACCGGACGGTGCAGG CCTGCATAGTTGAAGAAGTCGAAGTTCGGCTTGTTACG | 39 |
| BoGUS B-441-520B | 80 | ATCCATCACATTGCTCGCTTCGTTAAAGCCACGGCCGTTGAT AGGAGTGTCCTCATGTTTGCCAAAGCCCTTGAAGTAGA | 40 |
| BoGUS B-481-555T | 75 | CAACGGCCGTGGCTTTAACGAAGCGAGCAATGTGATGGATTT CAATATCCTCAAATGGATCGGCGCCAACAGCTT | 41 |
| BoGUS B-5-40B | 36 | AATGACTTTTCCGAGGCCCTCTTCGTGGCGCTCGCT | 42 |
| BoGUS B-521-559B | 39 | CCGGAAGCTGTTGGCGCCGATCCATTTGAGGATATTGAA | 43 |
| BoGUS B-81-160T | 80 | TGCACCGTCCGGTGAAAATCTACACGACCCCGTTTACGTACG TCGAGGACATCTCGGTTGTGACCGACTTCAATGGCCCA | 44 |
| BoGUS C-1-80T | 80 | CCGGACCGCACACTATCCGTACTCTGAAGAGTTGATGCGTCT TGCGGATCGCGAGGGTCTGGTCGTGATCGACGAGACTC | 45 |
| BoGUS C-121-200B | 80 | GTTCACGGAGAACGTCTTGATGGTGCTCAAACGTCCGAATCT TCTCCCAGGTACTGACGCGCTCGCTGCCTTCGCCGAGT | 46 |
| BoGUS C-161-240T | 80 | ATTCGGACGTTTGAGCACCATCAAGACGTTCTCCGTGAACTG GTGTCTCGTGACAAGAACCATCCAAGCGTCGTGATGTG | 47 |
| BoGUS C-201-280B | 80 | CGCGCCCTCTTCCTCAGTCGCCGCCTCGTTGGCGATGCTCCA CATCACGACGCTTGGATGGTTCTTGTCACGAGACACCA | 48 |
| BoGUS C-241-320T | 80 | GAGCATCGCCAACGAGGCGGCGACTGAGGAAGAGGGCGCGTA CGAGTACTTCAAGCCGTTGGTGGAGCTGACCAAGGAAC | 49 |
| BoGUS C-281-360B | 80 | ACAAACAGCACGATCGTGACCGGACGCTTCTGTGGGTCGAGT TCCTTGGTCAGCTCCACCAACGGCTTGAAGTACTCGTA | 50 |
| BoGUS C-321-400T | 80 | TCGACCCACAGAAGCGTCCGGTCACGATCGTGCTGTTTGTGA TGGCTACCCCGGAGACGGACAAAGTCGCCGAACTGATT | 51 |
| BoGUS C-361-440B | 80 | CGAAGTACCATCCGTTATAGCGATTGAGCGCGATGACGTCAA TCAGTTCGGCGACTTTGTCCGTCTCCGGGGTAGCCATC | 52 |
| BoGUS C-401-489T | 89 | GACGTCATCGCGCTCAATCGCTATAACGGATGGTACTTCGAT GGCGGTGATCTCGAAGCGGCCAAAGTCCATCTCCGCCAGGAA TTTCA | 53 |
| BoGUS C-41-120B | 80 | CCCGTGGTGGCCATGAAGTTGAGGTGCACGCCAACTGCCGGA GTCTCGTCGATCACGACCAGACCCTCGCGATCCGCAAG | 54 |
| BoGUS C-441-493B | 53 | CGCGTGAAATTCCTGGCGGAGATGGACTTTGGCCGCTTCGAG ATCACCGCCAT | 55 |
| BoGUS C-5'40B | 36 | ACGCATCAACTCTTCAGAGTACGGATAGTGTGCGGT | 56 |
| BoGUS C-81-160T | 80 | CGGCAGTTGGCGTGCACCTCAACTTCATGGCCACCACGGGAC TCGGCGAAGGCAGCGAGCGCGTCAGTACCTGGGAGAAG | 57 |
| BoGUS D-1-80T | 80 | CGCGTGGAACAAGCGTTGCCCAGGAAAGCCGATCATGATCAC TGAGTACGGCGCAGACACCGTTGCGGGCTTTCACGACA | 58 |
| BoGUS D-121-200B | 80 | TCGCGAAGTCCGCGAAGTTCCACGCTTGCTCACCCACGAAGT TCTCAAACTCATCGAACACGACGTGGTTCGCCTGGTAG | 59 |

TABLE 2-continued

| Oligo name | Size | Sequence | SEQ ID NO |
|---|---|---|---|
| BoGUS D-161-240T | 80 | TTCGTGGGTGAGCAAGCGTGGAACT-TCGCGGACTTCGCGACCTCT CAGGGCGTGATGCGCGTCCAAGGAAACAAGAAGGG | 60 |
| BoGUS D-201-280B | 80 | GTGCGCGGCGAGCTTCGGCTTGCGGT-CACGAGTGAACACGCCCTT CTTGTTTCCTTGGACGCGCATCACGCCCTGAGAGG | 61 |
| BoGUS D-241-320T | 80 | CGTGTTCACTCGTGACCGCAAGC-CGAAGCTCGCCGCGCACGTCTT TCGCGAGCGCTGGACCAACATTCCAGATTTCGGCT | 62 |
| BoGUS D-281-369B | 89 | CGGTCACCAATTCACACGTGATGGT-GATGGTGATGGCTAGCGTTC TTGTAGCCGAAATCTGGAATGTTGGTC-CAGCGCTCGCGAAAGAC | 63 |
| BoGUS D-321-373T | 53 | ACAAGAACGCTAGCCATCACCATCAC-CATCACGTGTGAATTGGTG ACCGGGCC | 64 |
| BoGUS D-41-120B | 80 | TACTCGACTTGATATTCCTCGGTGAA-CATCACTGGATCAATGTCG TGAAAGCCCGCAACGGTGTCTGCGCCGTACTCAGT | 65 |
| BoGUS D-5-40B | 36 | GATCATGATCGGCTTTCCTGGGCAACGCTTGTTCCA | 66 |
| BoGUS D-81-160T | 80 | TTGATCCAGTGATGTTCACCGAG-GAATATCAAGTCGAGTACTACC AGGCGAACCACGTCGTGTTCGATGAGTTTGAGAAC | 67 |

The GUS insert from pLITMUS 39 is excised and cloned into the backbone of pLAD-F48, a modular cloning vector derived from pTTQ18 (Amersham). pLAD-F48 (FIG. 15) has a lac UV5/trp hybrid promoter, a Shine-Dalgarno sequence. from lac, and a terminator from rrnB.

The AI form of microbial GUS in pLITMUS 39 is transfected into KW1 host *E. coli* cells. Bacterial cells are collected by centrifugation and resuspended in buffer (20 mM $NaPO_4$, pH 7.0, 5 mM EDTA, 5 mM EGTA, 1 mM DTT, 0.5 µg/ml leupeptin, 1 µg/ml aprotinin, 0.7 µg/ml pepstatin). This mixture is evenly suspended via a Polytron homogenizer, and the cells are broken open by agitation with glass beads or passage through a microfluidizer. For hexa-His fusion proteins, the lysate is clarified by centrifugation at 50,000 rpm for 45 min and batch absorbed on a Ni-IDA-SEPHAROSE column. The matrix is poured into a column and washed with buffer, typically either 50 mM Tris pH 7.6, 1 mM DTT; 50 mM MES pH 7.0, or IMAC buffer (for hexa-his fusions). The β-glucuronidase protein bound to the matrix is eluted in NaCl-containing buffer.

If GUS is cloned without the HexaHis tail, the lysate is centrifuged at 50,000 rpm for 45 min, and diluted with 20 mM $NaPO_4$, 1 mM EDTA, pH 7.0 (buffer A). The diluted supernatant is then loaded onto a SP-SEPHAROSE or equivalent column, and a linear gradient of 0 to 30% SP Buffer B (1 M NaCl, 20 mM $NaPO_4$, 1 mM EDTA, ph 7.0) in Buffer A with a total of 6 column volumes is applied. Fractions containing GUS are combined. Further purifications can be performed.

Example 4

MUTEINS OF CODON OPTIMIZED β-GLUCURONIDASE

Muteins of the codon-optimized GUS genes are constructed. Each of the four GUS genes described above, A0, AI, AII, and AIII, contain none, one, or four amino acid alterations. The muteins that contain one alteration have a Leu 141 to His codon change. The muteins that contain four alterations have the Leu141 to His change as well as Val138 to Ala, Tyr204 to Asp, and Thr560 to Ala changes. pLITMUS 39 containing these 12 muteins are transfected into KW1. Colonies are tested for secretion of the introduced GUS gene by staining with X-glcA. A white colony indicates undetectable GUS activity, a light blue colony indicates some detectable activity, and a dark blue colony indicates a higher level of detectable activity. As shown in the Table below, when GUS has the four mutations, no GUS activity is detectable. When GUS has a single Leu 141 to His mutation, three of the four constructs exhibit no GUS activity, while the AI construct exhibits a low level of GUS activity. All constructs exhibit GUS activity when no mutations are present. Thus, the Leu 141 to His mutation dramatically affects the activity of GUS.

| Number of Mutations | GUS construct | | | |
|---|---|---|---|---|
| | A0 | AI | AII | AIII |
| 4 | white | white | white | white |
| 1 | white | light blue | white | white |
| 0 | light blue | dark blue | light blue | light blue |

Example 5

EXPRESSION OF MICROBIAL β-GLUCURONIDASE IN YEAST, PLANTS AND *E. COLI*

A series of expression vector constructs of three different GUS genes, EcGUS, Bacillus GUS, and the A0 version of codon-optimized Bacillus GUS, are prepared and tested for enzymatic activity in *E coli*, yeast, and plants (rice, Millin variety, and Arabidopsis). The GUS genes are cloned in vectors that either contain a signal peptide suitable for the host or do not contain a signal peptide. The *E. coli* vector contains a sequence encoding a pelB signal peptide, the yeast vectors contain a sequence encoding either an invertase or Mat alpha signal peptide, and the plant vectors contain a sequence encoding either a glycine-rich protein (GRP) or extension signal peptide.

Invertase signal sequence: (SEQ ID NO: 68)
   ATGCTTTTGC AAGCCTTCCT TTTCCTTTTG GCTGGTTTTG CAGCCAAAAT ATCTGCAATG Mat alpha signal sequence: (SEQ ID NO: 69)
   ATGAGATTTC CTTCAATTTT TACTGCAGTT TTAT-TCGCAG CATCCTCCGC ATTAGCTGCT CCAGT-CAACA CTACAACAGA AGATGAAACG GCA-CAAATTC CGGCTGAAGC TGTCATCGGT TACTTAGATT TAGAAGGGGA TTTCGATGTT GCTGTTTTGC CATTTTCCAA CAGCACAAAT AACGGGTTAT TGTTTATAAA TACTACTATT GCCAGCATTG CTGCTAAAGA AGAAGGGGTA TCTTTGGATA AAAGAGAG Extension signal sequence; (SEQ ID NO: 70)
   CATGGGAAAA ATGGCTTCTC TATTTGCCAC ATTTTTAGTG GTTTTAGTGT CACTTAGCTT AGCTTCTOAA AOCTCAGCAA ATTATCAA GRP signal sequence; (SEQ ID NO: 71)
   CATGGCTACT ACTAAGCATT TGGCTCTTGC CATCCTTGTC CTCCTTAGCA TTGGTATGAC CACCAGTGCA AGAACCCTCC TA The GUS genes are cloned into each of these vectors using standard recombinant techniques of isolation of a GUS-gene containing fragment and ligation into an appropriately restricted vector. The recombinant vectors are then transfected into the appropriate host and transfectants are tested for GUS activity.

As shown in the Table below, all tested transfectants exhibited GUS activity (indicated by a +). Moreover, similar results are obtained regardless of the presence or absence of a signal peptide.

|  | E. Coli | | Yeast | | | Plants | | |
|---|---|---|---|---|---|---|---|---|
| GUS | No SP* | pelB | No SP | Invertase | Mat α | No SP | GRP | Extensin |
| EcGUS | + | NT | + | + | + | + | NT | NT |
| AI GUS | + | NT | + | + | + | NT | NT | NT |
| Bacillus GUS | + | NT | + | + | + | + | + | + |

*; SP = signal peptide; NT = not tested

Example 6

EXPRESSION OF LOW-CYSTEINE E. COLI β-GLUCURONIDASE

The E. coli GUS protein has nine cysteine residues, whereas, human GUS has four and Bacillus GUS has one. Low-cysteine muteins of E. coli GUS are constructed to provide a form of EcGUS that is secretable.

Single and multiple Cys muteins are constructed by site-directed mutagenesis techniques. Eight of the nine cysteine residues in EcGUS are changed to the corresponding residue found in human GUS based on alignment of the two protein sequences. One of the EcGUS cysteine residues, amino acid 463, aligns with a cysteine residue in human GUS and was not altered. The corresponding amino acids between EcGUS and human GUS are shown below.

| Identifier | EcGUS Cys residue no. | Human GUS corresponding amino acid |
|---|---|---|
| A | 28 | Asn |
| B | 133 | Ala |
| C | 197 | Ser |
| D | 253 | Glu |
| E | 262 | Ser |
| F | 442 | Phe |
| G | 448 | Tyr |
| H | 463 | Cys |
| I | 527 | Lys |

The mutein GUS genes are cloned into a pBS backbone. The mutations are confirmed by diagnostic restriction site changes and by DNA sequence analysis. Recombinant vectors are transfected into KW1 and GUS activity assayed by staining with X-glcA (5-bromo, 4-chloro, 3-indolyl-β-D-glucuronide).

As shown in the Table below, when the Cys residues at 443 (F), 449 (G), and 528 (I) are altered, GUS activity is greatly or completely diminished. In contrast, when the N-terminal five Cys residues (A, B, C, D, and E) are altered, GUS activity remains detectable.

| Cys changes | GUS activity |
|---|---|
| A | yes |
| B | yes |
| C | yes |
| I | no |
| D, E | yes |
| F, G | no |

-continued

| Cys changes | GUS activity |
|---|---|
| C, D, E | yes |
| B, C, D, E | yes |
| A, B, C, D, E | yes |
| A, B, C, D, E, I | no |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

SEQUENCE LISTING

<160> NUMBER OF SEQ ID NOS: 71

<210> SEQ ID NO 1
<211> LENGTH: 6029
<212> TYPE: DNA
<213> ORGANISM: Bacillus sp.

<400> SEQUENCE: 1

```
aagcttgagc ggtcatatct gccccaccca cgctcgcgtc ccaatttatt catgacttgc      60
tgggtaggcg ggaaaaactt ttcggccgct gcttcagtac tctccgcaat gaaaccatgg     120
gaatgggaag caaccggcaa cttttgacacg tcatgacctg catgagcggc tgccttttta    180
tagagcctca caagtggctc aaactgcagt gggcggcccc caataatggc tagaactagt    240
ggcaagccaa gcaggccagc acggatgacg gaatcctgac tgccgccact gccaatccaa    300
acaggtaaag gatcctgaac aggtcttggg tacacaccga gattctggat ggccggccga    360
tgtccgcctt ccagttcac cttctcggac tcccgtattt ttaacaaaag ctccagtttc     420
tcatcgaata attcatcata gtcttttaaa tcatagccaa acagcggaaa ggattcgata    480
aaggagcctc gccctgccat aatctctgca cgtccattcg atatggcatc gagggtagca    540
aaatcctgaa atactcggac tggatcagca gaagatagaa ccgtcaccgc acttgttaaa    600
cgaatccgtt ttgtctgcca agcagcggca gccaatagaa ctgctggaga tgatgccgca    660
aaatcttcgc gatgatgctc accaacacca aagcacatcca gcaatacctc gtctgcgagt    720
acaatttcct caaccacttc ccgaatccgt tgggaatgac tcatcacttc accggtttca    780
acatccggtg ttgtctctac gaacgtgctt atacctattt ccacaatcat tacctcctat    840
gtataatcgt tgctcttgt gccaaagcta tatgaatttc ttattattgc tgactttttc     900
accatatata taaatgaaag aatatttcaa acgttattat cttatatttt cctatttatt    960
tcaaaaaaat tgtttaacta gcgaaagtag gactaccata caaatgccc atgttgaaca    1020
aaacaaagca ttttttccgc cgttgtttca tacataagaa aggtgcatga ttaagaaatt    1080
ctataaaggc gcaccgagga ggacaatgat gattcaacaa accgttatga ttaacagaga    1140
agcaggttta tatgctcagc cagtcaatca attagtgcaa acagcttcac aattcaatgc    1200
tgatatcttt ctttcataca aaggacgaaa ggttagtgtg aaatcggtac tcggcgtttt    1260
atcgttagcg atacctaaac aggccgaaat tatcttagaa gtttccggag atgatgaaaa    1320
agaagcactc aaagggggtta tcaatgcgtt ggagaaatta gactagggtt ttccctttttt   1380
aataggggaat caccttgaca ttgaaaaagt ataagaaaat gaaaatagga aaaaccaatg    1440
acttaaggggg agtctctatt ggaaagagac tccccttatt caacattaga acgaaattag    1500
agcctttact tttctttcaa cttttcatcc cgatactttt ttgtaatagt ttttttcatt    1560
aataatacaa gtcctgattt tgcaagaata atccttttta gataaaaata tctatgctaa    1620
taataacatg taaccactta catttaaaaa ggagtgctat catgttatat ccaatcaata    1680
cagaaacccg aggagttttt gatttaaatg gggtctggaa ttttaaatta gattacggca    1740
aaggactgga agaaaagtgg tatgaatcaa aactgacaga taccatatca atggctgtac    1800
cttcctccta taatgatatc ggtgttacga aggaaattcg aaaccatatc ggctatgtat    1860
ggtacgagcg tgaatttacc gttcctgctt atttaaaaga tcagcgcatc gtcctgcgtt    1920
ttggttcagc aacacataag gctattgtat acgttaacga agaactagta gttgaacaca    1980
aaggcggctt cttaccgttt gaggcagaaa taaacaacag cttaagagac ggaatgaatc    2040
```

-continued

```
gtgtaacagt agcggttgat aatattttag atgattctac gctcccagtt gggctatata    2100
gtgaaagaca tgaagaaggt ttgggaaaag tgattcgtaa taaacctaat tttgacttct    2160
ttaactatgc aggcttacat cgtcctgtaa aaatttatac acccctttt acctatgttg     2220 aggatatatc ggttgtaacc gattttaacg gtccaacggg aacagttacg tatacagttg    2280
attttcaggg taaggcagaa accgtaaagg ttagtgtagt tgatgaagaa gggaaagttg    2340
ttgcttcaac tgaaggcctc tctggtaatg ttgagattcc taacgttatc ctttgggaac    2400
ctttaaatac ctatctctat caaattaaag ttgagttagt aaatgatggt ctaactattg    2460
atgtatacga agagccattt ggagttcgaa ccgttgaagt aaacgacggg aaattcctca    2520
ttaataacaa accattttat tttaaagggt cggaaaaca cgaggatact ccaataaatg     2580
gaagaggctt taatgaagca tcaaatgtaa tggattttaa tattttgaaa tggatcggtg    2640
cgaattcctt tcggacggcg cactatcctt attctgaaga actgatgcgg ctcgcagatc    2700
gtgaagggtt agtcgtcata gatgaaaccc cagcagttgg tgttcatttg aactttatgg    2760
caacgactgg tttgggcgaa ggttcagaga gagtgagtac ttgggaaaaa atccggacct    2820
ttgaacatca tcaagatgta ctgagagagc tggtttctcg tgataaaaac caccctctg    2880 ttgtcatgtg gtcgattgca aatgaagcgg ctacggaaga agaaggcgct tatgaatact    2940
ttaagccatt agttgaatta acgaaagaat tagatccaca aaaacgccca gttaccattg    3000
ttttgttcgt aatggcgaca ccagaaacag ataaagtggc ggagttaatt gatgtgattg    3060
cattgaatcg atacaacggc tggtattttg atgggggtga tcttgaagcc gcgaaagtcc    3120
accttcgtca ggaatttcat gcgtggaata acgctgtcc aggaaaacct ataatgataa    3180
cagagtatgg ggctgatacc gtagctggtt ttcatgatat tgatccggtt atgtttacag    3240
aagagtatca ggttgaatat taccaagcaa atcatgtagt atttgatgaa tttgagaact    3300
ttgttggcga gcaggcctgg aattttgcag actttgctac aagccagggt gtcatgcgtg    3360
ttcaaggtaa caaaaaaggt gttttcacac gcgaccgcaa accaaaatta gcagcacatg    3420
ttttccgcga acgttggaca aacatcccgg atttcggtta taaaattaa taaaaagctg     3480 gttctccaat aggaggccag cttttttaca tggatacaat ggttgtaaat taaaaaccct    3540
cttcattttt tatataaaaa tgaagagggt tttaattttt taaatgttat tacatttttt    3600
ctaagcccac tcatacaata tgggactttg gatagcatgg gaaacagctt ttttagactg    3660
tagttttcca gtcagctgca aattttcaa ttccttggtc tgttaaagga tgttttgata     3720
attgctcaat taccttgaat ggaatcgttg caatatgagc tccagccatc gccacacgtg    3780
taacatgatc tggatgacga acagatgcag caatgatttg tgaatccaag ttttgaatct    3840
ggaacatctt agcaatttt gcgactaatt ctacaccatc ttcgttaata tcatctaacc     3900
tgcctaagaa tggtgaaaca taagttcac ctgctcgtgc tgccagcaat gcctggttaa     3960
cactaaaaat caaagtaacg ttggttttta cacctttttt cgttagataa cggcaagcct    4020
ctagtccatc taacgtcatc ggaagtttaa ttgtaatatt tttatcgccg ccgttaattt    4080
taatgagctc atttgcttca gcaatcattt gatcagctgt caaagcatta ggtgttactt    4140
cggcagaaac agactcaacc tcgggtacgg cattaaggat ttcagcaata cggtcctcaa    4200
atttcacgcc ctctttagct actaaagaag ggttcgttgt tactcctgat aacacgccaa    4260
ttttataggc tttttgatt tcctctaggt tggcagtatc gataaaaaat ttcataatgt      4320
ttttcctcca attttagta aagtaatttt tcgtttctaa agcatgtccc caacggaaat      4380
taggttattg aatataatat aggttacttt ccgttaccat aatataacta tccgacaata    4440
```

-continued

```
atcgtcaagt aaaatgtctt gaattaaaga tatttatttt tttcaaaaga tactatttac    4500
tttactttat tgataagaat tcacgcatcc taactaggat ggcgtgaatt aactttcctt    4560
attcgacaac tccatctcgt tattgtgagg gagtacttcc tgtttctttt ttaaatactc    4620
ttgcaaagta ggagggatca tcatagccaa tcgtccaggc gatttcctct acggataaat    4680
tctctgtttt taaaggtgc ttggcttgct tcattcgtaa tatttgctga aaagcggtta     4740
aggtcatctt tgtttcgtct ttaaattttc gggaaagatg acttggatgg gtagacaatt    4800
gtgctgccaa ttcttcttta ttgatttgct tattataaaa acttagcagg tgttcaatca    4860
ccctttgggt catgtttgta tagctactta atgaattgga aatgattaaa tcgcaatatt    4920
cctcaatcat acaatcttct aattgatgca gtacttctag ttgattagca ttttcgattt    4980
cgtaagcata ttttttccgaa attcgatgaa taatgatggc aggtacttgg ctgtttcttg    5040
ctgacgtacg gagaagtatt taatataatc gctacatttt ttagtctgcg caacggctga    5100
ttgggaaatc gttcctaaaa agaaaacagc atatttttag aattaatgag ctgtaatgcc    5160
atttttttat ctccacgctc aacggcatgc atgaaatctt ttcagtcttg taccttaatt    5220
tgactagttc cgcttcttca tccacgttaa gatgattcac tttattgtga ataggacggt    5280 tgttttatc agaaacaatg acaaacgggg taatctcttc ctccaacatg tgtggaaact     5340
gctgaaggat gcttgcataa ctgctggcct gttcagcggt tagtacataa attttatcgc    5400
ttataagcat taaatcttca ctttgtggac ttgtgagacg atattccttt gataaactgt    5460
atagattcgg tgtcttatca aaatatggtc cgatgataat ggtgtaggct gcctgctttt    5520
gggtgaagga atatccgaaa tagtgtaagt cccattcgtt tatataagaa tataattggt    5580
cctgatgctt catttttcg aacaaattca gtggatcttc tttctctgaa cctggcataa     5640
atagcgggat tgcaatgatt tcatgatggt acacaaactc cccatttga tctaaaacat     5700 atgtatttaa attggttata tggtggattt tcatagtggt tgagatgatt tttggttgtt    5760
ccatctgatt cctccaattg aactttaaac cataattaaa ttcattttat cctgatattg    5820
ttaaataaat cctaaagaga atcaattgag ttcattatac tagtatcata ttcgcgcttt    5880
caattttaaa ataatgcctt tgttaaactt ggctgttgat ttccgctcca ggtgagtgcg    5940
gttcgcgggc ggtccgggga gcctcctcgg cgctaagcgc ctgtggggtg tcccctgccc    6000
cgtcctcccg caggacattg agtaagctt                                      6029
```

<210> SEQ ID NO 2
<211> LENGTH: 602
<212> TYPE: PRT
<213> ORGANISM: Bacillus sp.

<400> SEQUENCE: 2

```
Met Leu Tyr Pro Ile Asn Thr Glu Thr Arg Gly Val Phe Asp Leu Asn
  1               5                  10                  15

Gly Val Trp Asn Phe Lys Leu Asp Tyr Gly Lys Gly Leu Glu Glu Lys
                 20                  25                  30

Trp Tyr Glu Ser Lys Leu Thr Asp Thr Ile Ser Met Ala Val Pro Ser
         35                  40                  45

Ser Tyr Asn Asp Ile Gly Val Thr Lys Glu Ile Arg Asn His Ile Gly
     50                  55                  60

Tyr Val Trp Tyr Glu Arg Glu Phe Thr Pro Ala Tyr Leu Lys Asp
 65                  70                  75                  80

Gln Arg Ile Val Leu Arg Phe Gly Ser Ala Thr His Lys Ala Ile Val
                 85                  90                  95
```

-continued

Tyr Val Asn Gly Glu Leu Val Val Glu His Lys Gly Gly Phe Leu Pro
                100                 105                 110

Phe Glu Ala Glu Ile Asn Asn Ser Leu Arg Asp Gly Met Asn Arg Val
    115                 120                 125

Thr Val Ala Val Asp Asn Ile Leu Asp Asp Ser Thr Leu Pro Val Gly
    130                 135                 140

Leu Tyr Ser Glu Arg His Glu Glu Gly Leu Gly Lys Val Ile Arg Asn
145                 150                 155                 160

Lys Pro Asn Phe Asp Phe Phe Asn Tyr Ala Gly Leu His Arg Pro Val
                165                 170                 175

Lys Ile Tyr Thr Thr Pro Phe Thr Tyr Val Glu Asp Ile Ser Val Val
                180                 185                 190

Thr Asp Phe Asn Gly Pro Thr Gly Thr Val Thr Tyr Thr Val Asp Phe
    195                 200                 205

Gln Gly Lys Ala Glu Thr Val Lys Val Ser Val Val Asp Glu Glu Gly
    210                 215                 220

Lys Val Val Ala Ser Thr Glu Gly Leu Ser Gly Asn Val Glu Ile Pro
225                 230                 235                 240

Asn Val Ile Leu Trp Glu Pro Leu Asn Thr Tyr Leu Tyr Gln Ile Lys
                245                 250                 255

Val Glu Leu Val Asn Asp Gly Leu Thr Ile Asp Val Tyr Glu Glu Pro
                260                 265                 270

Phe Gly Val Arg Thr Val Glu Val Asn Asp Gly Lys Phe Leu Ile Asn
                275                 280                 285

Asn Lys Pro Phe Tyr Phe Lys Gly Phe Gly Lys His Glu Asp Thr Pro
    290                 295                 300

Ile Asn Gly Arg Gly Phe Asn Glu Ala Ser Asn Val Met Asp Phe Asn
305                 310                 315                 320

Ile Leu Lys Trp Ile Gly Ala Asn Ser Phe Arg Thr Ala His Tyr Pro
                325                 330                 335

Tyr Ser Glu Glu Leu Met Arg Leu Ala Asp Arg Glu Gly Leu Val Val
                340                 345                 350

Ile Asp Glu Thr Pro Ala Val Gly Val His Leu Asn Phe Met Ala Thr
    355                 360                 365

Thr Gly Leu Gly Glu Gly Ser Glu Arg Val Ser Thr Trp Glu Lys Ile
    370                 375                 380

Arg Thr Phe Glu His His Gln Asp Val Leu Arg Glu Leu Val Ser Arg
385                 390                 395                 400

Asp Lys Asn His Pro Ser Val Val Met Trp Ser Ile Ala Asn Glu Ala
                405                 410                 415

Ala Thr Glu Glu Glu Gly Ala Tyr Glu Tyr Phe Lys Pro Leu Val Glu
                420                 425                 430

Leu Thr Lys Glu Leu Asp Pro Gln Lys Arg Pro Val Thr Ile Val Leu
        435                 440                 445

Phe Val Met Ala Thr Pro Glu Thr Asp Lys Val Ala Glu Leu Ile Asp
        450                 455                 460

Val Ile Ala Leu Asn Arg Tyr Asn Gly Trp Tyr Phe Asp Gly Gly Asp
465                 470                 475                 480

Leu Glu Ala Ala Lys Val His Leu Arg Gln Glu Phe His Ala Trp Asn
                485                 490                 495

Lys Arg Cys Pro Gly Lys Pro Ile Met Ile Thr Glu Tyr Gly Ala Asp
                500                 505                 510

```
Thr Val Ala Gly Phe His Asp Ile Asp Pro Val Met Phe Thr Glu Glu
        515                 520                 525

Tyr Gln Val Glu Tyr Tyr Gln Ala Asn His Val Val Phe Asp Glu Phe
        530                 535                 540

Glu Asn Phe Val Gly Glu Gln Ala Trp Asn Phe Ala Asp Phe Ala Thr
545                 550                 555                 560

Ser Gln Gly Val Met Arg Val Gln Gly Asn Lys Lys Gly Val Phe Thr
                565                 570                 575

Arg Asp Arg Lys Pro Lys Leu Ala Ala His Val Phe Arg Glu Arg Trp
            580                 585                 590

Thr Asn Ile Pro Asp Phe Gly Tyr Lys Asn
        595                 600

<210> SEQ ID NO 3
<211> LENGTH: 1854
<212> TYPE: DNA
<213> ORGANISM: Bacillus sp.
<220> FEATURE:
<221> NAME/KEY: CDS
<222> LOCATION: (1)..(1854)

<400> SEQUENCE: 3 atg cta ata ata aca tgt aac cac tta cat tta aaa agg agt gct atc      48
Met Leu Ile Ile Thr Cys Asn His Leu His Leu Lys Arg Ser Ala Ile
  1               5                  10                  15 atg tta tat cca atc aat aca gaa acc cga gga gtt ttt gat tta aat      96
Met Leu Tyr Pro Ile Asn Thr Glu Thr Arg Gly Val Phe Asp Leu Asn
             20                  25                  30 ggg gtc tgg aat ttt aaa tta gat tac ggc aaa gga ctg gaa gaa aag     144
Gly Val Trp Asn Phe Lys Leu Asp Tyr Gly Lys Gly Leu Glu Glu Lys
         35                  40                  45 tgg tat gaa tca aaa ctg aca gat acc ata tca atg gct gta cct tcc     192
Trp Tyr Glu Ser Lys Leu Thr Asp Thr Ile Ser Met Ala Val Pro Ser
     50                  55                  60 tcc tat aat gat atc ggt gtt acg aag gaa att cga aac cat atc ggc     240
Ser Tyr Asn Asp Ile Gly Val Thr Lys Glu Ile Arg Asn His Ile Gly
 65                  70                  75                  80 tat gta tgg tac gag cgt gaa ttt acc gtt cct gct tat tta aaa gat     288
Tyr Val Trp Tyr Glu Arg Glu Phe Thr Val Pro Ala Tyr Leu Lys Asp
                 85                  90                  95 cag cgc atc gtc ctg cgt ttt ggt tca gca aca cat aag gct att gta     336
Gln Arg Ile Val Leu Arg Phe Gly Ser Ala Thr His Lys Ala Ile Val
            100                 105                 110 tac gtt aac gga gaa cta gta gtt gaa cac aaa ggc ggc ttc tta ccg     384
Tyr Val Asn Gly Glu Leu Val Val Glu His Lys Gly Gly Phe Leu Pro
        115                 120                 125 ttt gag gca gaa ata aac aac agc tta aga gac gga atg aat cgt gta     432
Phe Glu Ala Glu Ile Asn Asn Ser Leu Arg Asp Gly Met Asn Arg Val
    130                 135                 140 aca gta gcg gtt gat aat att tta gat gat tct acg ctc cca gtt ggg     480
Thr Val Ala Val Asp Asn Ile Leu Asp Asp Ser Thr Leu Pro Val Gly
145                 150                 155                 160 cta tat agt gaa aga cat gaa gaa ggt ttg gga aaa gtg att cgt aat     528
Leu Tyr Ser Glu Arg His Glu Glu Gly Leu Gly Lys Val Ile Arg Asn
                165                 170                 175 aaa cct aat ttt gac ttc ttt aac tat gca ggc tta cat cgt cct gta     576
Lys Pro Asn Phe Asp Phe Phe Asn Tyr Ala Gly Leu His Arg Pro Val
            180                 185                 190
```

```
aaa att tat aca acc cct ttt acc tat gtt gag gat ata tcg gtt gta    624
Lys Ile Tyr Thr Thr Pro Phe Thr Tyr Val Glu Asp Ile Ser Val Val
        195                 200                 205 acc gat ttt aac ggt cca acg gga aca gtt acg tat aca gtt gat ttt    672
Thr Asp Phe Asn Gly Pro Thr Gly Thr Val Thr Tyr Thr Val Asp Phe
    210                 215                 220 cag ggt aag gca gaa acc gta aag gtt agt gta gtt gat gaa gaa ggg    720
Gln Gly Lys Ala Glu Thr Val Lys Val Ser Val Val Asp Glu Glu Gly
225                 230                 235                 240 aaa gtt gtt gct tca act gaa ggc ctc tct ggt aat gtt gag att cct    768
Lys Val Val Ala Ser Thr Glu Gly Leu Ser Gly Asn Val Glu Ile Pro
        245                 250                 255 aac gtt atc ctt tgg gaa cct tta aat acc tat ctc tat caa att aaa    816
Asn Val Ile Leu Trp Glu Pro Leu Asn Thr Tyr Leu Tyr Gln Ile Lys
    260                 265                 270 gtt gag tta gta aat gat ggt cta act att gat gta tac gaa gag cca    864
Val Glu Leu Val Asn Asp Gly Leu Thr Ile Asp Val Tyr Glu Glu Pro
        275                 280                 285 ttt gga gtt cga acc gtt gaa gta aac gac ggg aaa ttc ctc att aat    912
Phe Gly Val Arg Thr Val Glu Val Asn Asp Gly Lys Phe Leu Ile Asn
290                 295                 300 aac aaa cca ttt tat ttt aaa ggg ttc gga aaa cac gag gat act cca    960
Asn Lys Pro Phe Tyr Phe Lys Gly Phe Gly Lys His Glu Asp Thr Pro
305                 310                 315                 320 ata aat gga aga ggc ttt aat gaa gca tca aat gta atg gat ttt aat   1008
Ile Asn Gly Arg Gly Phe Asn Glu Ala Ser Asn Val Met Asp Phe Asn
        325                 330                 335 att ttg aaa tgg atc ggt gcg aat tcc ttt cgg acg gcg cac tat cct   1056
Ile Leu Lys Trp Ile Gly Ala Asn Ser Phe Arg Thr Ala His Tyr Pro
    340                 345                 350 tat tct gaa gaa ctg atg cgg ctc gca gat cgt gaa ggg tta gtc gtc   1104
Tyr Ser Glu Glu Leu Met Arg Leu Ala Asp Arg Glu Gly Leu Val Val
        355                 360                 365 ata gat gaa acc cca gca gtt ggt gtt cat ttg aac ttt atg gca acg   1152
Ile Asp Glu Thr Pro Ala Val Gly Val His Leu Asn Phe Met Ala Thr
370                 375                 380 act ggt ttg ggc gaa ggt tca gag aga gtg agt act tgg gaa aaa atc   1200
Thr Gly Leu Gly Glu Gly Ser Glu Arg Val Ser Thr Trp Glu Lys Ile
385                 390                 395                 400 cgg acc ttt gaa cat cat caa gat gta ctg aga gag ctg gtt tct cgt   1248
Arg Thr Phe Glu His His Gln Asp Val Leu Arg Glu Leu Val Ser Arg
        405                 410                 415 gat aaa aac cac ccc tct gtt gtc atg tgg tcg att gca aat gaa gcg   1296
Asp Lys Asn His Pro Ser Val Val Met Trp Ser Ile Ala Asn Glu Ala
    420                 425                 430 gct acg gaa gaa gaa ggc gct tat gaa tac ttt aag cca tta gtt gaa   1344
Ala Thr Glu Glu Glu Gly Ala Tyr Glu Tyr Phe Lys Pro Leu Val Glu
        435                 440                 445 tta acg aaa gaa tta gat cca caa aaa cgc cca gtt acc att gtt ttg   1392
Leu Thr Lys Glu Leu Asp Pro Gln Lys Arg Pro Val Thr Ile Val Leu
450                 455                 460 ttc gta atg gcg aca cca gaa aca gat aaa gtg gcg gag tta att gat   1440
Phe Val Met Ala Thr Pro Glu Thr Asp Lys Val Ala Glu Leu Ile Asp
465                 470                 475                 480 gtg att gca ttg aat cga tac aac ggc tgg tat ttt gat ggg ggt gat   1488
Val Ile Ala Leu Asn Arg Tyr Asn Gly Trp Tyr Phe Asp Gly Gly Asp
        485                 490                 495 ctt gaa gcc gcg aaa gtc cac ctt cgt cag gaa ttt cat gcg tgg aat   1536
Leu Glu Ala Ala Lys Val His Leu Arg Gln Glu Phe His Ala Trp Asn
    500                 505                 510
```

```
aaa cgc tgt cca gga aaa cct ata atg ata aca gag tat ggg gct gat    1584
Lys Arg Cys Pro Gly Lys Pro Ile Met Ile Thr Glu Tyr Gly Ala Asp
        515                 520                 525 acc gta gct ggt ttt cat gat att gat ccg gtt atg ttt aca gaa gag    1632
Thr Val Ala Gly Phe His Asp Ile Asp Pro Val Met Phe Thr Glu Glu
    530                 535                 540 tat cag gtt gaa tat tac caa gca aat cat gta gta ttt gat gaa ttt    1680
Tyr Gln Val Glu Tyr Tyr Gln Ala Asn His Val Val Phe Asp Glu Phe
545                 550                 555                 560 gag aac ttt gtt ggc gag cag gcc tgg aat ttt gca gac ttt gct aca    1728
Glu Asn Phe Val Gly Glu Gln Ala Trp Asn Phe Ala Asp Phe Ala Thr
                565                 570                 575 agc cag ggt gtc atg cgt gtt caa ggt aac aaa aaa ggt gtt ttc aca    1776
Ser Gln Gly Val Met Arg Val Gln Gly Asn Lys Lys Gly Val Phe Thr
            580                 585                 590 cgc gac cgc aaa cca aaa tta gca gca cat gtt ttc cgc gaa cgt tgg    1824
Arg Asp Arg Lys Pro Lys Leu Ala Ala His Val Phe Arg Glu Arg Trp
        595                 600                 605 aca aac atc ccg gat ttc ggt tat aaa aat                            1854
Thr Asn Ile Pro Asp Phe Gly Tyr Lys Asn
    610                 615

<210> SEQ ID NO 4
<211> LENGTH: 618
<212> TYPE: PRT
<213> ORGANISM: Bacillus sp.

<400> SEQUENCE: 4

Met Leu Ile Ile Thr Cys Asn His Leu His Leu Lys Arg Ser Ala Ile
  1               5                  10                  15

Met Leu Tyr Pro Ile Asn Thr Glu Thr Arg Gly Val Phe Asp Leu Asn
                 20                  25                  30

Gly Val Trp Asn Phe Lys Leu Asp Tyr Gly Lys Gly Leu Glu Glu Lys
             35                  40                  45

Trp Tyr Glu Ser Lys Leu Thr Asp Thr Ile Ser Met Ala Val Pro Ser
         50                  55                  60

Ser Tyr Asn Asp Ile Gly Val Thr Lys Glu Ile Arg Asn His Ile Gly
 65                  70                  75                  80

Tyr Val Trp Tyr Glu Arg Glu Phe Thr Val Pro Ala Tyr Leu Lys Asp
                 85                  90                  95

Gln Arg Ile Val Leu Arg Phe Gly Ser Ala Thr His Lys Ala Ile Val
                100                 105                 110

Tyr Val Asn Gly Glu Leu Val Val Glu His Lys Gly Gly Phe Leu Pro
            115                 120                 125

Phe Glu Ala Glu Ile Asn Asn Ser Leu Arg Asp Gly Met Asn Arg Val
        130                 135                 140

Thr Val Ala Val Asp Asn Ile Leu Asp Asp Ser Thr Leu Pro Val Gly
145                 150                 155                 160

Leu Tyr Ser Glu Arg His Glu Glu Gly Leu Gly Lys Val Ile Arg Asn
                165                 170                 175

Lys Pro Asn Phe Asp Phe Asn Tyr Ala Gly Leu His Arg Pro Val
                180                 185                 190

Lys Ile Tyr Thr Thr Pro Phe Thr Tyr Val Glu Asp Ile Ser Val Val
            195                 200                 205

Thr Asp Phe Asn Gly Pro Thr Gly Thr Val Thr Tyr Thr Val Asp Phe
        210                 215                 220
```

```
Gln Gly Lys Ala Glu Thr Val Lys Val Ser Val Val Asp Glu Glu Gly
225                 230                 235                 240

Lys Val Val Ala Ser Thr Glu Gly Leu Ser Gly Asn Val Glu Ile Pro
                245                 250                 255

Asn Val Ile Leu Trp Glu Pro Leu Asn Thr Tyr Leu Tyr Gln Ile Lys
            260                 265                 270

Val Glu Leu Val Asn Asp Gly Leu Thr Ile Asp Val Tyr Glu Glu Pro
        275                 280                 285

Phe Gly Val Arg Thr Val Glu Val Asn Asp Gly Lys Phe Leu Ile Asn
290                 295                 300

Asn Lys Pro Phe Tyr Phe Lys Gly Phe Gly Lys His Glu Asp Thr Pro
305                 310                 315                 320

Ile Asn Gly Arg Gly Phe Asn Glu Ala Ser Asn Val Met Asp Phe Asn
                325                 330                 335

Ile Leu Lys Trp Ile Gly Ala Asn Ser Phe Arg Thr Ala His Tyr Pro
            340                 345                 350

Tyr Ser Glu Glu Leu Met Arg Leu Ala Asp Arg Glu Gly Leu Val Val
        355                 360                 365

Ile Asp Glu Thr Pro Ala Val Gly Val His Leu Asn Phe Met Ala Thr
370                 375                 380

Thr Gly Leu Gly Glu Gly Ser Glu Arg Val Ser Thr Trp Glu Lys Ile
385                 390                 395                 400

Arg Thr Phe Glu His His Gln Asp Val Leu Arg Glu Leu Val Ser Arg
                405                 410                 415

Asp Lys Asn His Pro Ser Val Val Met Trp Ser Ile Ala Asn Glu Ala
            420                 425                 430

Ala Thr Glu Glu Glu Gly Ala Tyr Glu Tyr Phe Lys Pro Leu Val Glu
        435                 440                 445

Leu Thr Lys Glu Leu Asp Pro Gln Lys Arg Pro Val Thr Ile Val Leu
450                 455                 460

Phe Val Met Ala Thr Pro Glu Thr Asp Lys Val Ala Glu Leu Ile Asp
465                 470                 475                 480

Val Ile Ala Leu Asn Arg Tyr Asn Gly Trp Tyr Phe Asp Gly Gly Asp
                485                 490                 495

Leu Glu Ala Ala Lys Val His Leu Arg Gln Glu Phe His Ala Trp Asn
            500                 505                 510

Lys Arg Cys Pro Gly Lys Pro Ile Met Ile Thr Glu Tyr Gly Ala Asp
        515                 520                 525

Thr Val Ala Gly Phe His Asp Ile Asp Pro Val Met Phe Thr Glu Glu
530                 535                 540

Tyr Gln Val Glu Tyr Tyr Gln Ala Asn His Val Val Phe Asp Glu Phe
545                 550                 555                 560

Glu Asn Phe Val Gly Glu Gln Ala Trp Asn Phe Ala Asp Phe Ala Thr
                565                 570                 575

Ser Gln Gly Val Met Arg Val Gln Gly Asn Lys Lys Gly Val Phe Thr
            580                 585                 590

Arg Asp Arg Lys Pro Lys Leu Ala Ala His Val Phe Arg Glu Arg Trp
        595                 600                 605

Thr Asn Ile Pro Asp Phe Gly Tyr Lys Asn
        610                 615

<210> SEQ ID NO 5
<211> LENGTH: 613
<212> TYPE: PRT
```

-continued

<213> ORGANISM: Homo sapiens

<400> SEQUENCE: 5

```
Leu Gly Leu Gln Gly Gly Met Leu Tyr Pro Gln Glu Ser Pro Ser Arg
  1               5                  10                  15

Glu Cys Lys Glu Leu Asp Gly Leu Trp Ser Phe Arg Ala Asp Phe Ser
             20                  25                  30

Asp Asn Arg Arg Arg Gly Phe Glu Glu Gln Trp Tyr Arg Arg Pro Leu
         35                  40                  45

Trp Glu Ser Gly Pro Thr Val Asp Met Pro Val Pro Ser Ser Phe Asn
     50                  55                  60

Asp Ile Ser Gln Asp Trp Arg Leu Arg His Phe Val Gly Trp Val Trp
 65                  70                  75                  80

Tyr Glu Arg Glu Val Ile Leu Pro Glu Arg Trp Thr Gln Asp Leu Arg
                 85                  90                  95

Thr Arg Val Val Leu Arg Ile Gly Ser Ala His Ser Tyr Ala Ile Val
            100                 105                 110

Trp Val Asn Gly Val Asp Thr Leu Glu His Glu Gly Gly Tyr Leu Pro
        115                 120                 125

Phe Glu Ala Asp Ile Ser Asn Leu Val Gln Val Gly Pro Leu Pro Ser
    130                 135                 140

Arg Leu Arg Ile Thr Ile Ala Ile Asn Asn Thr Leu Thr Pro Thr Thr
145                 150                 155                 160

Leu Pro Pro Gly Thr Ile Gln Tyr Leu Thr Asp Thr Ser Lys Tyr Pro
                165                 170                 175

Lys Gly Tyr Phe Val Gln Asn Thr Tyr Phe Asp Phe Phe Asn Tyr Ala
            180                 185                 190

Gly Leu Gln Arg Ser Val Leu Leu Tyr Thr Thr Pro Thr Thr Tyr Ile
        195                 200                 205

Asp Asp Ile Thr Val Thr Thr Ser Val Glu Gln Asp Ser Gly Leu Val
    210                 215                 220

Asn Tyr Gln Ile Ser Val Lys Gly Ser Asn Leu Phe Lys Leu Glu Val
225                 230                 235                 240

Arg Leu Leu Asp Ala Glu Asn Lys Val Val Ala Asn Gly Thr Gly Thr
                245                 250                 255

Gln Gly Gln Leu Lys Val Pro Gly Val Ser Leu Trp Trp Pro Tyr Leu
            260                 265                 270

Met His Glu Arg Pro Ala Tyr Leu Tyr Ser Leu Glu Val Gln Leu Thr
        275                 280                 285

Ala Gln Thr Ser Leu Gly Pro Val Ser Asp Phe Tyr Thr Leu Pro Val
    290                 295                 300

Gly Ile Arg Thr Val Ala Val Thr Lys Ser Gln Phe Leu Ile Asn Gly
305                 310                 315                 320

Lys Pro Phe Tyr Phe His Gly Val Asn Lys His Glu Asp Ala Asp Ile
                325                 330                 335

Arg Gly Lys Gly Phe Asp Trp Pro Leu Leu Val Lys Asp Phe Asn Leu
            340                 345                 350

Leu Arg Trp Leu Gly Ala Asn Ala Phe Arg Thr Ser His Tyr Pro Tyr
        355                 360                 365

Ala Glu Glu Val Met Gln Met Cys Asp Arg Tyr Gly Ile Val Val Ile
    370                 375                 380

Asp Glu Cys Pro Gly Val Gly Leu Ala Leu Pro Gln Phe Phe Asn Asn
385                 390                 395                 400
```

```
Val Ser Leu His His His Met Gln Val Met Glu Glu Val Val Arg Arg
            405                 410                 415

Asp Lys Asn His Pro Ala Val Val Met Trp Ser Val Ala Asn Glu Pro
            420                 425                 430

Ala Ser His Leu Glu Ser Ala Gly Tyr Tyr Leu Lys Met Val Ile Ala
            435                 440                 445

His Thr Lys Ser Leu Asp Pro Ser Arg Pro Val Thr Phe Val Ser Asn
    450                 455                 460

Ser Asn Tyr Ala Ala Asp Lys Gly Ala Pro Tyr Val Asp Val Ile Cys
465                 470                 475                 480

Leu Asn Ser Tyr Tyr Ser Trp Tyr His Asp Tyr Gly His Leu Glu Leu
                485                 490                 495

Ile Gln Leu Gln Leu Ala Thr Gln Phe Glu Asn Trp Tyr Lys Lys Tyr
                500                 505                 510

Gln Lys Pro Ile Ile Gln Ser Glu Tyr Gly Ala Glu Thr Ile Ala Gly
            515                 520                 525

Phe His Gln Asp Pro Pro Leu Met Phe Thr Glu Glu Tyr Gln Lys Ser
            530                 535                 540

Leu Leu Glu Gln Tyr His Leu Gly Leu Asp Gln Lys Arg Arg Lys Tyr
545                 550                 555                 560

Val Val Gly Glu Leu Ile Trp Asn Phe Ala Asp Phe Met Thr Glu Gln
                565                 570                 575

Ser Pro Thr Arg Val Leu Gly Asn Lys Lys Gly Ile Phe Thr Arg Gln
            580                 585                 590

Arg Gln Pro Lys Ser Ala Ala Phe Leu Leu Arg Glu Arg Tyr Trp Lys
            595                 600                 605

Ile Ala Asn Glu Thr
    610

<210> SEQ ID NO 6
<211> LENGTH: 603
<212> TYPE: PRT
<213> ORGANISM: Escherichia coli

<400> SEQUENCE: 6

Met Leu Arg Pro Val Glu Thr Pro Thr Arg Glu Ile Lys Lys Leu Asp
  1               5                  10                  15

Gly Leu Trp Ala Phe Ser Leu Asp Arg Glu Asn Cys Gly Ile Asp Gln
                20                  25                  30

Arg Trp Trp Glu Ser Ala Leu Gln Glu Ser Arg Ala Ile Ala Val Pro
            35                  40                  45

Gly Ser Phe Asn Asp Gln Phe Ala Asp Ala Asp Ile Arg Asn Tyr Ala
        50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160
```

-continued

```
Phe His Asp Phe Phe Asn Tyr Ala Gly Ile His Arg Ser Val Met Leu
            165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
            195                 200                 205

Asn Gly Asp Val Ser Val Glu Leu Arg Asp Ala Asp Gln Gln Val Val
            210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
            245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
            275                 280                 285

Tyr Phe Thr Gly Phe Gly Arg His Glu Asp Ala Asp Leu Arg Gly Lys
            290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
            325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
            355                 360                 365

Asn Lys Pro Lys Glu Leu Tyr Ser Glu Glu Ala Val Asn Gly Glu Thr
            370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
            405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
            435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
            485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
            530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
            565                 570                 575
```

Pro Lys Ser Ala Ala Phe Leu Leu Gln Lys Arg Trp Thr Gly Met Asn
              580                 585                 590

Phe Gly Glu Lys Pro Gln Gln Gly Gly Lys Gln
          595                 600

<210> SEQ ID NO 7
<211> LENGTH: 1887
<212> TYPE: DNA
<213> ORGANISM: Bacillus sp.

<400> SEQUENCE: 7

| | | | | | |
|---|---|---|---|---|---|
| atacgactca | ctagtgggtc | gacccatggt | agatctgact | agtctgtacc | cgatcaacac | 60 |
| cgagacccgt | ggcgtcttcg | acctcaatgg | cgtctggaac | ttcaagctgg | actacgggaa | 120 |
| aggactggaa | gagaagtggt | acgaaagcaa | gctgaccgac | actattagta | tggccgtccc | 180 |
| aagcagttac | aatgacattg | gcgtgaccaa | ggaaatccgc | aaccatatcg | gatatgtctg | 240 |
| gtacgaacgt | gagttcacgg | tgccggccta | tctgaaggat | cagcgtatcg | tgctccgctt | 300 |
| cggctctgca | actcacaaag | caattgtcta | tgtcaatggt | gagctggtcg | tggagcacaa | 360 |
| gggcggattc | ctgccattcg | aagcggaaat | caacaactcg | ctgcgtgatg | gcatgaatcg | 420 |
| cgtcaccgtc | gccgtggaca | acatcctcga | cgatagcacc | ctcccggtgg | ggctgtacag | 480 |
| cgagcgccac | gaagagggcc | tcggaaaagt | cattcgtaac | aagccgaact | tcgacttctt | 540 |
| caactatgca | ggcctgcacc | gtccggtgaa | aatctcacg | accccgttta | cgtacgtcga | 600 |
| ggacatctcg | gttgtgaccg | acttcaatgg | cccaaccggg | actgtgacct | atacggtgga | 660 |
| ctttcaaggc | aaagccgaga | ccgtgaaagt | gtcggtcgtg | gatgaggaag | caaagtggt | 720 |
| cgcaagcacc | gagggcctga | cggtaacgt | ggagattccg | aatgtcatcc | tctgggaacc | 780 |
| actgaacacg | tatctctacc | agatcaaagt | ggaactggtg | aacgacggac | tgaccatcga | 840 |
| tgtctatgaa | gagccgttcg | gcgtgcggac | cgtggaagtc | aacgacggca | agttcctcat | 900 |
| caacaacaaa | ccgttctact | tcaagggctt | tggcaaacat | gaggacactc | ctatcaacgg | 960 |
| ccgtggcttt | aacgaagcga | gcaatgtgat | ggatttcaat | atcctcaaat | ggatcggcgc | 1020 |
| caacagcttc | cggaccgcac | actatccgta | ctctgaagag | ttgatgcgtc | ttgcggatcg | 1080 |
| cgagggtctg | tcgtgatcg | acgagactcc | ggcagttggc | gtgcacctca | acttcatggc | 1140 |
| caccacggga | ctcggcgaag | gcagcgagcg | cgtcagtacc | tgggagaaga | ttcggacgtt | 1200 |
| tgagcaccat | caagacgttc | tccgtgaact | ggtgtctcgt | gacaagaacc | atccaagcgt | 1260 |
| cgtgatgtgg | agcatcgcca | acgaggcggc | gactgaggaa | gagggcgcgt | acgagtactt | 1320 |
| caagccgttg | gtggagctga | ccaaggaact | cgacccacag | aagcgtccgg | tcacgatcgt | 1380 |
| gctgtttgtg | atggctaccc | cggagacgga | caaagtcgcc | gaactgattg | acgtcatcgc | 1440 |
| gctcaatcgc | tataacggat | ggtacttcga | tggcggtgat | ctcgaagcgg | ccaaagtcca | 1500 |
| tctccgccag | gaatttcacg | cgtggaacaa | gcgttgccca | ggaaagccga | tcatgatcac | 1560 |
| tgagtacggc | gcagacaccg | ttgcgggctt | tcacgacatt | gatccagtga | tgttcaccga | 1620 |
| ggaatatcaa | gtcgagtact | accaggcgaa | ccacgtcgtg | ttcgatgagt | ttgagaactt | 1680 |
| cgtgggtgag | caagcgtgga | acttcgcgga | cttcgcgacc | tctcagggcg | tgatgcgcgt | 1740 |
| ccaaggaaac | aagaagggcg | tgttcactcg | tgaccgcaag | ccgaagctcg | ccgcgcacgt | 1800 |
| ctttcgcgag | cgctggacca | acattccaga | tttcggctac | aagaacgcta | gccatcacca | 1860 |
| tcaccatcac | gtgtgaattg | gtgaccg | | | | 1887 |

```
<210> SEQ ID NO 8
<211> LENGTH: 607
<212> TYPE: PRT
<213> ORGANISM: Bacillus sp.

<400> SEQUENCE: 8
```

| | | | | | | | | | | | | | | |
|---|---|---|---|---|---|---|---|---|---|---|---|---|---|---|
| Met | Val | Asp | Leu | Thr | Ser | Leu | Tyr | Pro | Ile | Asn | Thr | Glu | Thr | Arg | Gly |
| 1 | | | | 5 | | | | | 10 | | | | | 15 | |
| Val | Phe | Asp | Leu | Asn | Gly | Val | Trp | Asn | Phe | Lys | Leu | Asp | Tyr | Gly | Lys |
| | | | 20 | | | | | 25 | | | | | 30 | | |
| Gly | Leu | Glu | Glu | Lys | Trp | Tyr | Glu | Ser | Lys | Leu | Thr | Asp | Thr | Ile | Ser |
| | | 35 | | | | | 40 | | | | | 45 | | | |
| Met | Ala | Val | Pro | Ser | Ser | Tyr | Asn | Asp | Ile | Gly | Val | Thr | Lys | Glu | Ile |
| 50 | | | | | 55 | | | | | 60 | | | | | |
| Arg | Asn | His | Ile | Gly | Tyr | Val | Trp | Tyr | Glu | Arg | Glu | Phe | Thr | Val | Pro |
| 65 | | | | | 70 | | | | | 75 | | | | | 80 |
| Ala | Tyr | Leu | Lys | Asp | Gln | Arg | Ile | Val | Leu | Arg | Phe | Gly | Ser | Ala | Thr |
| | | | | 85 | | | | | 90 | | | | | 95 | |
| His | Lys | Ala | Ile | Tyr | Val | Asn | Gly | Glu | Leu | Val | Val | Glu | His | Lys | |
| | | | 100 | | | | | 105 | | | | | 110 | | |
| Gly | Gly | Phe | Leu | Pro | Phe | Glu | Ala | Glu | Ile | Asn | Asn | Ser | Leu | Arg | Asp |
| | | | 115 | | | | | 120 | | | | | 125 | | |
| Gly | Met | Asn | Arg | Val | Thr | Val | Ala | Val | Asp | Asn | Ile | Leu | Asp | Asp | Ser |
| | 130 | | | | | 135 | | | | | 140 | | | | |
| Thr | Leu | Pro | Val | Gly | Leu | Tyr | Ser | Glu | Arg | His | Glu | Glu | Gly | Leu | Gly |
| 145 | | | | | 150 | | | | | 155 | | | | | 160 |
| Lys | Val | Ile | Arg | Asn | Lys | Pro | Asn | Phe | Asp | Phe | Phe | Asn | Tyr | Ala | Gly |
| | | | | 165 | | | | | 170 | | | | | 175 | |
| Leu | His | Arg | Pro | Val | Lys | Ile | Tyr | Thr | Thr | Pro | Phe | Thr | Tyr | Val | Glu |
| | | | 180 | | | | | 185 | | | | | 190 | | |
| Asp | Ile | Ser | Val | Val | Thr | Asp | Phe | Asn | Gly | Pro | Thr | Gly | Thr | Val | Thr |
| | | 195 | | | | | 200 | | | | | 205 | | | |
| Tyr | Thr | Val | Asp | Phe | Gln | Gly | Lys | Ala | Glu | Thr | Val | Lys | Val | Ser | Val |
| | 210 | | | | | 215 | | | | | 220 | | | | |
| Val | Asp | Glu | Glu | Gly | Lys | Val | Val | Ala | Ser | Thr | Glu | Gly | Leu | Ser | Gly |
| 225 | | | | | 230 | | | | | 235 | | | | | 240 |
| Asn | Val | Glu | Ile | Pro | Asn | Val | Ile | Leu | Trp | Glu | Pro | Leu | Asn | Thr | Tyr |
| | | | | 245 | | | | | 250 | | | | | 255 | |
| Leu | Tyr | Gln | Ile | Lys | Val | Glu | Leu | Val | Asn | Asp | Gly | Leu | Thr | Ile | Asp |
| | | | | 260 | | | | | 265 | | | | | 270 | |
| Val | Tyr | Glu | Glu | Pro | Phe | Gly | Val | Arg | Thr | Val | Glu | Val | Asn | Asp | Gly |
| | | | 275 | | | | | 280 | | | | | 285 | | |
| Lys | Phe | Leu | Ile | Asn | Asn | Lys | Pro | Phe | Tyr | Phe | Lys | Gly | Phe | Gly | Lys |
| | 290 | | | | | 295 | | | | | 300 | | | | |
| His | Glu | Asp | Thr | Pro | Ile | Asn | Gly | Arg | Gly | Phe | Asn | Glu | Ala | Ser | Asn |
| 305 | | | | | 310 | | | | | 315 | | | | | 320 |
| Val | Met | Asp | Phe | Asn | Ile | Leu | Lys | Trp | Ile | Gly | Ala | Asn | Ser | Phe | Arg |
| | | | | 325 | | | | | 330 | | | | | 335 | |
| Thr | Ala | His | Tyr | Pro | Tyr | Ser | Glu | Glu | Leu | Met | Arg | Leu | Ala | Asp | Arg |
| | | | 340 | | | | | 345 | | | | | 350 | | |
| Glu | Gly | Leu | Val | Val | Ile | Asp | Glu | Thr | Pro | Ala | Val | Gly | Val | His | Leu |
| | | 355 | | | | | 360 | | | | | 365 | | | |
| Asn | Phe | Met | Ala | Thr | Thr | Gly | Leu | Gly | Glu | Gly | Ser | Glu | Arg | Val | Ser |
| | 370 | | | | | 375 | | | | | 380 | | | | |

-continued

```
Thr Trp Glu Lys Ile Arg Thr Phe Glu His His Gln Asp Val Leu Arg
385                 390                 395                 400

Glu Leu Val Ser Arg Asp Lys Asn His Pro Ser Val Val Met Trp Ser
            405                 410                 415

Ile Ala Asn Glu Ala Ala Thr Glu Glu Gly Ala Tyr Glu Tyr Phe
        420                 425                 430

Lys Pro Leu Val Glu Leu Thr Lys Glu Leu Asp Pro Gln Lys Arg Pro
                435                 440                 445

Val Thr Ile Val Leu Phe Val Met Ala Thr Pro Glu Thr Asp Lys Val
            450                 455                 460

Ala Glu Leu Ile Asp Val Ile Ala Leu Asn Arg Tyr Asn Gly Trp Tyr
465                 470                 475                 480

Phe Asp Gly Gly Asp Leu Glu Ala Ala Lys Val His Leu Arg Gln Glu
                485                 490                 495

Phe His Ala Trp Asn Lys Arg Cys Pro Gly Lys Pro Ile Met Ile Thr
            500                 505                 510

Glu Tyr Gly Ala Asp Thr Val Ala Gly Phe His Asp Ile Asp Pro Val
        515                 520                 525

Met Phe Thr Glu Glu Tyr Gln Val Glu Tyr Tyr Gln Ala Asn His Val
530                 535                 540

Val Phe Asp Glu Phe Glu Asn Phe Val Gly Glu Gln Ala Trp Asn Phe
545                 550                 555                 560

Ala Asp Phe Ala Thr Ser Gln Gly Val Met Arg Val Gln Gly Asn Lys
                565                 570                 575

Lys Gly Val Phe Thr Arg Asp Arg Lys Pro Lys Leu Ala Ala His Val
            580                 585                 590

Phe Arg Glu Arg Trp Thr Asn Ile Pro Asp Phe Gly Tyr Lys Asn
595                 600                 605

<210> SEQ ID NO 9
<211> LENGTH: 1887
<212> TYPE: DNA
<213> ORGANISM: Bacillus sp.

<400> SEQUENCE: 9
tatgctgagt gatcacccag ctgggtacca tctagactga tcagacatgg gctagttgtg      60
gctctgggca ccgcagaagc tggagttacc gcagaccttg aagttcgacc tgatgccctt     120
tcctgacctt ctcttcacca tgctttcgtt cgactggctg tgataatcat accggcaggg     180
ttcgtcaatg ttactgtaac cgcactggtt cctttaggcg ttggtatagc ctatacagac     240
catgcttgca ctcaagtgcc acggccggat agacttccta gtcgcatagc acgaggcgaa     300
gccgagacgt tgagtgtttc gttaacagat acagttacca ctcgaccagc acctcgtgtt     360
cccgcctaag gacggtaagc ttcgccttta gttgttgagc gacgcactac cgtacttagc     420
gcagtggcag cggcacctgt tgtaggagct gctatcgtgg gagggccacc ccgacatgtc     480
gctcgcggtg cttctcccgg agccttttca gtaagcattg ttcggcttga agctgaagaa     540
gttgatacgt ccggacgtgg caggccactt ttagatgtgc tggggcaaat gcatgcagct     600
cctgtagagc caaactggct gaagttaccg ggttggccct gacactgga tatgccacct     660 gaaagttccg tttcggctct ggcactttca cagccagcac ctactccttc cgtttcacca     720
gcgttcgtgg ctcccggact cgccattgca cctctaaggc ttacagtagg agacccttgg     780
tgacttgtgc atagagatgg tctagtttca ccttgaccac ttgctgcctg actggtagct     840
acagatactt ctcggcaagc cgcacgcctg gcaccttcag ttgctgccgt tcaaggagta     900
```

```
gttgttgttt ggcaagatga agttcccgaa accgtttgta ctcctgtgag gatagttgcc      960
ggcaccgaaa ttgcttcgct cgttacacta cctaaagtta taggagttta cctagccgcg     1020
gttgtcgaag gcctggcgtg tgataggcat gagacttctc aactacgcag aacgcctagc     1080
gctcccagac cagcactagc tgctctgagg ccgtcaaccg cacgtggagt tgaagtaccg     1140
gtggtgccct gagccgcttc cgtcgctcgc gcagtcatgg accctcttct aagcctgcaa     1200
actcgtggta gttctgcaag aggcacttga ccacagagca ctgttcttgg taggttcgca     1260
gcactacacc tcgtagcggt tgctccgccg ctgactcctt ctcccgcgca tgctcatgaa     1320
gttcggcaac cacctcgact ggttccttga gctgggtgtc ttcgcaggcc agtgctagca     1380
cgacaaacac taccgatggg gcctctgcct gtttcagcgg cttgactaac tgcagtagcg     1440
cgagttagcg atattgccta ccatgaagct accgccacta gagcttcgcc ggtttcaggt     1500
agaggcggtc cttaaagtgc gcaccttgtt cgcaacgggt cctttcggct agtactagtg     1560
actcatgccg cgtctgtggc aacgcccgaa agtgctgtaa ctaggtcact acaagtggct     1620
ccttatagtt cagctcatga tggtccgctt ggtgcagcac aagctactca aactcttgaa     1680
gcacccactc gttcgcacct tgaagcgcct gaagcgctgg agagtcccgc actacgcgca     1740
ggttcctttg ttcttcccgc acaagtgagc actggcgttc ggcttcgagc ggcgcgtgca     1800
gaaagcgctc gcgacctggt tgtaaggtct aaagccgatg ttcttgcgat cggtagtggt     1860
agtggtagtg cacacttaac cactggc                                         1887
```

<210> SEQ ID NO 10
<211> LENGTH: 16
<212> TYPE: PRT
<213> ORGANISM: Bacillus sp.

<400> SEQUENCE: 10

Met Leu Ile Ile Thr Cys Asn His Leu His Leu Lys Arg Ser Ala Ile
 1               5                  10                  15

<210> SEQ ID NO 11
<211> LENGTH: 4
<212> TYPE: PRT
<213> ORGANISM: Unknown
<220> FEATURE:
<223> OTHER INFORMATION: Description of Unknown Organism: Sequence that
      directs proteins to cytoplasm that may be added to the reference
      GUS

<400> SEQUENCE: 11

Lys Asp Glu Leu
 1

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Product of
      synthesis to facilitate construction and cloning

<400> SEQUENCE: 12
gtcgacccat ggtagatctg actagt                                            26

<210> SEQ ID NO 13
<211> LENGTH: 18
<212> TYPE: DNA
<213> ORGANISM: Artificial Sequence
<220> FEATURE:

```
<223> OTHER INFORMATION: Description of Artificial Sequence:   Product of
      Synthesis to facilitate construction and cloning

<400> SEQUENCE: 13
gtcgacagga gtgctatc                                                     18

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:   Product of
      Synthesis to facilitate construction and cloning

<400> SEQUENCE: 14
gtcgacagga gtgctac                                                      17

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:   Product of
      Synthesis to facilitate construction and cloning

<400> SEQUENCE: 15
gtcgacagga gtgctaccat ggtagat                                           27

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence:   Product of
      Synthesis to facilitate protein purification

<400> SEQUENCE: 16
gctagccatc accatcacca tcacgtgtga attggtgacc gggccc                      46

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:   Product of
      Synthesis to facilitate protein purification

<400> SEQUENCE: 17

Ser Ser His His His His His His Val
 1               5

<210> SEQ ID NO 18
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide. Product of Synthesis to overlap and create
      fragments of an engineered secretable microbial GUS (Figure 13)

<400> SEQUENCE: 18
tcgacccatg gtagatctga ctagtctgta cccgatcaac accgagaccc gtggcgtctt       60
cgacctcaat ggcgtctgga                                                   80

<210> SEQ ID NO 19
<211> LENGTH: 80
```

```
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 19
ggatttcctt ggtcacgcca atgtcattgt aactgcttgg gacggccata ctaatagtgt     60
cggtcagctt gctttcgtac                                                 80

<210> SEQ ID NO 20
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 20
ccaagcagtt acaatgacat tggcgtgacc aaggaaatcc gcaaccatat cggatatgtc     60
tggtacgaac gtgagttcac                                                 80

<210> SEQ ID NO 21
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 21
gcggagcacg atacgctgat ccttcagata ggccggcacc gtgaactcac gttcgtacca     60
gacatatccg atatggttgc                                                 80

<210> SEQ ID NO 22
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 22
ggtgccggcc tatctgaagg atcagcgtat cgtgctccgc ttcggtctg caactcacaa      60 agcaattgtc tatgtcaatg                                                 80

<210> SEQ ID NO 23
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 23
aatggcagga atccgcccttt gtgctccacg accagctcac cattgacata gacaattgct    60
ttgtgagttg cagagccgaa                                                 80
```

```
<210> SEQ ID NO 24
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 24
gtgagctggt cgtggagcac aagggcggat tcctgccatt cgaagcggaa atcaacaact      60
cgctgcgtga tggcatgaat                                                  80

<210> SEQ ID NO 25
<211> LENGTH: 100
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 25
gtacagcccc accggtaggg tgctatcgtc gaggatgttg tccacggcga cggtgacgcg      60
attcatgcca tcacgcagcg agttgttgat ttccgcttcg                           100

<210> SEQ ID NO 26
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 26
cgcgtcaccg tcgccgtgga caacatcctc gacgatagca ccctaccggt ggggct          56

<210> SEQ ID NO 27
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 27
cacttctctt ccagtccttt cccgtagtcc agcttgaagt tccagacgcc attgaggtcg      60
aagacgccac gggtctcggt                                                  80

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 28
ttgatcgggt acagactagt cagatctacc atggg                                 35

<210> SEQ ID NO 29
<211> LENGTH: 80
<212> TYPE: DNA
```

<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 29
acttcaagct ggactacggg aaaggactgg aagagaagtg gtacgaaagc aagctgaccg     60
acactattag tatggccgtc                                                80

<210> SEQ ID NO 30
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 30
gtacagcgag cgccacgaag agggcctcgg aaaagtcatt cgtaacaagc cgaacttcga     60
cttcttcaac tatgcaggcc                                                80

<210> SEQ ID NO 31
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 31
ctttgccttg aaagtccacc gtataggtca cagtcccggt tgggccattg aagtcggtca     60
caaccgagat gtcctcgacg                                                80

<210> SEQ ID NO 32
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 32
accgggactg tgacctatac ggtggacttt caaggcaaag ccgagaccgt gaaagtgtcg     60
gtcgtggatg aggaaggcaa                                                80

<210> SEQ ID NO 33
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 33
ctccacgtta ccgctcaggc cctcggtgct tgcgaccact ttgccttcct catccacgac     60
cgacactttc acggtctcgg                                                80

<210> SEQ ID NO 34
<211> LENGTH: 80

```
<212> TYPE: DNA
<213> ORGANISM: Artificial Sequence
<220> FEATURE:
<223> OTHER INFORMATION: Description of Artificial Sequence:
      Oligonucleotide. Product of Synthesis to Overlap and create
      fragments of engineered secretable microbial GUS (Figure 13)

<400> SEQUENCE: 34
agtggtcgca agcaccgagg gcctgagcgg taacgtggag attccgaatg tcatcctctg    60
ggaaccactg aacacgtatc                                                80

<210> SEQ ID NO 35
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide. Product of Synthesis to Overlap and create
      fragments of engineered secretable microbial GUS (Figure 13)

<400> SEQUENCE: 35
gtcagtccgt cgttcaccag ttccactttg atctggtaga gatacgtgtt cagtggttcc    60
cagaggatga cattcggaat                                                80

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide. Product of Synthesis to Overlap and create
      fragments of engineered secretable microbial GUS (Figure 13)

<400> SEQUENCE: 36
tctaccagat caaagtggaa ctggtgaacg acggactgac catcgatgtc tatgaagagc    60
cgttcggcgt gcggaccgtg                                                80

<210> SEQ ID NO 37
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide. Product of Synthesis to Overlap and create
      fragments of engineered secretable microbial GUS (Figure 13)

<400> SEQUENCE: 37
acggtttgtt gttgatgagg aacttgccgt cgttgacttc cacggtccgc acgccgaacg    60
gctcttcata gacatcgatg                                                80

<210> SEQ ID NO 38
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide. Product of Synthesis to Overlap and create
      fragments of engineered secretable microbial GUS (Figure 13)

<400> SEQUENCE: 38
gaagtcaacg acggcaagtt cctcatcaac aacaaaccgt tctacttcaa gggctttggc    60
aaacatgagg acactcctat                                                80
```

```
<210> SEQ ID NO 39
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 39
tacgtaaacg gggtcgtgta gattttcacc ggacggtgca ggcctgcata gttgaagaag      60
tcgaagttcg gcttgttacg                                                  80

<210> SEQ ID NO 40
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 40
atccatcaca ttgctcgctt cgttaaagcc acggccgttg ataggagtgt cctcatgttt      60
gccaaagccc ttgaagtaga                                                  80

<210> SEQ ID NO 41
<211> LENGTH: 75
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 41
caacggccgt ggctttaacg aagcgagcaa tgtgatggat ttcaatatcc tcaaatggat      60
cggcgccaac agctt                                                       75

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 42
aatgactttt ccgaggccct cttcgtggcg ctcgct                                36

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 43
ccggaagctg ttggcgccga tccatttgag gatattgaa                             39

<210> SEQ ID NO 44
<211> LENGTH: 80
<212> TYPE: DNA
```

<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 44
tgcaccgtcc ggtgaaaatc tacacgaccc cgtttacgta cgtcgaggac atctcggttg    60
tgaccgactt caatggccca                                                80

<210> SEQ ID NO 45
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 45
ccggaccgca cactatccgt actctgaaga gttgatgcgt cttgcggatc gcgagggtct    60
ggtcgtgatc gacgagactc                                                80

<210> SEQ ID NO 46
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 46
gttcacggag aacgtcttga tggtgctcaa acgtccgaat cttctcccag gtactgacgc    60
gctcgctgcc ttcgccgagt                                                80

<210> SEQ ID NO 47
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 47
attcggacgt ttgagcacca tcaagacgtt ctccgtgaac tggtgtctcg tgacaagaac    60
catccaagcg tcgtgatgtg                                                80

<210> SEQ ID NO 48
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 48
cgcgccctct tcctcagtcg ccgcctcgtt ggcgatgctc cacatcacga cgcttggatg    60
gttcttgtca cgagacacca                                                80

<210> SEQ ID NO 49
<211> LENGTH: 80

```
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 49
gagcatcgcc aacgaggcgg cgactgagga agagggcgcg tacgagtact tcaagccgtt      60
ggtggagctg accaaggaac                                                  80

<210> SEQ ID NO 50
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 50
acaaacagca cgatcgtgac cggacgcttc tgtgggtcga gttccttggt cagctccacc      60
aacggcttga agtactcgta                                                  80

<210> SEQ ID NO 51
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 51
tcgacccaca gaagcgtccg gtcacgatcg tgctgtttgt gatggctacc ccggagacgg      60
acaaagtcgc cgaactgatt                                                  80

<210> SEQ ID NO 52
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 52
cgaagtacca tccgttatag cgattgagcg cgatgacgtc aatcagttcg gcgactttgt      60
ccgtctccgg ggtagccatc                                                  80

<210> SEQ ID NO 53
<211> LENGTH: 89
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 53
gacgtcatcg cgctcaatcg ctataacgga tggtacttcg atggcggtga tctcgaagcg      60
gccaaagtcc atctccgcca ggaatttca                                        89
```

```
<210> SEQ ID NO 54
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 54
cccgtggtgg ccatgaagtt gaggtgcacg ccaactgccg gagtctcgtc gatcacgacc      60
agaccctcgc gatccgcaag                                                  80

<210> SEQ ID NO 55
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 55
cgcgtgaaat tcctggcgga gatggacttt ggccgcttcg agatcaccgc cat             53

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial US (Figure 13)

400> SEQUENCE: 56 acgcatcaac tcttcagagt acggatagtg tgcggt                                36

<210> SEQ ID NO 57
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 57
cggcagttgg cgtgcacctc aacttcatgg ccaccacggg actcggcgaa ggcagcgagc      60
gcgtcagtac ctgggagaag                                                  80

<210> SEQ ID NO 58
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 58
cgcgtggaac aagcgttgcc caggaaagcc gatcatgatc actgagtacg gcgcagacac      60
cgttgcgggc tttcacgaca                                                  80

<210> SEQ ID NO 59
<211> LENGTH: 80
<212> TYPE: DNA
```

<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 59
tcgcgaagtc cgcgaagttc cacgcttgct cacccacgaa gttctcaaac tcatcgaaca    60
cgacgtggtt cgcctggtag                                                80

<210> SEQ ID NO 60
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 60
ttcgtgggtg agcaagcgtg gaacttcgcg gacttcgcga cctctcaggg cgtgatgcgc    60
gtccaaggaa acaagaaggg                                                80

<210> SEQ ID NO 61
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 61
gtgcgcggcg agcttcggct tgcggtcacg agtgaacacg cccttcttgt ttccttggac    60
gcgcatcacg ccctgagagg                                                80

<210> SEQ ID NO 62
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 62
cgtgttcact cgtgaccgca agccgaagct cgccgcgcac gtctttcgcg agcgctggac    60
caacattcca gatttcggct                                                80

<210> SEQ ID NO 63
<211> LENGTH: 89
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 63
cggtcaccaa ttcacacgtg atggtgatgg tgatggctag cgttcttgta gccgaaatct    60
ggaatgttgg tccagcgctc gcgaaagac                                      89

<210> SEQ ID NO 64
<211> LENGTH: 53

```
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 64
acaagaacgc tagccatcac catcaccatc acgtgtgaat tggtgaccgg gcc          53

<210> SEQ ID NO 65
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 65
tactcgactt gatattcctc ggtgaacatc actggatcaa tgtcgtgaaa gcccgcaacg   60
gtgtctgcgc cgtactcagt                                               80

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 66
gatcatgatc ggctttcctg ggcaacgctt gttcca                             36

<210> SEQ ID NO 67
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide.  Product of Synthesis to Overlap and create
      fragments of engineered secretable microbial GUS (Figure 13)

<400> SEQUENCE: 67
ttgatccagt gatgttcacc gaggaatatc aagtcgagta ctaccaggcg aaccacgtcg   60
tgttcgatga gtttgagaac                                               80

<210> SEQ ID NO 68
<211> LENGTH: 60
<212> TYPE: DNA
<213> ORGANISM: Unknown
<220> FEATURE:
<223> OTHER INFORMATION: Description of Unknown Organism:  Invertase
      Signal Sequence used in yeast vector

<400> SEQUENCE: 68
atgcttttgc aagccttcct tttccttttg gctggttttg cagccaaaat atctgcaatg   60

<210> SEQ ID NO 69
<211> LENGTH: 258
<212> TYPE: DNA
<213> ORGANISM: Unknown
<220> FEATURE:
<223> OTHER INFORMATION: Description of Unknown Organism:  Mat alpha
      signal sequence used in yeast vector
```

-continued

```
<400> SEQUENCE: 69
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tacttagatt tagaagggga tttcgatgtt gctgttttgc cattttccaa cagcacaaat    180
aacgggttat tgtttataaa tactactatt gccagcattg ctgctaaaga agaagggta     240 tctttggata aaagagag                                                   258

<210> SEQ ID NO 70
<211> LENGTH: 88
<212> TYPE: DNA
<213> ORGANISM: Unknown
<220> FEATURE:
<223> OTHER INFORMATION: Description of Unknown Organism:  Extension
      signal sequence used in plant vector

<400> SEQUENCE: 70
catgggaaaa atggcttctc tatttgccac atttttagtg gttttagtgt cacttagctt     60
agcttctgaa agctcagcaa attatcaa                                        88

<210> SEQ ID NO 71
<211> LENGTH: 82
<212> TYPE: DNA
<213> ORGANISM: Unknown
<220> FEATURE:
<223> OTHER INFORMATION: Description of Unknown Organism:  GRP signal
      sequence used in plant vector

<400> SEQUENCE: 71
catggctact actaagcatt tggctcttgc catccttgtc ctccttagca ttggtatgac     60
caccagtgca agaaccctcc ta                                              82
```

We claim:

1. An isolated nucleic acid molecule comprising a nucleic acid sequence encoding a secreted form of microbial Bacillus β-glucuronidase.

2. The nucleic acid molecule of claim 1, wherein the nucleic acid sequence comprises nucleotides 1662–3467 of FIG. 1 (SEQ ID NO: 1) or hybridizes under stringent conditions to the complement of the sequence comprising nucleotides 1662–3467 of FIG. 1 (SEQ ID NO: 1), and which encodes a functional β-glucuronidase.

3. The nucleic acid molecule of claim 1, wherein the nucleic acid molecule encodes the amino acid sequence of FIG. 3 (SEQ ID NO: 2), or a variant thereof, and which encodes a functional β-glucuronidase.

4. The nucleic acid molecule of claim 3, further comprising a second nucleic acid molecule that encodes the amino acid sequence of FIG. 4A (SEQ ID NO: 4), or a variant thereof, and wherein the second nucleic acid molecule is fused to the 5' end of the nucleic acid molecule encoding β-glucuronidase.

5. An isolated nucleic acid molecule encoding a membrane-bound form of Bacillus β-glucuronidase.

6. The nucleic acid molecule of claim 5, further comprising a sequence encoding an outer membrane-spanning peptide fused to the sequence encoding β-glucuronidase.

7. A vector, comprising a nucleic acid molecule encoding a secreted form of a microbial Bacillus β-glucuronidase, wherein the β-glucuronidase sequence is in operative linkage with a promoter element.

8. The vector of claim 7, wherein the vector is a binary Agrobacterium tumefaciens plasmid vector.

9. The vector of claim 7, wherein the promoter element is a promoter selected from the group consisting of a developmental type-specific promoter, a tissue type-specific promoter, a cell type-specific promoter and an inducible promoter.

10. The vector of claim 9, wherein the promoter element is selected from a group consisting of a promoter functional in a plant cell, a promoter functional in a bacterium, a promoter functional in an animal cell and a promoter functional in a fungal cell.

11. The vector of claim 7, wherein the vector is functional in a bacterium.

12. The vector of claim 7, further comprising a nucleic acid sequence encoding a product of a gene of interest or portion thereof.

13. The vector of claim 12, wherein the product is a protein.

14. A host cell containing the vector according to claim 7.

15. The host cell of claim 14, wherein the host cell is selected from the group consisting of a plant cell, an insect cell, a fungal cell, an animal cell and a bacterial cell.

16. A method of introducing a controller element into a host cell, comprising introducing into a host cell a vector construct, the vector construct comprising nucleic acid sequence encoding a secreted form of microbial β-glucuronidase and a nucleic acid sequence controller element, wherein the nucleic acid sequence encoding the β-glucuronidase (a) encodes a protein comprising the amino acid sequence of FIG. 3 (SEQ ID NO: 2) or (b) hybridizes under stringent conditions to the complement of nucleotides 1662–3467 of FIG. 1 (SEQ ID NO: 1), and which encodes a functional beta-glucuronidase, and wherein the nucleic acid sequence encoding β-glucuronidase is in operative linkage with the controller element.

17. The method according to claim 16, wherein the host cell is selected from the group consisting of a plant cell, an animal cell, an insect cell, a fungal cell and a bacterial cell.

18. The method according to claim 16, wherein the vector construct is a binary Agrobacterium vector.

19. The method according to claim 16, wherein the controller element is selected from the group consisting of a promoter, an enhancer, an operator, a ribosome binding site, a signal peptide sequence, a chloroplast targeting sequence, a mitochondrial localization sequence, a nucleus targeting sequence and an intron.

20. The method according to claim 19, wherein the controller element is functional in a plant cell.

21. The method according to claim 19, wherein the controller element is a promoter selected from the group consisting of a developmental type-specific promoter, a tissue type-specific promoter, a cell type-specific promoter and an inducible promoter.

22. A method of monitoring expression of gene of interest or a portion thereof in a host cell comprising:
   (a) introducing into the host cell a vector construct, the vector construct comprising nucleic acid sequence encoding a secreted form of microbial β-glucuronidase and nucleic acid sequence encoding a product of the gene of interest or a portion thereof;
      wherein the nucleic acid sequence encoding the microbial β-glucuronidase (a) encodes a protein comprising the amino acid sequence of FIG. 3 (SEQ ID NO: 2) or (b) hybridizes under stringent conditions to the complement of nucleotides 1662–3467 of FIG. 1 (SEQ ID NO: 1) and which encodes a functional β-glucuronidase, and
   (b) detecting the presence of secreted microbial β-glucuronidase, thereby monitoring expression of the gene of interest.

23. The method according to claim 22, wherein the host cell is selected from the group consisting of a plant cell, an animal cell, an insect cell, a fungal cell and a bacterial cell.

24. The method according to claim 22, wherein the product is a protein.

25. The method according to claim 22, wherein the vector construct further comprises a promoter.

26. The method according to claim 22, wherein the nucleic acid sequence encoding the product and the nucleic acid sequence encoding β-glucuronidase are in operative linkage with the same promoter.

27. A method of monitoring activity of a controller element in a host cell, comprising:
   (a) introducing into the host cell a vector construct, the vector construct comprising nucleic acid sequence encoding a secreted form of microbial β-glucuronidase and a nucleic acid sequence of the controller element;
      wherein the nucleic acid sequence encoding the β-glucuronidase (a) encodes a protein comprising the amino acid sequence of FIG. 3 (SEQ ID NQ:2) or (b) hybridizes under stringent conditions to the complement of nucleotides 1662–3467 of FIG. 1 (SEQ ID NO:1) and which encodes a functional β-glucuronidase, and
      wherein the nucleic acid sequence encoding β-glucuronidase is in operative linkage with the controller element; and
   (b) detecting the presence of secreted β-glucuronidase, thereby monitoring activity of the controller element.

28. The method according to claim 27, wherein the host cell is selected from the group consisting of a plant cell, an animal cell, an insect cell, a fungal cell and a bacterial cell.

29. The method according to claim 27, wherein the vector construct is a binary Agrobacterium vector.

30. The method according to claim 27, wherein the controller element is selected from the group consisting of a promoter, an enhancer, an operator, a ribosome binding site, a signal peptide sequence, a chloroplast targeting sequence, a mitochondrial localization sequence, a nucleus targeting sequence and an intron.

31. The method according to claim 27, wherein the controller element is a promoter functional in a plant cell.

32. A method for transforming a host cell with a gene of interest or portion thereof, comprising:
   (a) introducing into the host cell a vector construct, the vector construct comprising nucleic acid sequence encoding a secreted form of microbial β-glucuronidase and nucleic acid sequence encoding a product of the gene of interest or a portion thereof, such that the vector construct integrates into the genome of the host cell;
      wherein the nucleic acid sequence encoding β-glucuronidase (i) encodes a protein comprising the amino acid sequence of FIG. 3 (SEO ID NO: 2) or (ii) hybridizes under stringent conditions to the complement of nucleotides 1662–3467 of FIG. 1 (SEQ ID NO: 1) and which encodes a functional β-glucuronidase; and
   (c) detecting the presence of secreted β-glucuronidase, thereby establishing that the host cell is transformed.

33. The method according to claim 32, wherein the host cell is selected from the group consisting of a plant cell, an animal cell, an insect cell, a fungal cell and a bacterial cell.

34. The method according to claim 32, wherein the vector construct is a binary Agrobacterium vector.

35. The method according to claim 32, wherein the product is a protein.

36. The method according to claim 32, wherein the vector construct further comprises a promoter.

37. The method according to claim 32, wherein the gene of interest and β-glucuronidase are under control of the same promoter.

* * * * *

UNITED STATES PATENT AND TRADEMARK OFFICE
CERTIFICATE OF CORRECTION

PATENT NO.    : 6,391,547 B1
DATED         : May 21, 2002
INVENTOR(S)   : Richard A. Jefferson, Rebecca L. Harcourt, Andrzej Kilian and Paul K. Keese It is certified that error appears in the above-identified patent and that said Letters Patent is hereby corrected as shown below:

<u>Title page,</u>
Item [75], Inventors, please delete "Katherine Joanna Wilson, Townsville;" so that the Inventors read -- Richard A. Jefferson, Googong; Rebecca Louise Harcourt, Sydney; Andrzej Kilian, Kaleen; Paul Konrad Keese, Curtin, all of (AU) --

Signed and Sealed this

First Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,391,547 B1
DATED : May 21, 2002
INVENTOR(S) : Richard A Jefferson et al.

It is certified that error appears in the above-identified patent and that said Letters Patent is hereby corrected as shown below:

Title page,
Item [62], please delete the entire "[62] Division of application No. 08/882,704, filed on Jun. 25, 1997, now Pat. No. 5,879,906."

Signed and Sealed this

Fifteenth Day of March, 2005

JON W. DUDAS
*Director of the United States Patent and Trademark Office*